United States Patent
Chou et al.

(10) Patent No.: US 11,312,003 B1
(45) Date of Patent: Apr. 26, 2022

(54) ROBOTIC MOBILITY DEVICE AND CONTROL

(71) Applicant: IKUTUKI, Berkeley, CA (US)

(72) Inventors: Wenpei Chou, Berkeley, CA (US); Da Jiun Chou, Berkeley, CA (US)

(73) Assignee: IKUTUKI, Berkeley, CA (US)

( * ) Notice: Subject to any disclaimer, the term of this patent is extended or adjusted under 35 U.S.C. 154(b) by 247 days.

(21) Appl. No.: 16/748,804

(22) Filed: Jan. 22, 2020

Related U.S. Application Data

(62) Division of application No. 15/472,662, filed on Mar. 29, 2017, now Pat. No. 10,576,620.

(51) Int. Cl.
| | |
|---|---|
| *A61F 5/02* | (2006.01) |
| *A61F 2/72* | (2006.01) |
| *B25J 9/00* | (2006.01) |
| *A61H 3/00* | (2006.01) |
| *A61F 5/01* | (2006.01) |
| *A63B 71/12* | (2006.01) |

(52) U.S. Cl.
CPC .............. *B25J 9/0006* (2013.01); *A61F 2/72* (2013.01); *A61F 5/0102* (2013.01); *A63B 71/1225* (2013.01); *A61F 2005/0144* (2013.01); *A61H 2201/1602* (2013.01)

(58) Field of Classification Search
None
See application file for complete search history.

(56) References Cited

U.S. PATENT DOCUMENTS

| | | | |
|---|---|---|---|
| 5,695,452 A * | 12/1997 | Grim | B29C 44/0446 |
| | | | 602/19 |
| 7,707,654 B1 * | 5/2010 | Spence | A61H 7/003 |
| | | | 2/163 |
| 9,022,965 B2 * | 5/2015 | Auberger | A61F 5/0125 |
| | | | 602/26 |
| 9,492,302 B2 * | 11/2016 | Wiggin | A61F 5/0127 |
| 10,265,237 B2 * | 4/2019 | Devanaboyina | |
| | | | A63B 21/00181 |
| 10,278,885 B1 * | 5/2019 | Smith | A61H 1/024 |
| 10,357,381 B2 * | 7/2019 | Kuiken | A61F 2/64 |

(Continued)

*Primary Examiner* — Ann Schillinger
(74) *Attorney, Agent, or Firm* — Charles H Jew

(57) ABSTRACT

Robotic mobility assistant exoskeleton with frame members, which are attached adjacent to biological joints, supplements relative movement between skeletal members. Mechanical joint defines a center of relative rotation of frame members about three mutually perpendicular axes with the center of relative rotation of frame members being displaced from the outer surfaces of skeletal members to correspond in position with the center of biological joint. Actuation devices including powered cable springs rotate frame members. Control system executes calibrated user specific posture sequences and activates power. Mechanical joint exhibits cylindrical guide surfaces defining a slidable or rotatable connection of frame members and has a radius intersecting the center of the biological joint. Node control network distributes computing load and reduces communications overhead. Map unit has object recognition system for monitoring environment. Standard posture data derived from rules of ambulation and posture provide positioning control, optimized by energy-timed margins for balance maintenance.

20 Claims, 39 Drawing Sheets

(56) References Cited

U.S. PATENT DOCUMENTS

| | | | | |
|---|---|---|---|---|
| 2003/0120183 A1* | 6/2003 | Simmons | ............... | A61F 4/00 |
| | | | | 600/595 |
| 2006/0167394 A1* | 7/2006 | Ceriani | ............... | A61F 5/0123 |
| | | | | 602/26 |
| 2009/0188656 A1* | 7/2009 | Xu | ............... | F28F 9/0224 |
| | | | | 165/173 |
| 2009/0299243 A1* | 12/2009 | Hirata | ............... | A61F 5/0193 |
| | | | | 602/23 |
| 2010/0262054 A1* | 10/2010 | Summit | ............... | G06F 30/00 |
| | | | | 700/98 |
| 2013/0289452 A1* | 10/2013 | Smith | ............... | A63B 21/4009 |
| | | | | 601/33 |
| 2014/0277739 A1* | 9/2014 | Kornbluh | ............... | F16D 28/00 |
| | | | | 29/428 |
| 2015/0173993 A1* | 6/2015 | Walsh | ............... | B25J 9/0006 |
| | | | | 414/4 |
| 2016/0107309 A1* | 4/2016 | Walsh | ............... | A61B 5/6831 |
| | | | | 248/550 |
| 2017/0049659 A1* | 2/2017 | Farris | ............... | B25J 9/104 |
| 2017/0202724 A1* | 7/2017 | De Rossi | ............... | A61H 3/00 |

* cited by examiner

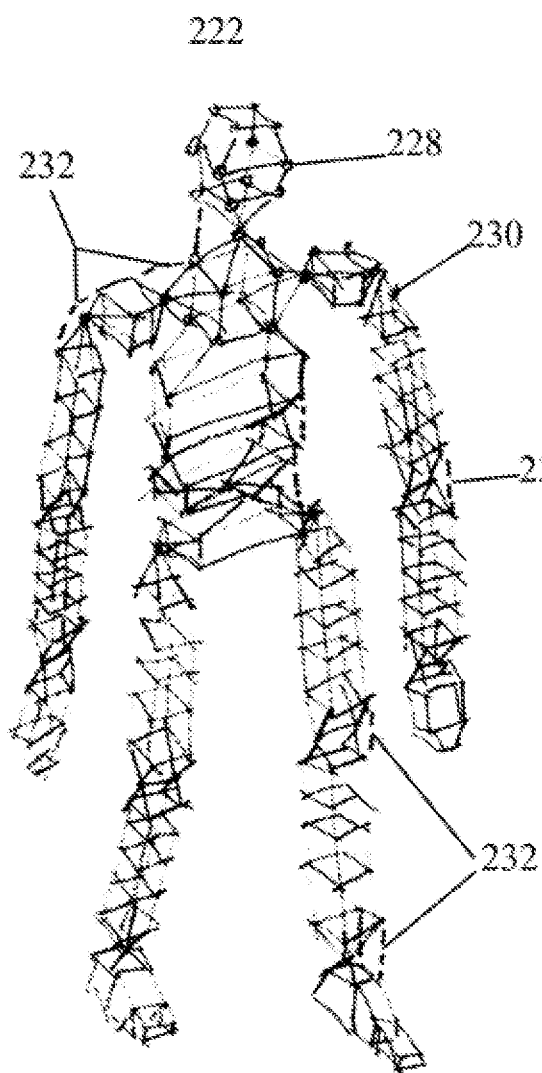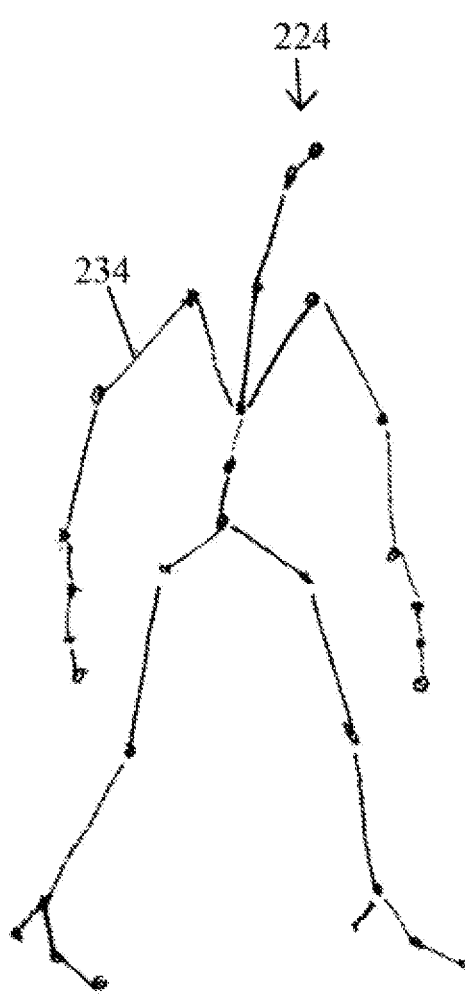
*FIG. 3A*  *FIG. 3B*

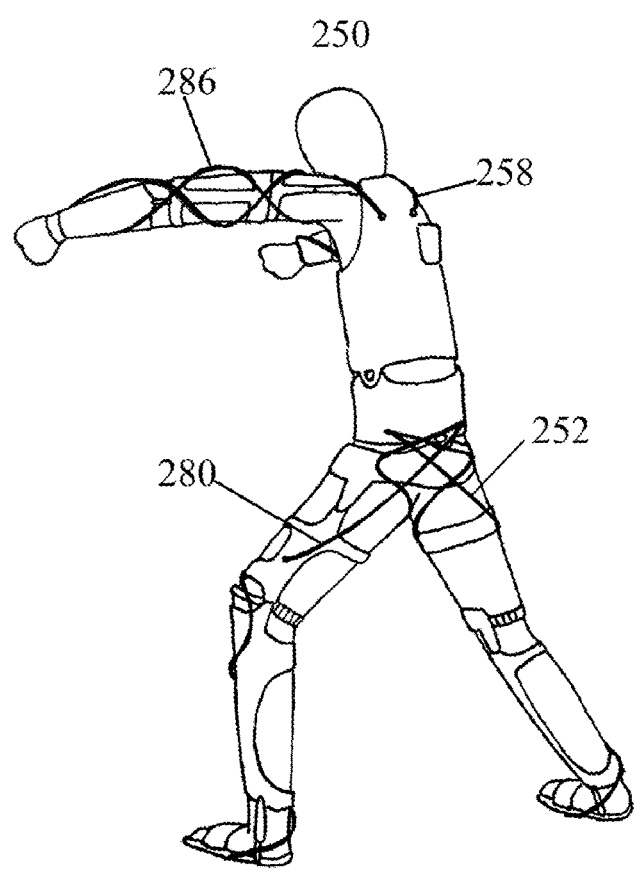
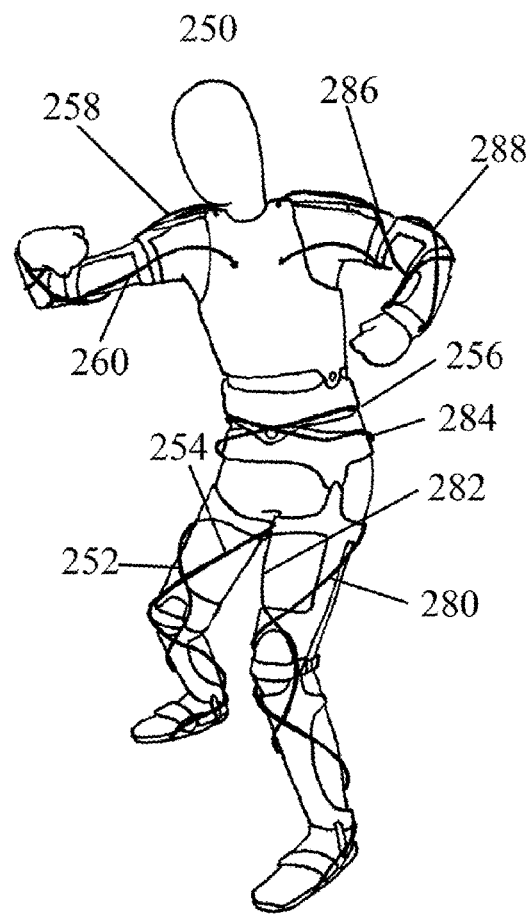
FIG. 9A
FIG. 9B

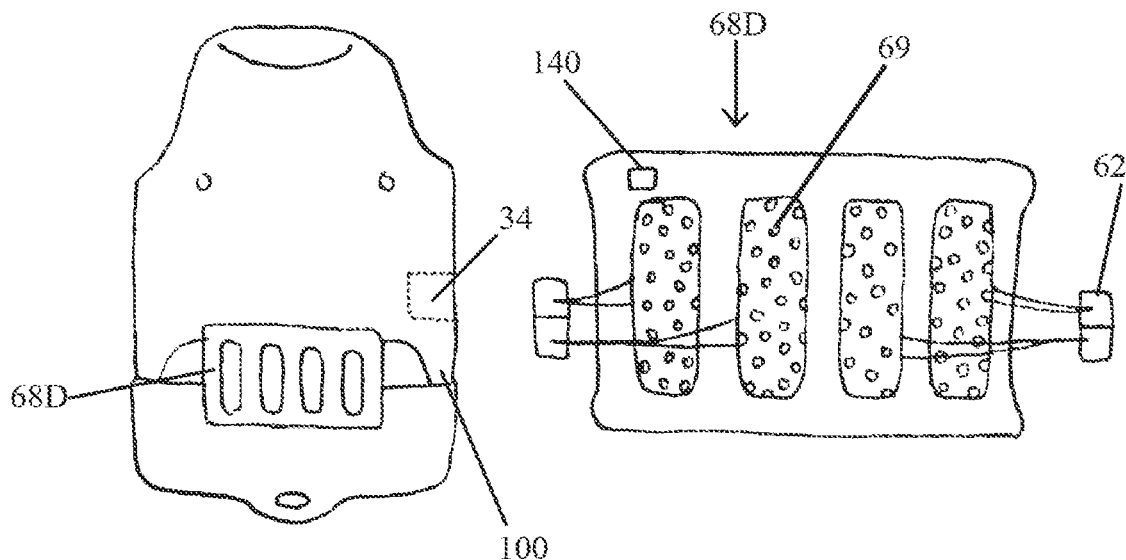
FIG. 11A  FIG. 11B
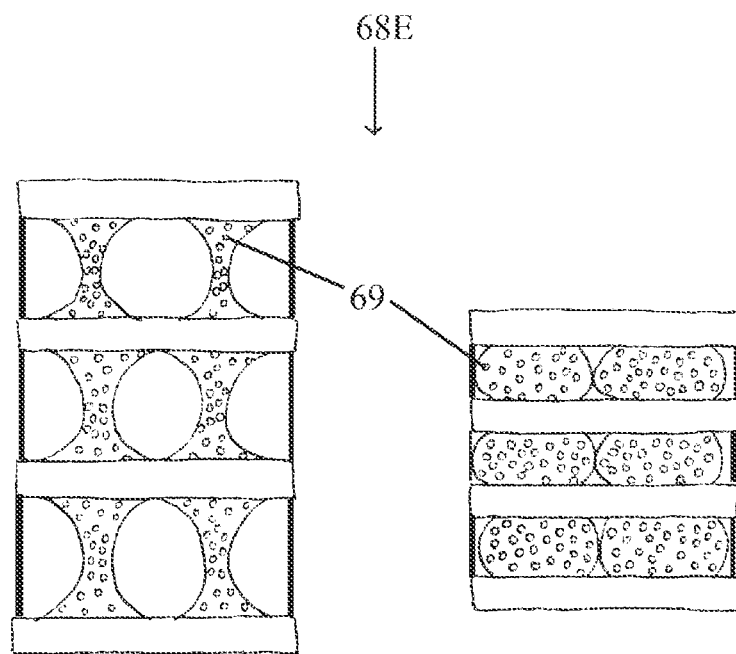
FIG. 11C  FIG. 11D

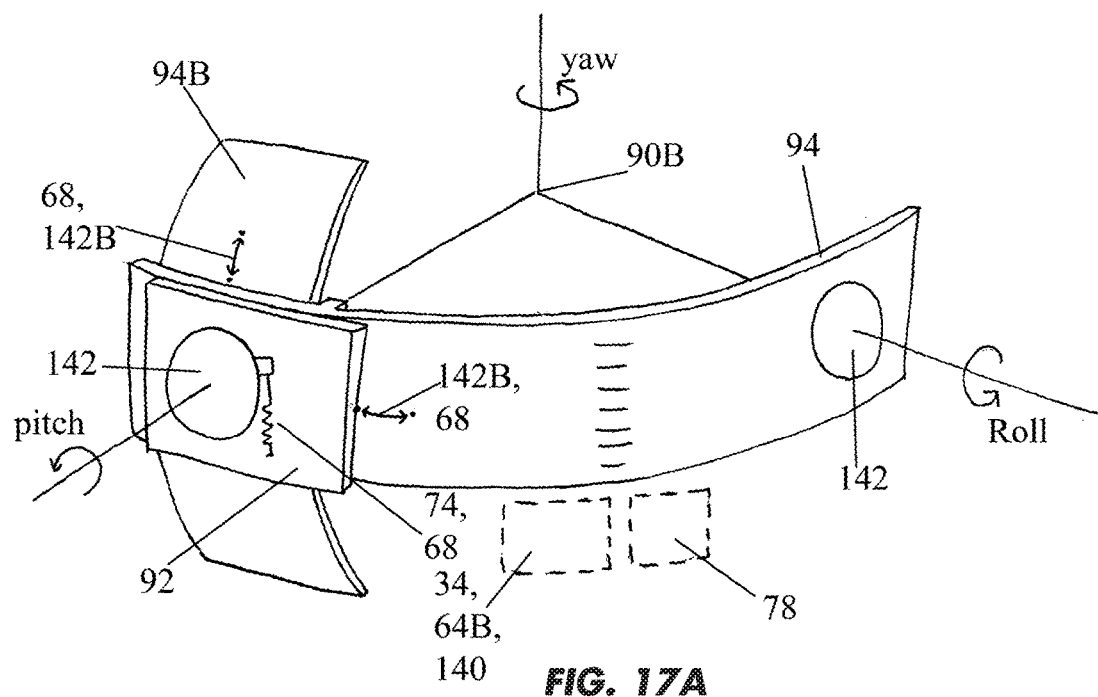
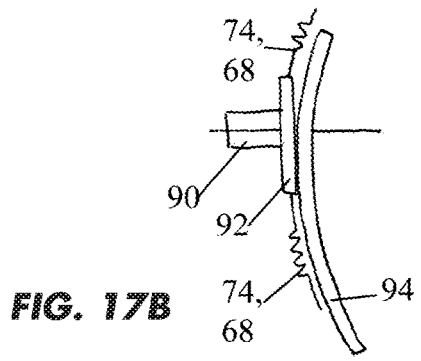
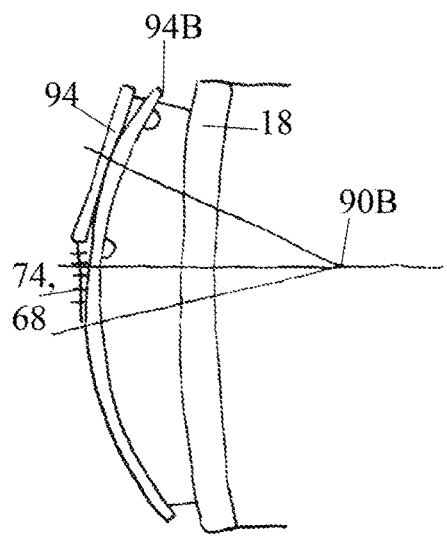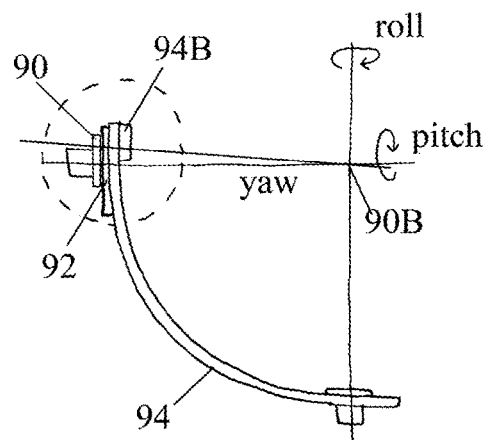
FIG. 17A
FIG. 17B
FIG. 17C
FIG. 17D

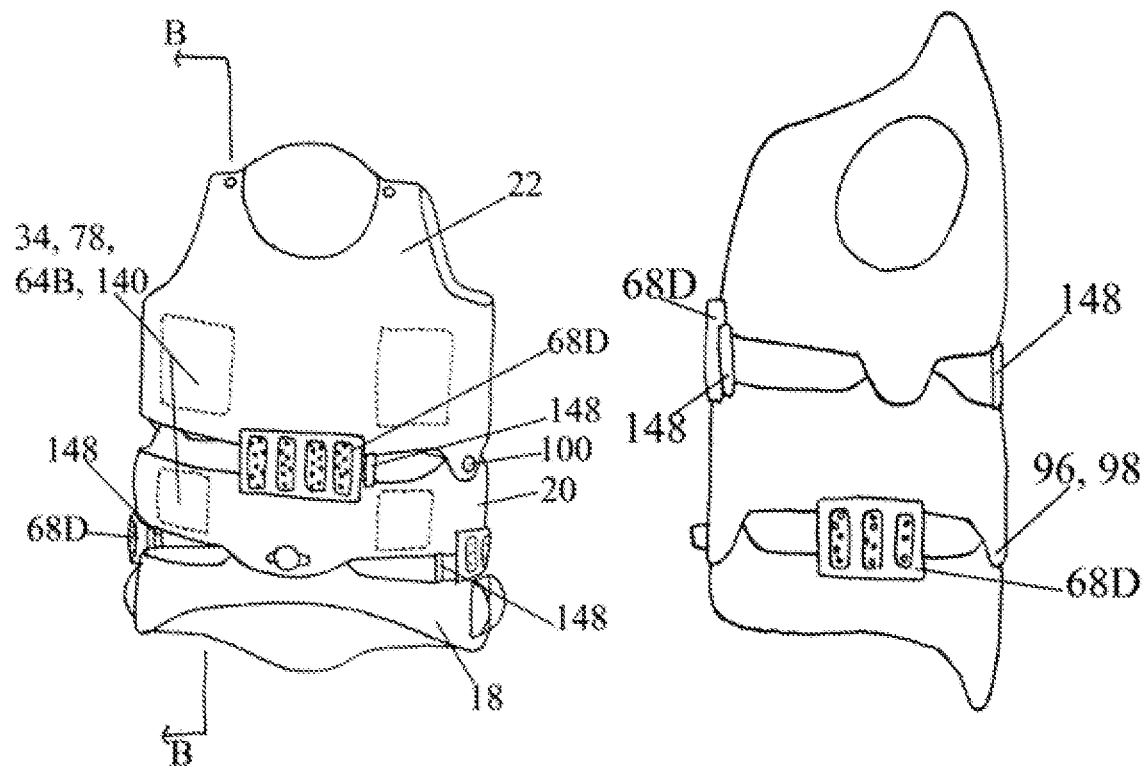
FIG. 18A  FIG. 18B
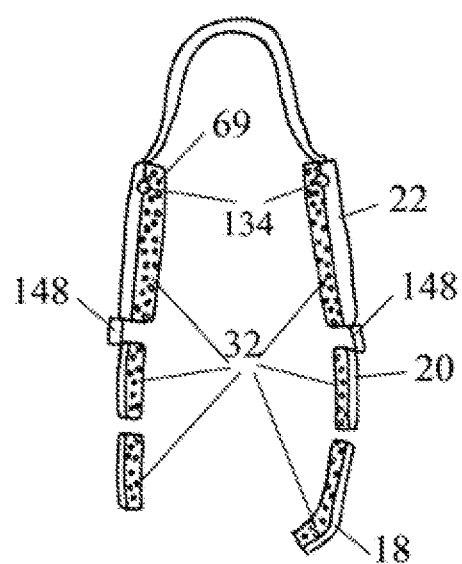
FIG. 18C

ROBOTIC MOBILITY DEVICE AND CONTROL

REFERENCE TO RELATED APPLICATIONS

This is a divisional application of U.S. patent application Ser. No. 15/472,662 which was filed on Mar. 29, 2017, which claimed priority under 35 U.S.C. § 119(e) to Provisional Patent Application No. 62/319,791 filed Apr. 8, 2016.

FIELD OF THE INVENTION

The present invention generally relates to techniques for supplementing relative movement between two or more substantially rigid biological skeletal members, such as limbs, that are coupled at a biological joint and in particular to a human exoskeleton that includes frame members and associated rigidity control devices.

BACKGROUND OF THE INVENTION

Robotics has been developed to assist people to walk. Current exoskeleton systems require a walking aid to function. Moreover, the person using the exoskeleton has limited control of such systems and thus the user's mobility and range are restricted.

SUMMARY OF THE INVENTION

The present invention is directed to a bipedal, powered ambulatory robot for mobility assistance and to ambulation control. The ambulatory robot is capable of consistent dynamic ambulation with high energy efficiency, balance control, fall prevention, interfere avoidance with surround static, moving objects, and collaboration with other human activities. The robot uses a cable posture adjustment system that connects frame members and responds to muscular functions. For human bipedal ambulation, movement rules are established and standard posture data are created as reference data-pool with optimized postures with calculated static and dynamic overturn capacity. The robotic controls implement strategic logistics processes to achieve mobility assistance for a person, including: calibration, distance/location measurements, path selection, and posture selection for unavoidable contact force input. The robot has a plurality of node control units that are interconnected by node control network. With the present invention, a person can maneuver and perform bipedal ambulatory movements (walk) without having to hold onto a cane, walker or other similar handheld implement.

The present invention is based in part on the development of frame members (or elements) configured to be coupled to appendages, limbs, and other parts of the human body to form a powered operated exoskeleton. Each frame member preferably operates in conjunction with a rigidity control device structured as a bead-filled, air-tight compartment that is in communication with a gaseous vacuum source. When gas is removed from this air-tight compartment, the compartment collapses to modify the rigidity of the associated frame member which can be configured as light weight shell-like structures contoured to various parts of the body in part of assistance. In a preferred embodiment, the frame member and rigidity control device are constructed as an integral assembly consisting of the frame member with the bead-filled, air-tight compartment formed within the frame member. In addition, the source of vacuum can be an air-tight vacuum chamber that is also formed within the frame member. The frame members are attached to the body with adjustable straps, hook and loop ties (VELCRO) and the like. For limbs, the frame members can be fabricated as a hollow tube structure that can be worn.

In one aspect, the invention is directed to a robotic mobility assistant device, which is adapted to supplement relative movement between at least two substantially rigid biological skeletal members coupled at a biological joint of a user, the biological joint being rotatable around multiple mutually perpendicular axes intersecting at a center of the biological joint, that includes:

(a) first and second frame members that are configured to be coupled to the at least two substantially rigid biological skeletal members;

(b) a mechanical joint means for coupling the first and second frame members, the mechanical joint device means defining a center of relative rotation of the first and second frame members about multiple mutually perpendicular axes, the center of relative rotation of the frame members being displaced from outer surfaces of the skeletal members to correspond in position with the center of the biological joint;

(c) means for coupling the first and second frame members;

(d) means for controlling the rigidity of the first frame member and which provides compression support to stop angle rotation between the first and second frame members; and (e) means for controlling the rigidity of the second frame member and which provides compression support to stop angle rotation between the first and second frame members.

In another aspect, the invention is directed to an apparatus for facilitating movement of a person's limb that includes:

a first frame member having a first outer surface and a first inner surface that has a first contour that matches the person's first limb and which is adapted to be secured to the first limb;

a first bead-filled compartment that is situated between the first limb and the first frame member;

means for removing gas from the first bead-filled compartment to decrease the volume within the compartment and compress beads together therein; and control means for removing gas from the first bead-filled compartment to facilitate movement of the first limb.

In another aspect, the invention is directed to a powered full-body, self-supporting exoskeleton, which is configurable to be worn by a person, and that includes:

(a) a plurality of first and second lower limb frame members configured to be coupled to the person's first and second legs wherein the first and second lower limb frame members include respective first and second bead-filled, air-tight compartments;

(b) a plurality of first and second mechanical joint means for coupling the plurality of first and second lower limb frame members;

(c) a plurality of third and fourth upper limb frame members configured to be coupled to the person's first and second arms wherein the third and fourth upper limb frame members include respective third and fourth bead-filled, air-tight compartments;

(d) a plurality of third and fourth mechanical joint means for coupling the plurality of first and second lower limb frame members;

(e) a plurality of fifth frame members configured to be coupled to the person's torso wherein one or more of the fifth limb frame members include respective one or more fifth bead-filled, air-tight compartments;

(f) a plurality of fifth mechanical joint means for coupling the fifth frame members; and (g) means for regulating the pressure inside the bead-filled air-tight compartments to manipulate the rigidity of the frame members to facilitate coordinated movement of the exoskeleton.

In a further aspect, the invention is directed to a method of operating a powered exoskeleton which is worn by a person that includes the steps of:

calibrating the powered exoskeleton to the user's individual physical characteristics;

monitoring the pressures at selected of parts of the powered exoskeleton to generate a plurality of pressure measurements that are indicative of the user's bodily anticipated movements, position and balance;

monitoring the environment surrounding the powered exoskeleton to generate a plurality of environmental readings that are indicative of potential obstacles; and controlling movement of the powered exoskeleton towards a target position by continuously activating selected actuators in response to the plurality of pressure measurements and plurality of environmental readings to facilitate movement along a selected path.

Features of the invention include: (1) A postural data-pool stored with calculated results of joints angle, joint relative coordinate, velocity and overturn load capacity, movement index, energy conservation level, statics and dynamics characteristics of specific user limbs length and weight. The calibrated posture data is used as initial values for the robotic mobility assistant device's bipedal ambulation control. (2) N-particles movement simulation, dynamic data, joint energy timing, and torsional capacity afford fluent bipedal ambulation and fall prevention. (3) An algorithm provides analysis capacity for calculating current balance state and predicting possible near future imbalanced states. The algorithm also implements warning and process to recover in the event of an emergency. (4) The robot is designed with vertical load carrying capacity and horizontal stability by posture configuration with torsional timing control cables providing lateral mobility to counter horizontal load impact. (5) Joints are connected to rigidity control devices (bead-filled vacuum compartments). Negative pressure causes the bead-filled structures to form passive rigid compression elements that stiffen the joints and prevents excessive rotational movement, at given angles, of the connected frames to supplement holding capacity of electric powered motors. (6) Air pump systems operate in coordination with a user's joint movements; they apply an air pressure difference in airtight vacuum chambers that are located inside the robotic device's frame member walls. (7) The spring sets and joint rotation lock are energy timed to and synchronized with the user's dynamic requirements so as to optimize energy conversion between elastic energy, kinetic energy and potential energy during motion. (8) Accumulated torsional spring energy, which is generated from a set of bipedal ambulation patterns, is a potential energy source, in addition to bending energy, further increase system efficiency. (9) Sensor systems which include, for example, inclinometer sensors, accelerometers, camera sensors, and infrared sensors apply vertical edges in the environment data. Information plus edge pressure sensors in the major joints, which are calibrated for gravitation, provide parallel and redundant information for vertical reference. (10) A flexible axial device reacts to natural biological knee and ankle joint movements to prevent stress damage from mechanical movement. (11) Interior pressure sensors monitor the user's initiated action and correlate the information with current dynamic energy timing to predict subsequent user movements. Real-time posture selection enables the robotic device to collaborate with the users' intent. (12) Using the current joint coordinate data 218, a user interface displays three dimension time-dependent actions through space time as an enveloped tunnel. In accordance with the path selection result, in the current environment data, executed upon user's confirmation. (13) The camera sensors, with the aid of computer-vision algorithm, recognize and memorize surrounding objects. The controls to predict a moving objects' trajectory and provides appropriate response times so as to avoid or optimize postures for inevitable impacts. (14) Applying infrared sensor and bipedal ambulatory recognition to identify other bipedal ambulatory objects in near environment for impact prediction and collaboration. (15) Measuring sensor input data from a given sequence calibration process and recording calibrated posture data 212 of robotic devices for specific users. (16) Node control network is used to execute and measure feedback for real-time mobile control. (17) N-particles algorithm is used to simulate, predict and monitor the real-time physics of the robotic device's structural system and of the other human bipedal ambulation activities in near surrounding. (18) Multiple processes on one or more CPU/GPU units or single chip microcomputer/controller units perform functions such as sensors calibration, next time-stepped simulation, map, path selection, postures selection, user communication interface, and node spring box control commands execution, and (19) Waist node computation unit monitors for emergency responses with audio warning, posture altitude lowering sequence, and posture balance recovering control which provides a process to assists user for soft landings.

BRIEF DESCRIPTION OF THE DRAWINGS

FIG. 3A is a static analysis model and FIG. 3B is a N-body analysis model;

FIGS. 9A and 9B illustrate torsional stability control cables;

FIG. 11A shows a flexible axis and rigidity control devices in the torso, FIG. 11B shows the rigidity control compression, FIG. 11C shows the rigidity control compression in stretched positioned and FIG. 11D shows the rigidity control compression in compressed position;

FIG. 17A shows a hip device and its degrees of rotation, FIG. 17B shows a hip pitch to hip roll connection, FIG. 17C shows a hip roll track, and FIG. 17D shows a hip roll;

FIGS. 18A, 18B and 18C shows a front, side and cross sectional views, respectively, of a waist and chest device;

DETAILED DESCRIPTION OF THE PREFERRED EMBODIMENTS

Figure 1:
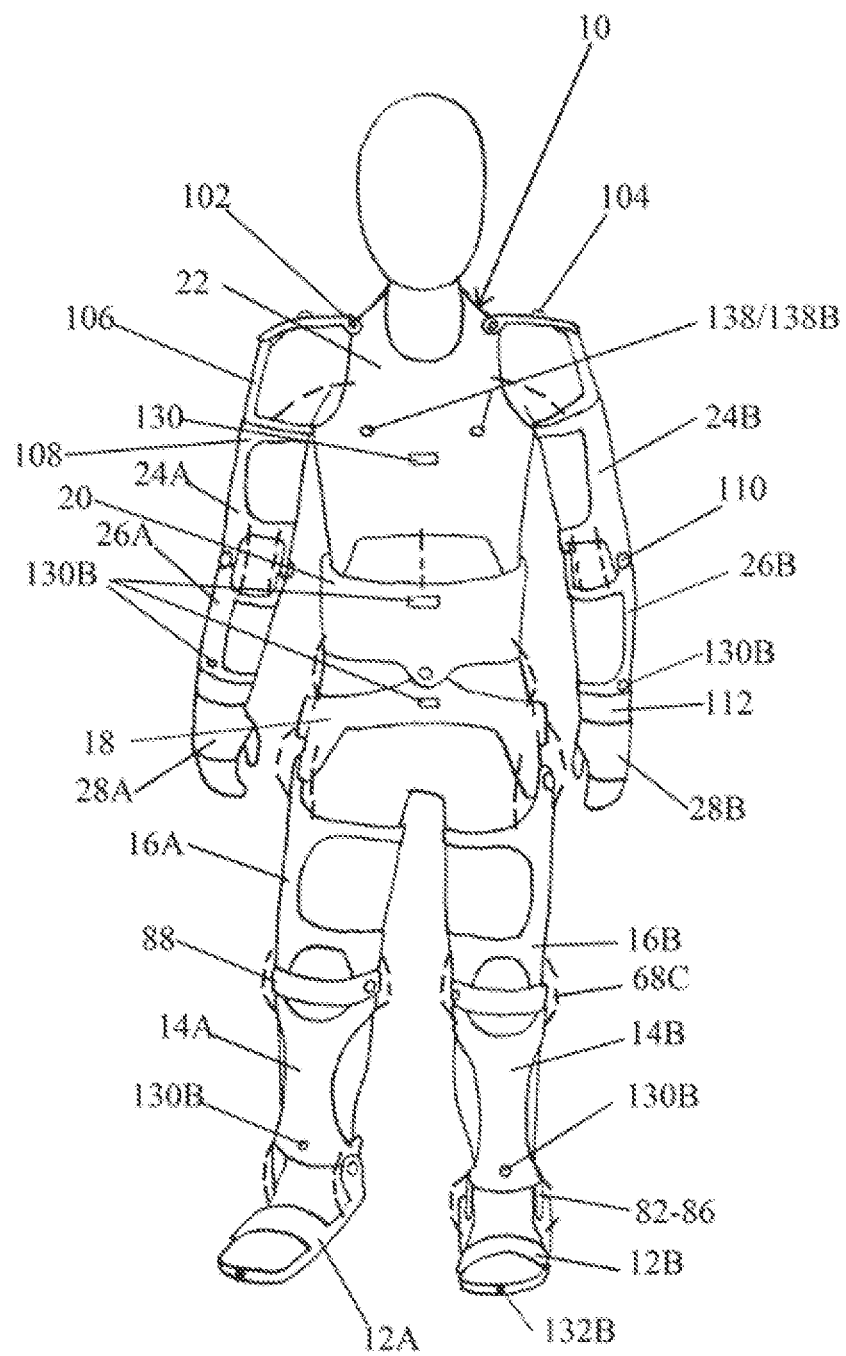
FIGS. 1 and 2 illustrate a robotic mobility assistant device.
Figure 2:
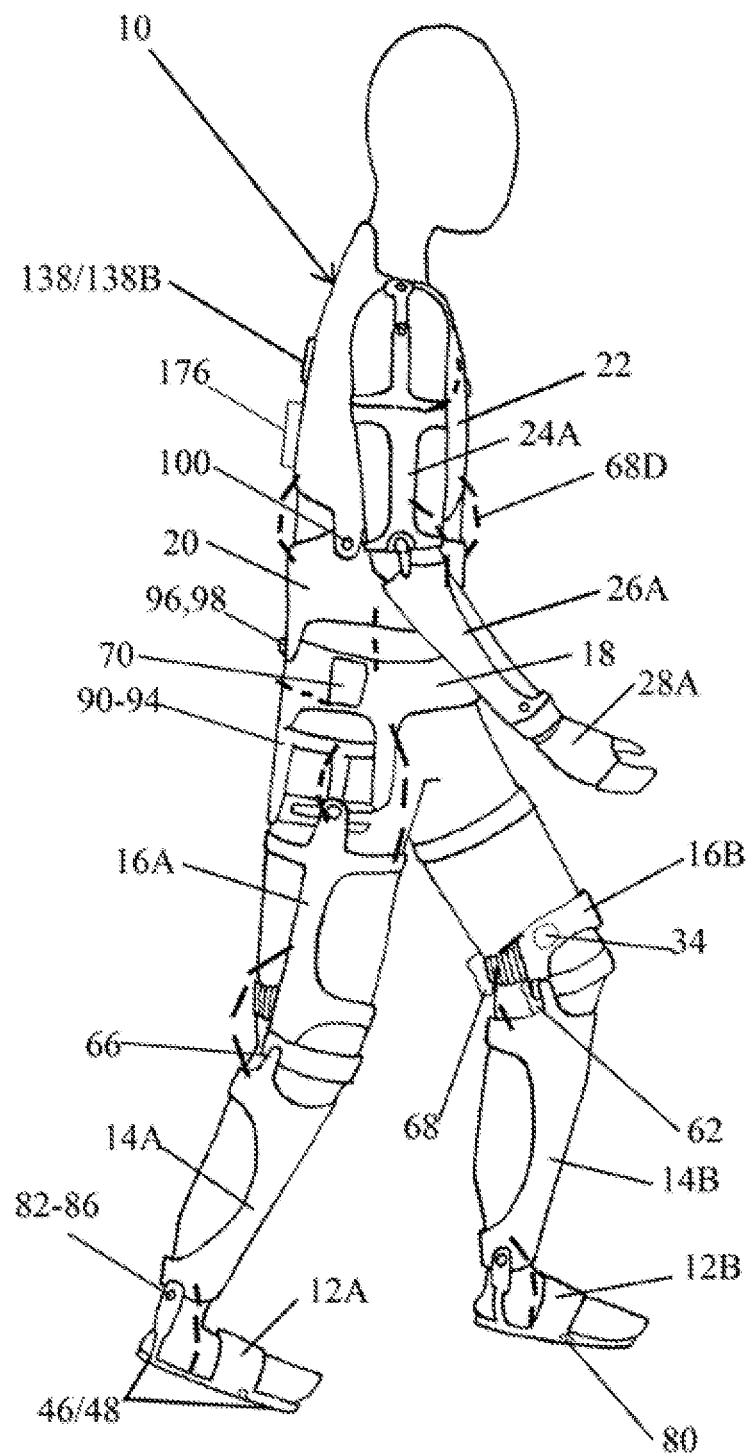

FIGS. 1 and 2 depict a robotic mobility assistant device, as worn by a person that includes a plurality of frame elements 10 to 28 that are interconnected by mechanical joints 80 to 112. Each joint device can exhibit different degrees of freedom, as further shown in FIG. 4, that are similar to a person's walking and moving degrees of freedom. The frame components include: foot frames 12A,12B, shin frames 14A,14B, thigh frames 16A,16B, hip base frame 18, abdomen frame 20, chest frame 22, upper arm frames 24A 24B, forearm frames 26A, 26B, and palm frames 28A,28B. The hip, abdomen, and chest frame form the torso or truck frames, the foot, shin, and thigh frames form the lower limb frames, and the upper arm, forearm and palm frames form the upper limb frames.

The frame elements 12-18 are constructed of materials that are sufficiently rigid to support the individual. Suitable materials include, for example, high strength, carbon fiber, metals such as aluminum alloys, fiberglass, and composites. The frames can be made of different materials depending on the strength demands. The frames are contoured to the individual user's body shape. Each frame is created through detailed structure analysis got given maximum overturning impact loads. Each frame is analyzed for carrying users' limbs with dynamic load demands plus gravitation load from a given maximum moving patterns. The frame elements are sized to accommodate the normal expansion and contraction of the body due to breathing, eating, and other muscular activities.

Figure 12A:
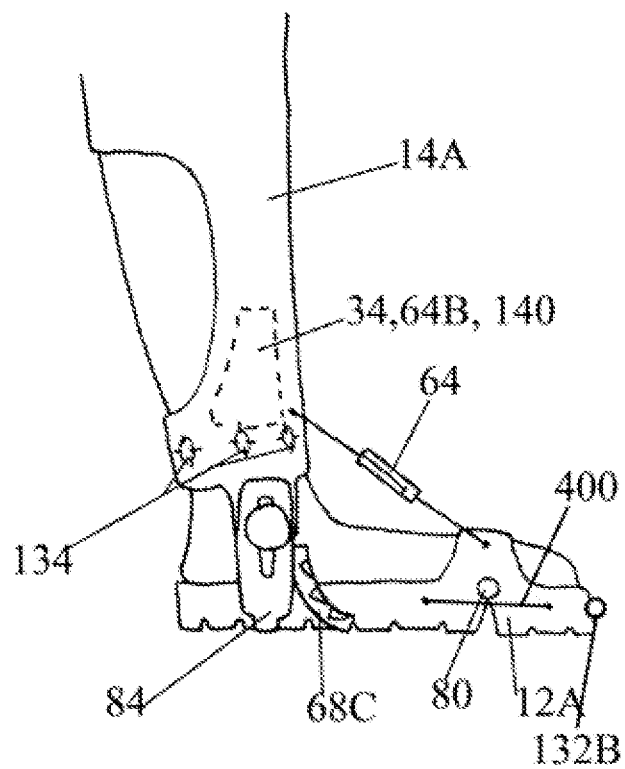
FIGS. 12A and 12B illustrate a toe and ankle device.
Figure 12B:
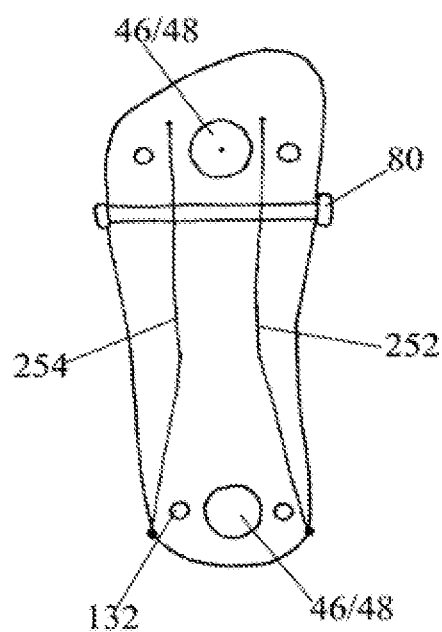
Figures 15A, 15B:
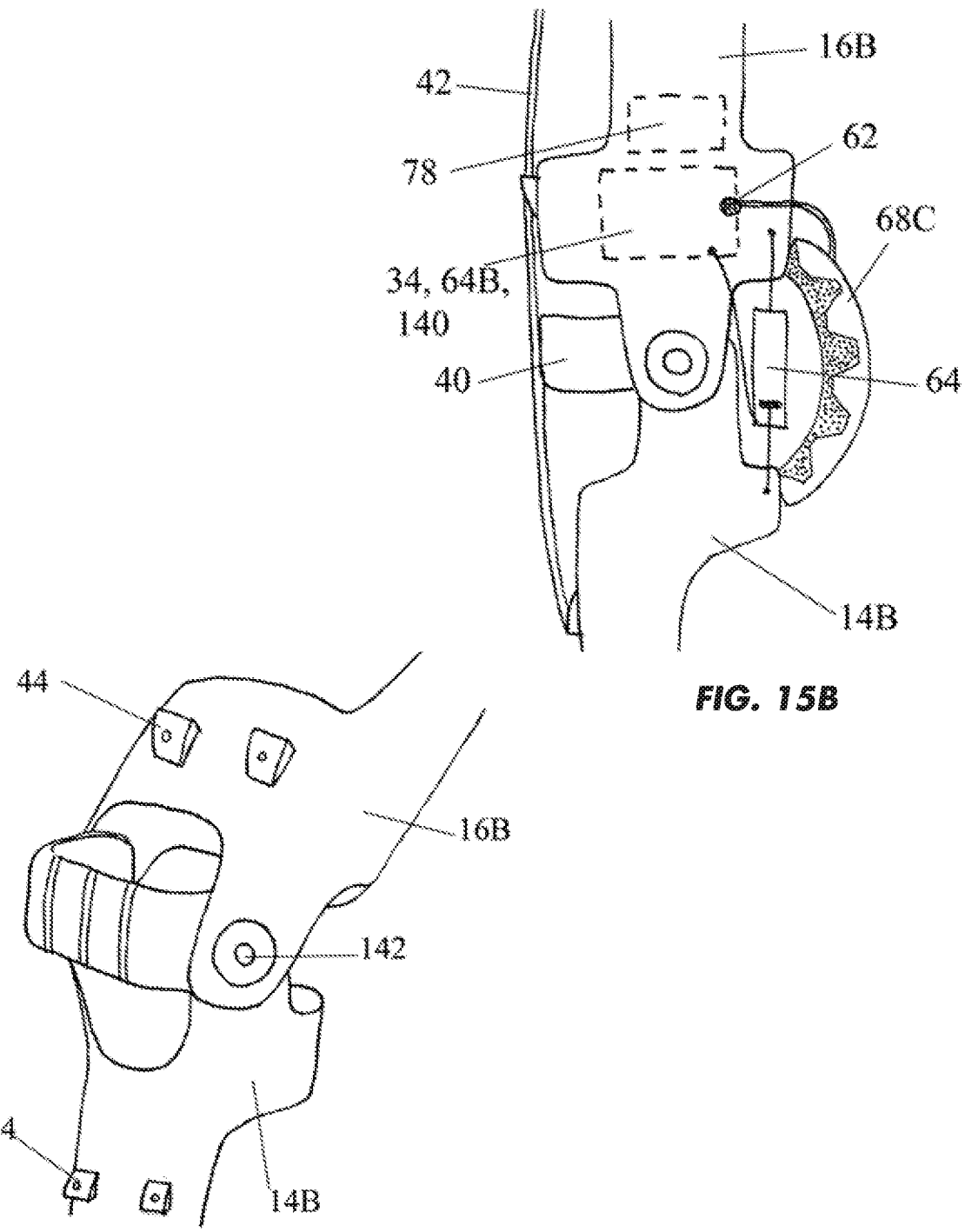
FIGS. 15A and 15B shows a knee device.
Figure 16B:
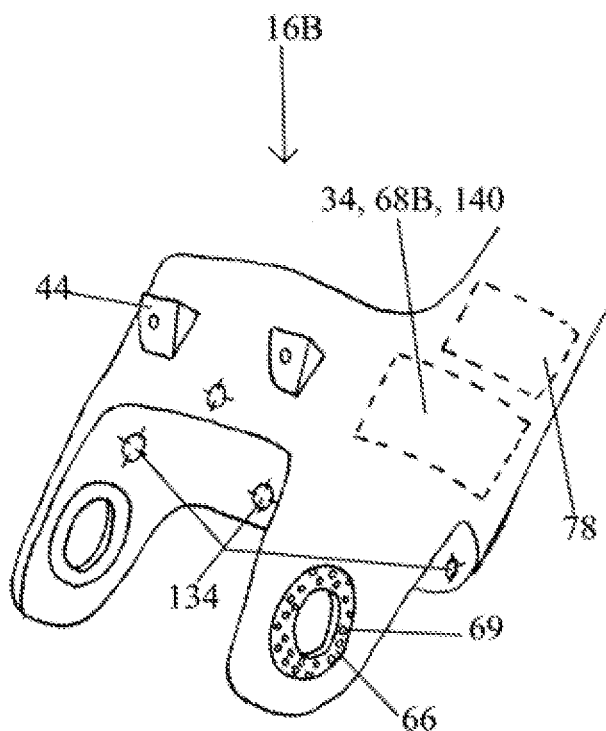
FIGS. 16A and 16B shows a knee device.
Figure 16A:
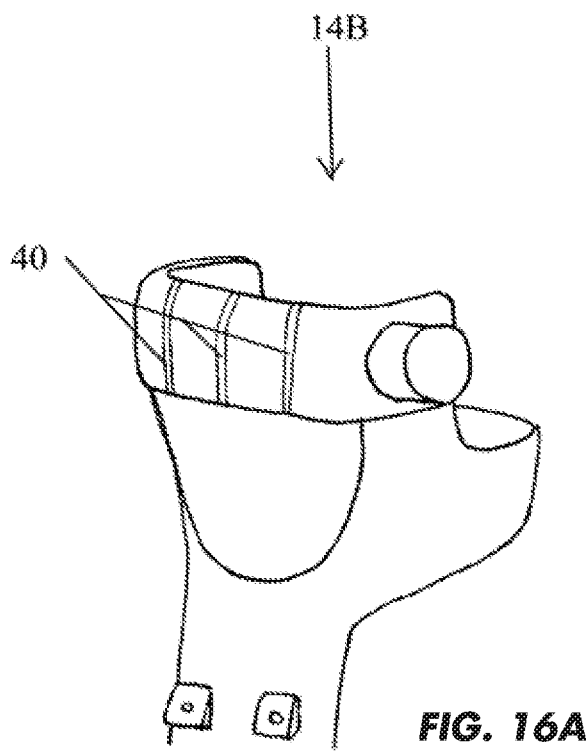

The robotic mobility assistant device 10 further includes components that function with the frame elements, including: length adjustment connections, bead-filled thickness adjustable compartments 32 (FIG. 18C), vacuum chamber 34 (FIG. 15B), mechanical joint connections, cable connectors 38 (FIG. 22B), cable saddles 40, cable tubes 42, cable anchor 44 (FIG. 15A,15B). The foot frame 12A,12B includes toe/heel electrical floor suction or magnetic device 46/48 (FIG. 12B).

As shown in FIGS. 1 and 2, associated with each frame is an air-tight compartment that is filled with beads. The compartment is made of flexible plastic, which is non-permeable to gases, and is filled with beads that are preferably made of non-deformable materials such as hard plastic. The size of the spherical-shaped beads can range from 0.5 to 1.5 mm and is preferably about 1 mm in diameter. Each compartment is filled with the beads so that the beads occupied about 90% of the volume. An individual air-tight compartment can be formed in a plastic pad that defines hollow air-tight compartment therein. The hollow pad preferably has the configuration of a thin bag. In this fashion, a plurality of such pads is worn in between the person and frame elements. In the case where individual pads are used, the frame elements must be sized according to accommodate the pads that are worn below the frame elements.

A preferred method of making the frame element and associated bead-filled, air-tight compartment is to incorporate the compartment into the frame. In this integrated design, a bead-filled layer is preferably situated on the inner surface that is adjacent to the person's body. The thickness of this bead-filled layer is preferably enough to withstand tensile motions without ripping, and sustain to resist dynamic forces and reduce unnecessary momentum.

Each air-tight compartment is in gaseous communication with a vacuum source such as a pump. As air is removed or "squeezed out" from the compartment by the vacuum, the compressive force causes the size of the compartment to contract as the beads are forced together. The compartment solidifies and become rigid to fit to the user's muscular contour. This feature will facilitate movement as the user approaches load taking conditions by avoiding small area stress concentrations between user's skin and frame interior wall.

Instead of being connected directly to a mechanical or electrical pump, another technique of creating a vacuum within the bead-filled compartment is to connect the bead-filled compartment to a vacuum chamber 34 that is also within the frame element. The vacuum chamber is maintain at a low pressure level and is connected via a valve and/or other gas regulating device. The vacuum chamber serves as a vacuum storage or reservoir for the bead-filled compartment. In this fashion, when vacuum is need, the valve is opened and gas is removed from the bead-filled compartment. The vacuum chamber in turn can be connected to a pump to re-establish the vacuum therein as needed.

Thus, in one embodiment the frame walls can be constructed with hollow structures within the interior frame to for forming the bead-filled compartment and the vacuum chamber 34 (FIG. 11A). Moreover, this method of construction reduces the weight of the frames and therefore additional hollow structures can be formed.

In one embodiment, the air pressure is preserved by rigidity control devices 68, 68B to 68E (FIGS. 10,11A,11B)

when in joint rigidity adjustments. The source of the vacuum is produced by manual 64 (FIG. 12A) operations during user joints' movements and supplement by electric air pumped 64B.

Figure 13A:
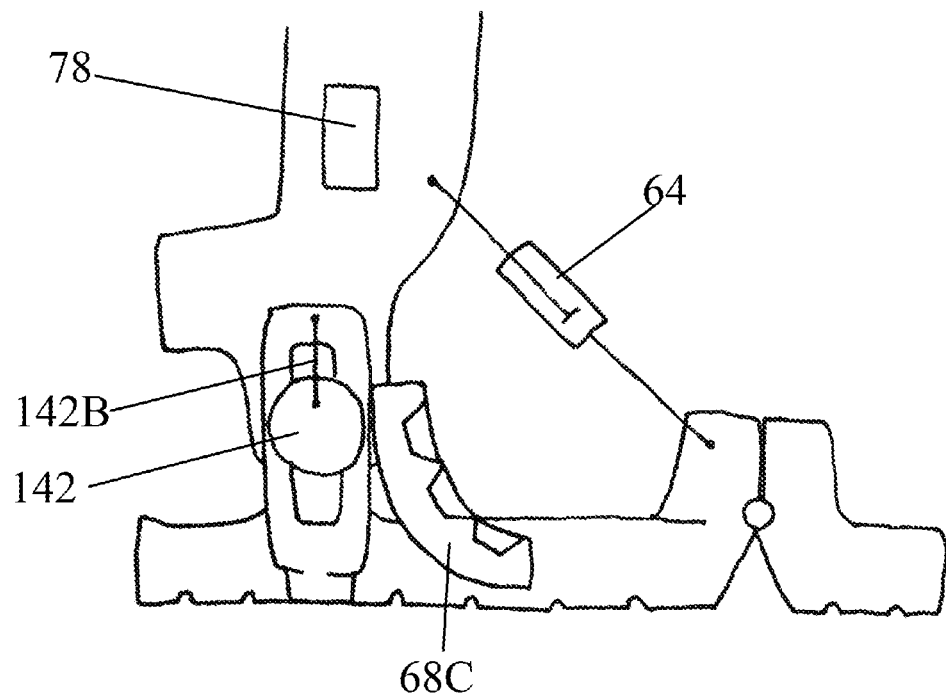
FIG. 13A shows a toe and ankle device.
Figures 13B, 13C:
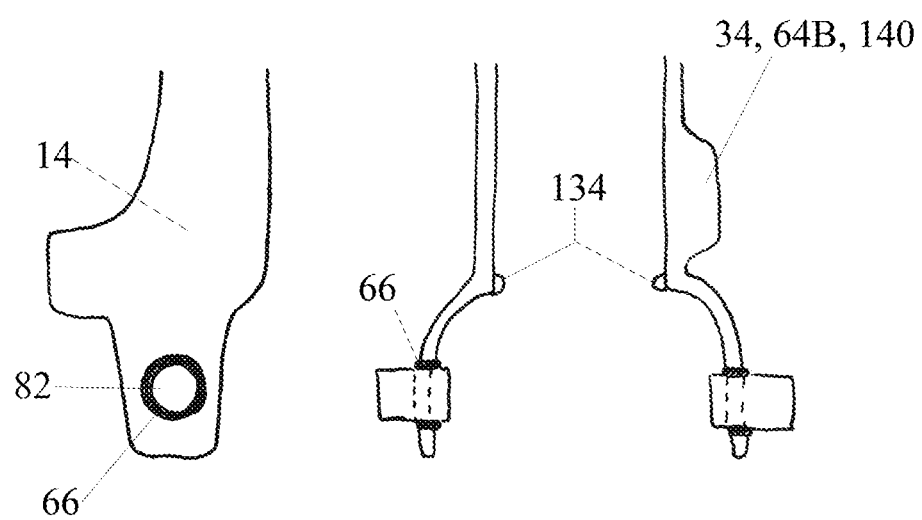
FIG. 13B shows the side view of the shin frame connection and FIG. 13C shows the section view of the shin frame.
Figure 14A:
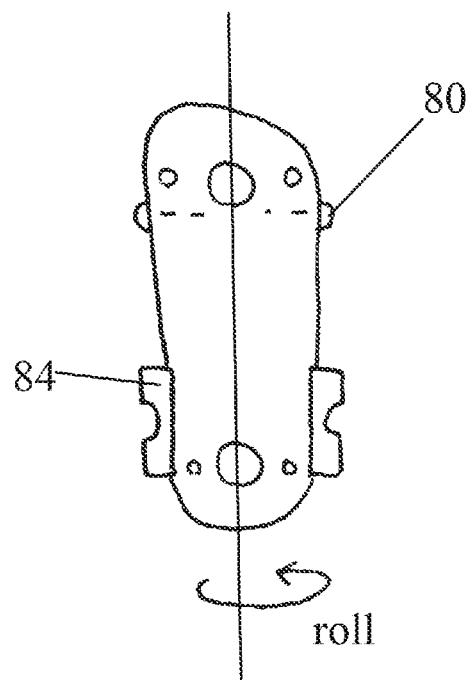
FIGS. 14A and 14B show degrees of freedom for the toe and ankle device with FIG. 14A illustrating space to roll and FIG. 14B illustrating ankle yaw walls.
Figure 14B:
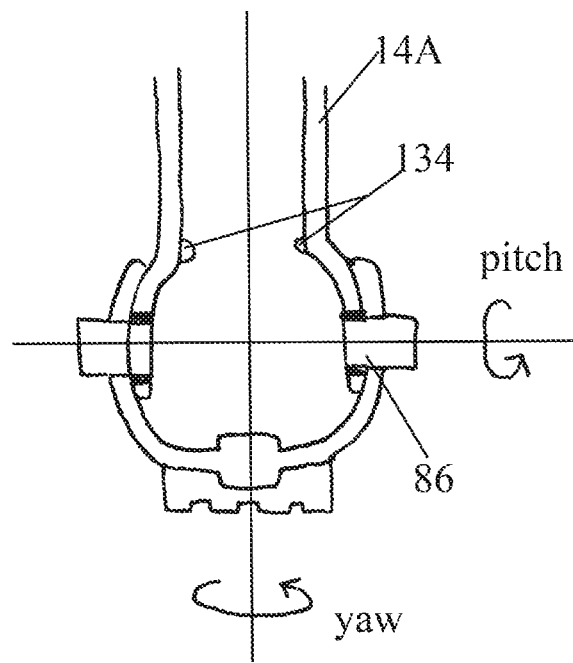
Figures 19A, 19B, 19C:
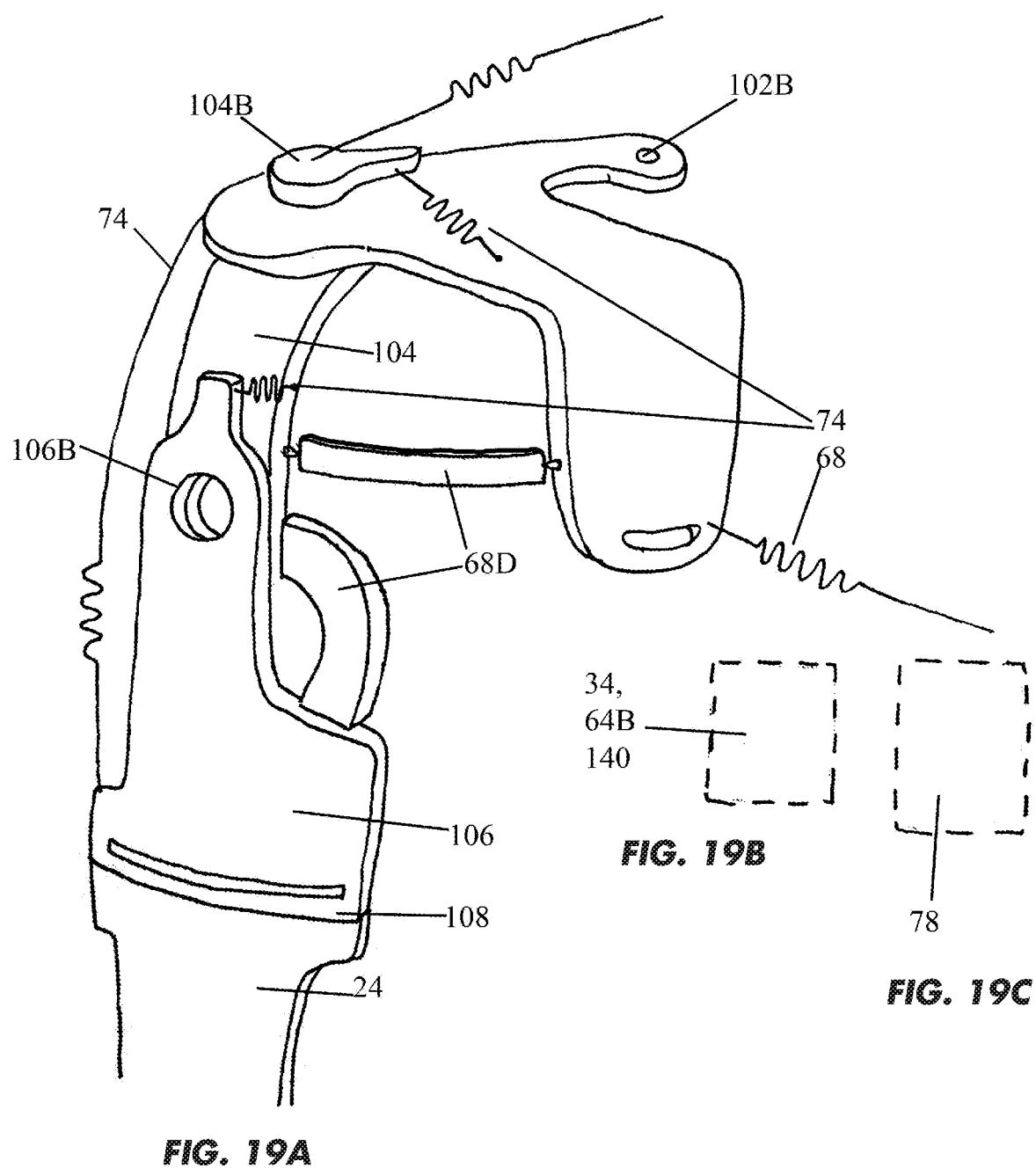
FIG. 19A shows a shoulder device.
FIG. 19B shows an airtight chamber and FIG. 19C shows node processing unit.
Figure 20:
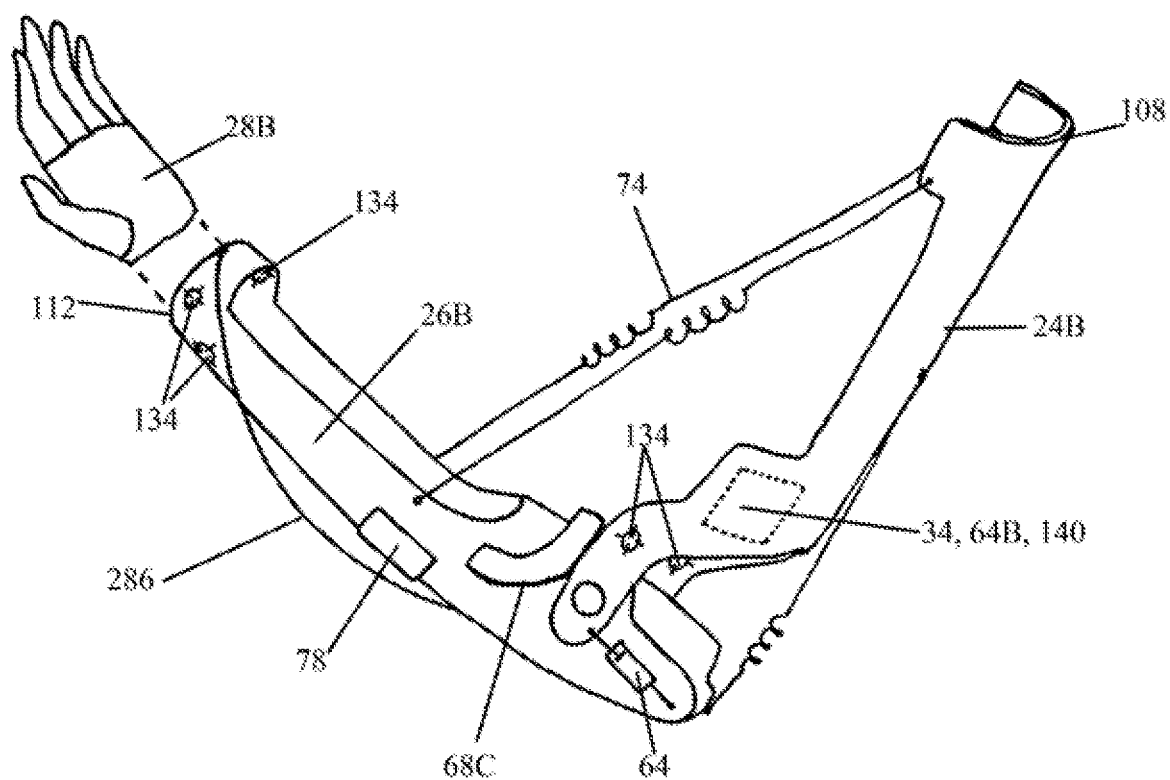
FIG. 20 shows an elbow and wrist device.

The mechanical joint devices include, for example: two toe pitch devices 80 (FIG. 12A,12B), two ankle devices 82-84 (FIG. 13A,13B,14), two knee devices 88 (FIG. 15A, 15B,16A,16B), two hip devices 90, 94 (FIG. 17A,17B,17C), a waist device 96, 98, one chest device 100 (FIG. 18A,18B, 18C), two shoulder devices 102-106, two upper arm yaw devices 108 (FIG. 19), two elbow devices 110, two wrist devices 112 (FIG. 20). The mechanical joints 80 to 112 provide flexibility that allows the device and user's joints' to move in a coordinated way.

Figure 31:
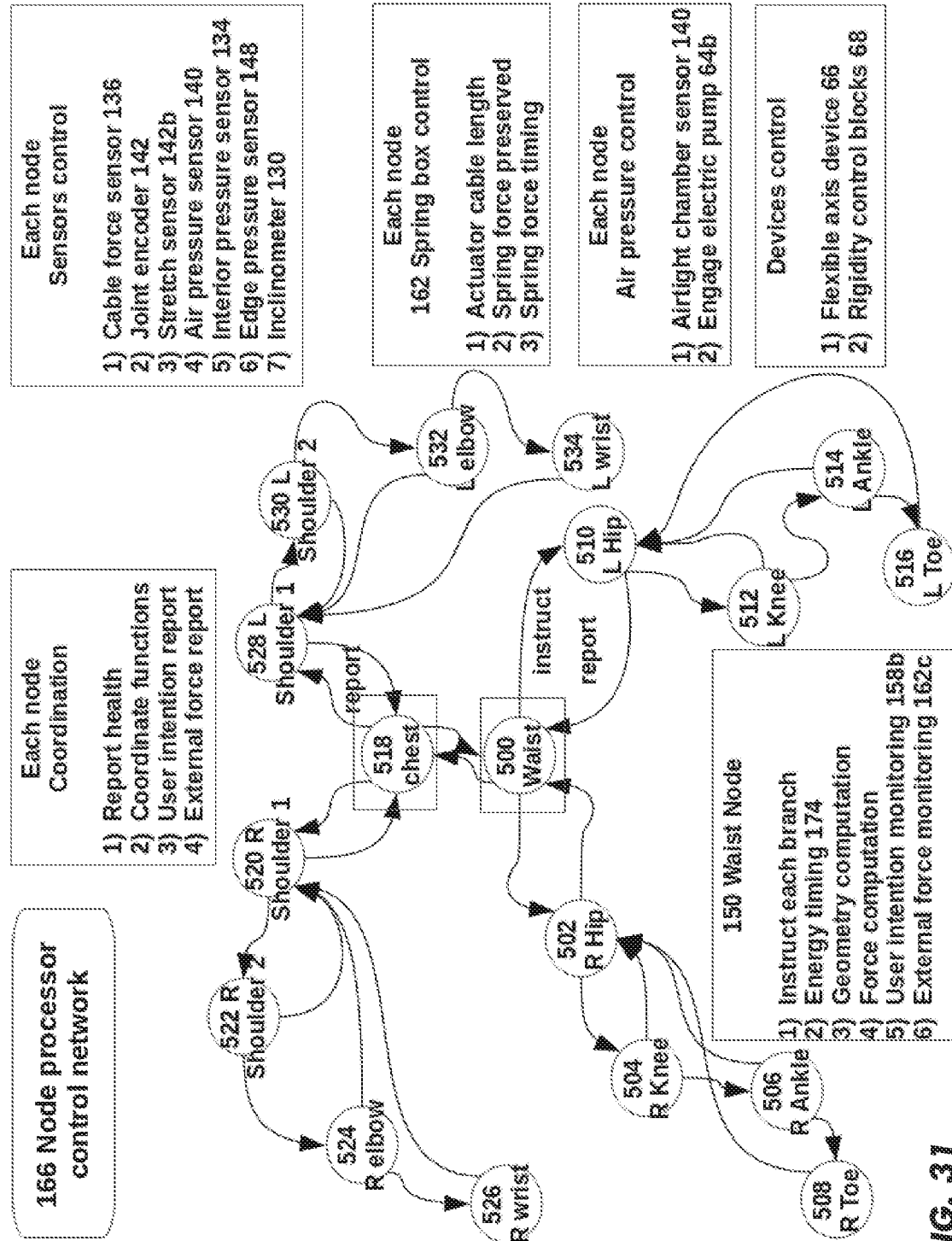
FIG. 31 is a schematic of node processor control network.

Each mechanical joint device includes multiple set of bend cables 400-464 (FIGS. 24 to 27C), flexible axis devices 66 (FIG. 10), rigidity control devices 68 (FIG. 10,11A,11B), air pumps 64 (FIG. 12A), cable anchors 44 (FIG. 15A), gravitation balance springs 74 (FIG. 21), cable force sensors 136 (FIG. 22B), bend cable actuators 72 (FIG. 22A), encoders for each extension shaft and journal 66 (FIG. 10), bend cable spring boxes 68 (FIG. 22A,22B), non-linear tensile spring pads 76 [FIG. 23], node processing units 78 500 to 534 (FIG. 31).

The sensors include, for example: inclinometer sensor 130, accelerometer 130b, sole pressure sensor 132, sole distance sensors 132b, interior pressure sensor 134 (FIG. 13B), cable force sensor 136 (FIG. 22B), stretch sensor 142b (FIG. 17A), sets of front and rare view camera sensors 138, infrared sensor 138b, air pressure sensor 140, encoder (extension shaft and journal) 142 (FIG. 17A), GPS global positioning system 144, magnetometer 146 and edge pressure sensors 148 (FIG. 18A,18B).

The robotic mobility assistant device 10 is equipped with sensor groups and calculation units, which predict unstable conditions in its early stage, makes corrections to stabilize posture 160 (FIG. 35), and balance external impact with prompt and precise posture adjustment through node control network 198b (FIG. 31). Control techniques are described in FIGS. 28 to 37. The controls include a central control 178 and process units (FIG. 28) are further described in FIGS. 29 to 38.

The robotic mobility assistant device 10 illustrates a full-body exoskeleton that is suited for persons who have limited use of their arms and legs such as a quadriplegic. For partially disabled individuals, only portions of the exoskeleton are needed. For instance, a paraplegic may require only the torso, waist and leg frames.

In operation, once the exoskeleton or parts thereof are worn by or coupled to an individual, the control system directs the user through a sequence of calibration steps to adjust the exoskeleton to the user's specific range of mobilities.

Motion Simulation

Figure 3C:
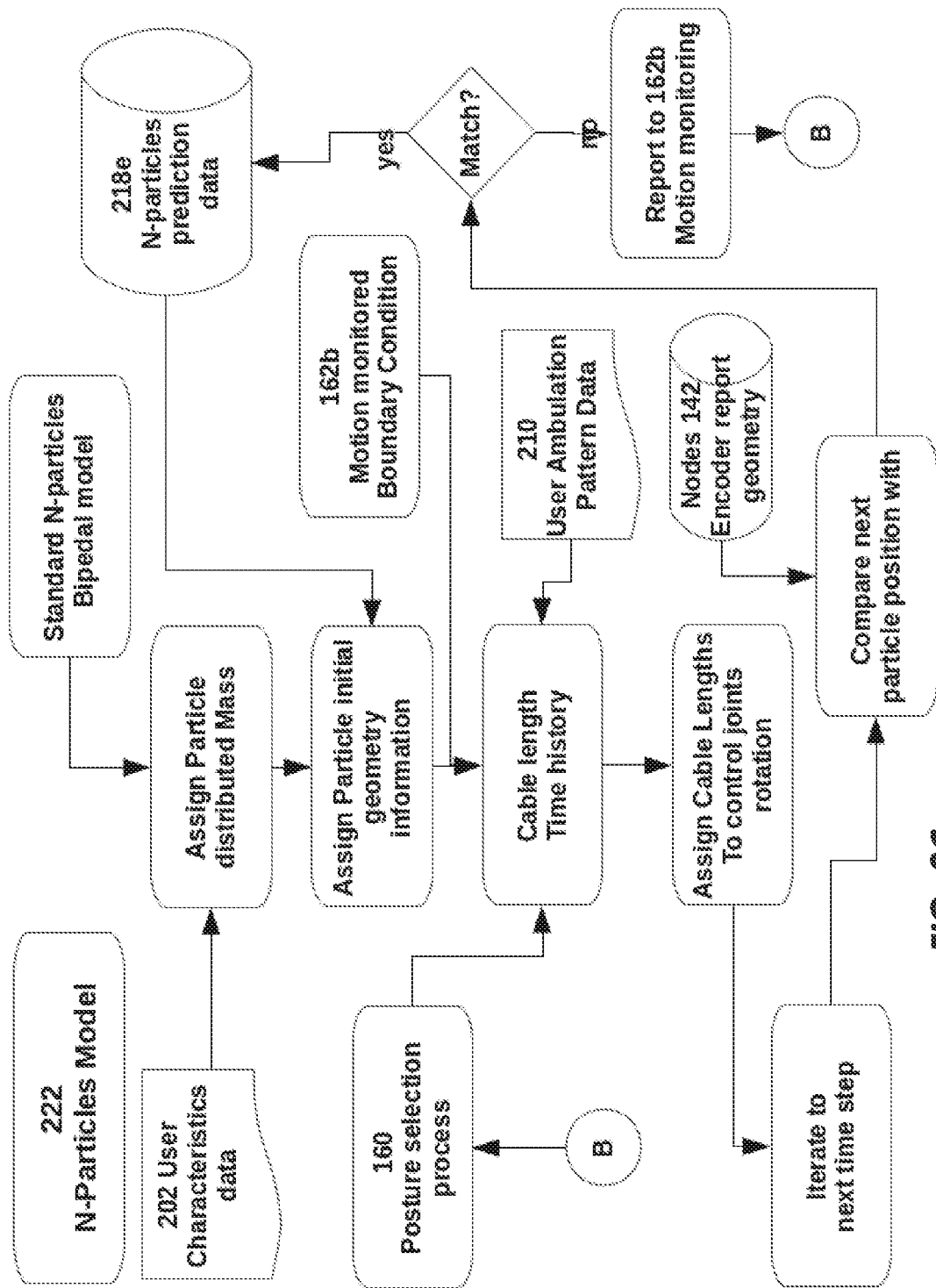
FIG. 3C is a process schematic of N-body analysis model.

Algorithms are employed to control the robotic assistant device. A method of developing the algorithms uses numerical simulation to simulate or model the movement of a person to create. FIGS. 3A,3B and 3C illustrate the methodology to simulate the physics conditions of the robotic mobility assistant device 10 (FIGS. 1 and 2) in motion. The simulation can be performed using standard numerical methods. A preferred technique is the complete conservative numerical method: N-particles analysis that employs numerical methodology to solve initial value problem of a non-linear N-body problem. The force in between particles is modeled in relation to the distance between the particles and in every time steps, the acceleration can be calculated by dividing the force by mass, thereby, solving the velocity and so forth the position of particles in the next time step.

Features of the present invention include: (1) using direct sensor information inputs to predict balance in the next time periods to allow adjustment commands to respond to external factors early and (2) the approach presents three dimensional physics, including z-axis yaw torsional effects at the feet that account for the missing stability controls in the prior art. Moreover, the same algorithm that is also used in predicting external other bipedal physics 218C. This capability allows the robotic mobility assistant device 10 to prepare for probable contact events in the real world environment with other moving bipedal objects. Furthermore, the predictions enable the device 10 to prepare its posture section process 160 (FIG. 35) to configuration for balance within the duration of possible impact. Besides using a Newtonian iteration method, other numerical approaches can be employed, such as non-linear simultaneous equation matrices' solutions, to take advantage of modern multi-core processor CPU/GPU 180 in parallel processing for performance gain.

The construction details of the invention model as shown in FIG. 3B is acquired from a scanned, true scale model, replaced by Nth particles 228 related to a center line 234 skeletal model 236; when in operation, sensor system units report each skeletal bones' 236 geometry, and the coordinate of each particles 228 are defined accordingly. The speed of each particle 228 is calculated by applying differences between coordinate data of the skeletal bones 236, at time increment.

Figure 4:
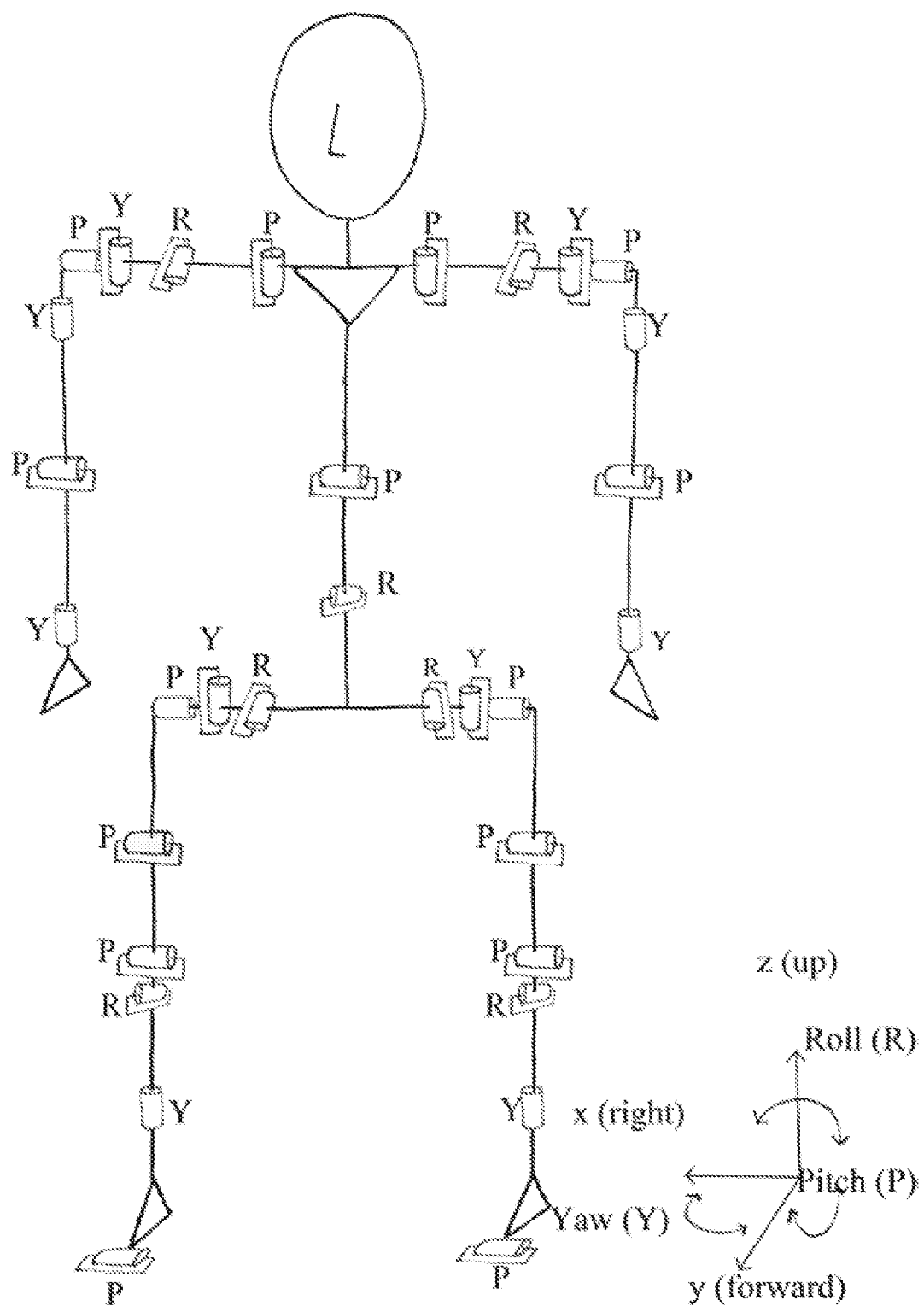
FIG. 4 is a joint degree of freedom schematic.

FIG. 4 is a joint degree of freedom schematic for the robotic mobility assistant device 10 (FIGS. 1 and 2). The local coordinate system is defined with its origin at the midpoint between hip joints. The x-axis is from origin points to right hip joint, the z axis upward against gravitation, and the y-axis is the cross product of z and x using the right hand rule. The rotation around z axis is yaw and rotation around y axis is roll and around x axis is pitch.

Figure 38:
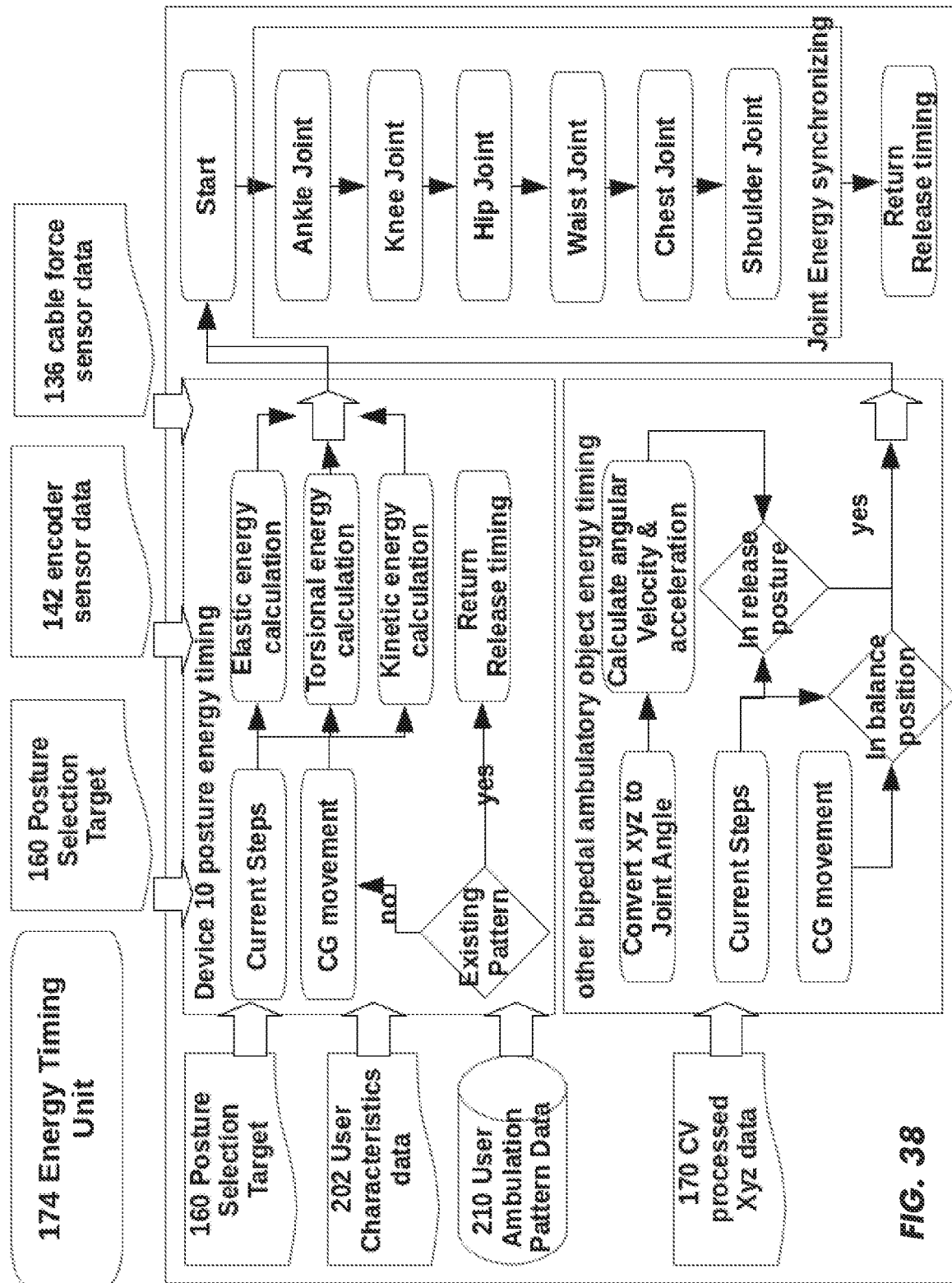
FIG. 38 is a process schematic of energy timing.

To create the model, a person's body mass is proportioned and assigned to multiple particle nodes 228. The links 230 in between the particles with a given force equations to keep constant distances, as rigid bones between particles. The connection between limbs such as shoulders, elbows, knees, ankles, etc. are arranged to simulate human joints' degree of freedom, connected by muscles 232. Each particle, assigned with initial local coordinates and velocities are acquired during calibration and in the sensors' geometry calculation in unit 150 (FIG. 33); the simulation is performed with small time increments for the subsequent seconds to obtain stability confirmation; in parallel, another one or more process take sensor inputs and compare them with the simulation results for differences to identify external force. The N-particles analysis process unit 168 include functions such as activation of actuators given by the postures selection unit 160 in accordance with rules of ambulation and attitude 204 and energy timing 174 (FIG. 38). The verified differences between simulation and real-time geometry sensor readouts are assessed to determine if they are caused by unknown force inputs, by motor, and actuator effort errors; the results are sent to waist node 500 (FIGS. 31,33) as external force condition for remediable adjustments.

Figure 5:
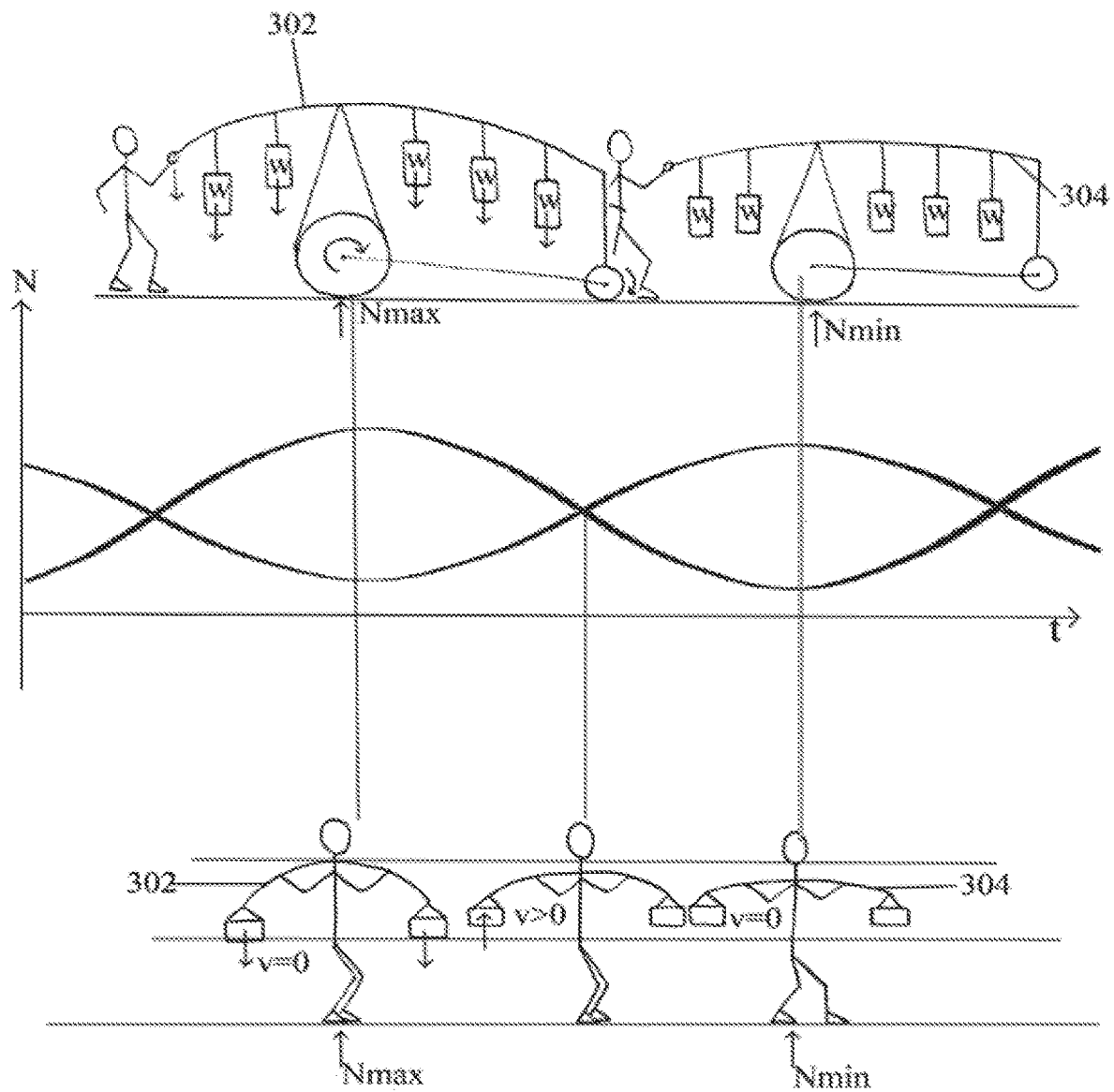
FIG. 5 is a schematic example of energy conversion.

FIG. 5 is a schematic that illustrates different energy conversions in existing activities commonly observed in rural Asia. In both examples, a bamboo pole 302b is used to carry loads 304b on each side, and support at the center by a compression element, either a vertical truss structure or by a human. To determine efficient practice, the user creates a vertical oscillation of the bamboo pole 302 by using the gravitation of the carried objects 304b. The system moves forward when the vertical reaction N acting on the compression element reaches minimum 304b. The system becomes rigid and passively holds joint activity, supporting the position when vertical reaction N reaches maximum. The user experiment oscillation of the system that optimizes the energy conversion in finishing the task.

Figure 6:
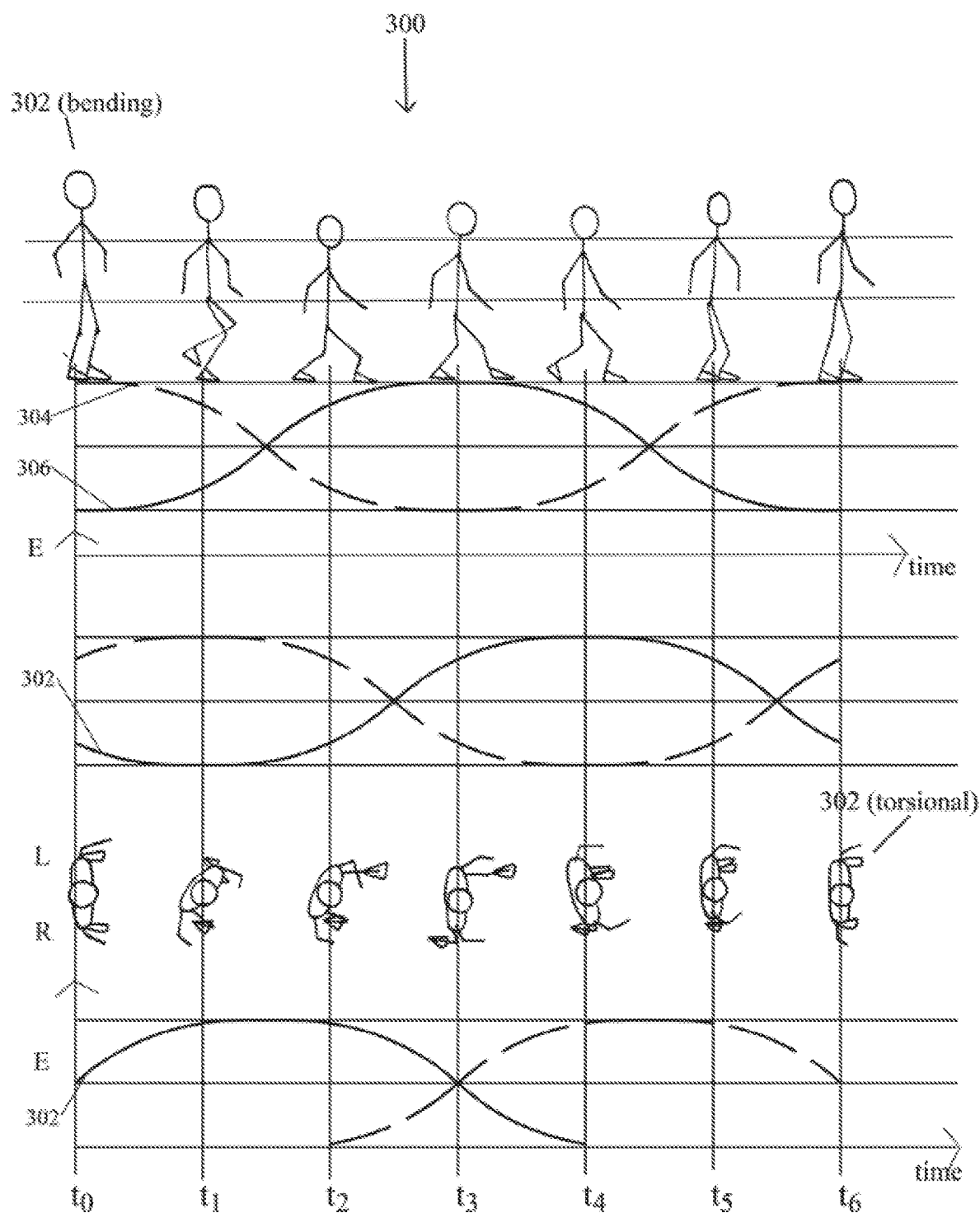
FIG. 6 is a schematic of energy conversion synchronization.

FIG. 6 is a schematic of energy conversion 300 and shows a side view of the robotic mobility assistant device's bipedal ambulation. The postures selected creates energy transfer from potential energy 304, by lowering elevation of center of mass to convert into elastic energy 302 that stores in the bent joint of the ankle, knee, and hip to generate the kinetic energy of speed in the device (t0 to t2). After the middle of the transition (t3), the speed decreases with rising elevation, and the kinetic energy 306 and elastic energy 302 transfers back to potential energy 304 (t4 to t6). FIG. 6 also shows torsional elastic energy 302 store and release in exchange with kinetic energy 306. At the beginning of the sequence (t0 to t1), the torso turns to move the gravity center closer to the right leg, and to elongate the right ankle-knee-hip with inward bend 254 (FIG. 9). As the elongate right torso twists 256 and the right shoulder-elbow-wrist outward bends 258, the lateral kinetics energy 306 transfers into torsional elastic energy 302 while rotational speed turns to zero, the left stepping starts (t2), the stored torsional elastic energy 302 transfers to rotational postural kinetic energy 306 (t2 to t3).

Figure 7A:
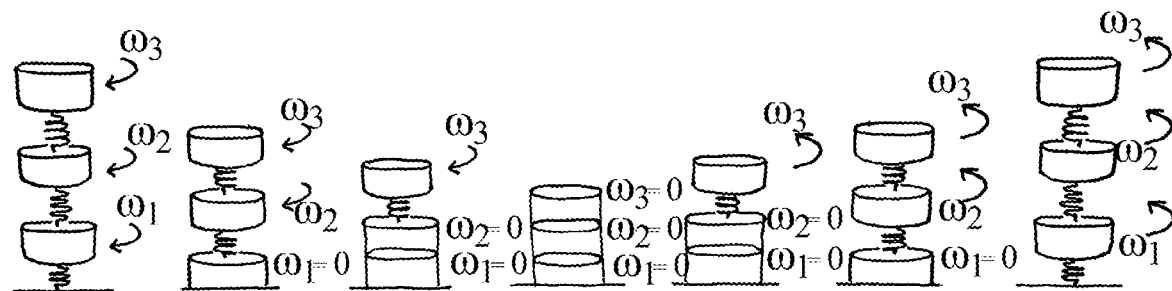
FIG. 7A is a schematic of torsional kinetic and elastic energy synchronized timing and FIG. 7B is a graph illustrating conceptual rotational velocity time history.
Figure 7B:
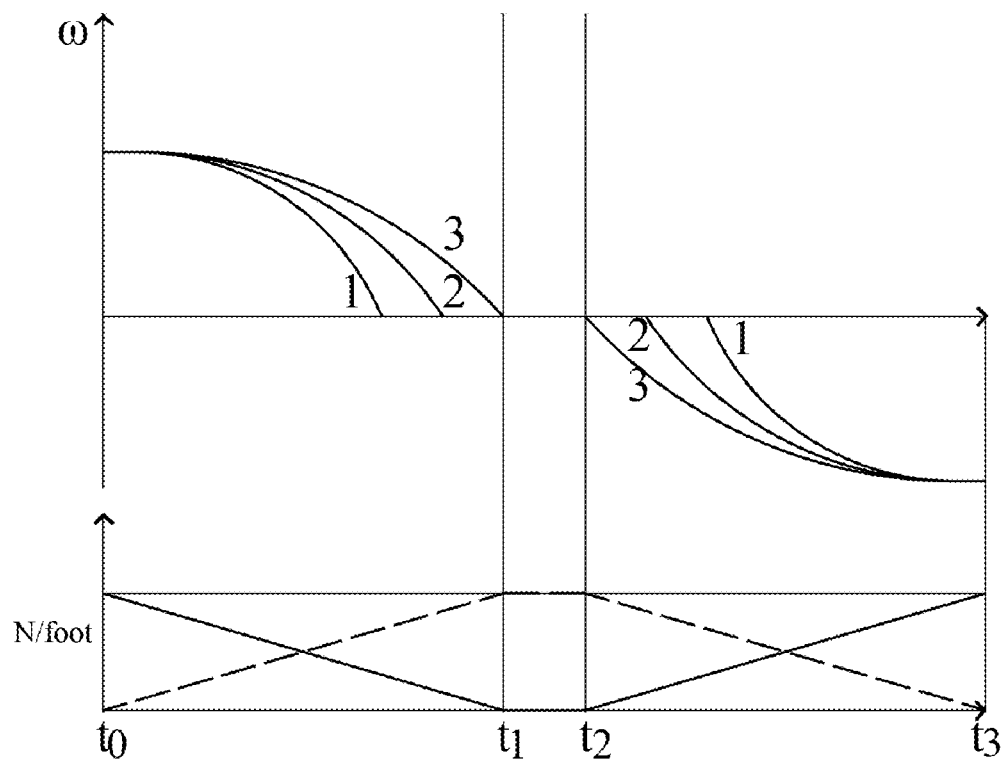
Figure 8A:
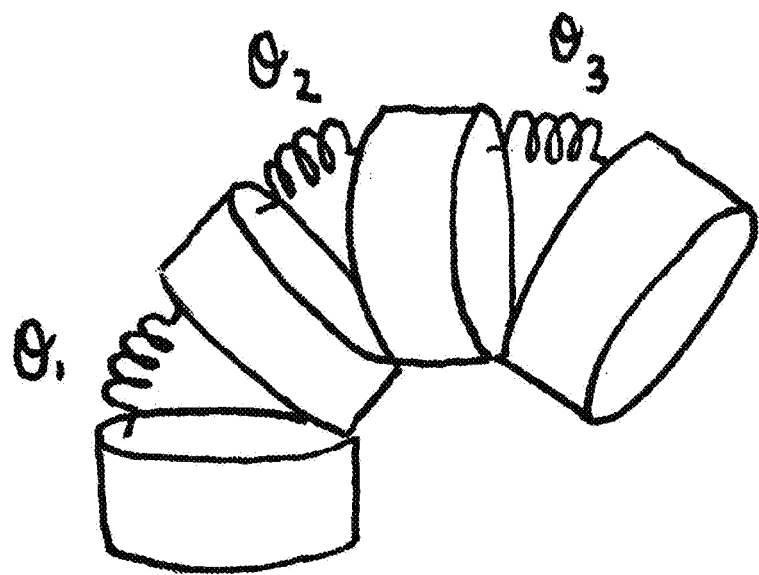
FIG. 8A is a schematic of bending kinetic and elastic energy synchronized timing and FIG. 8B is a graph illustrating bending angle between frame time history.
Figure 8B:
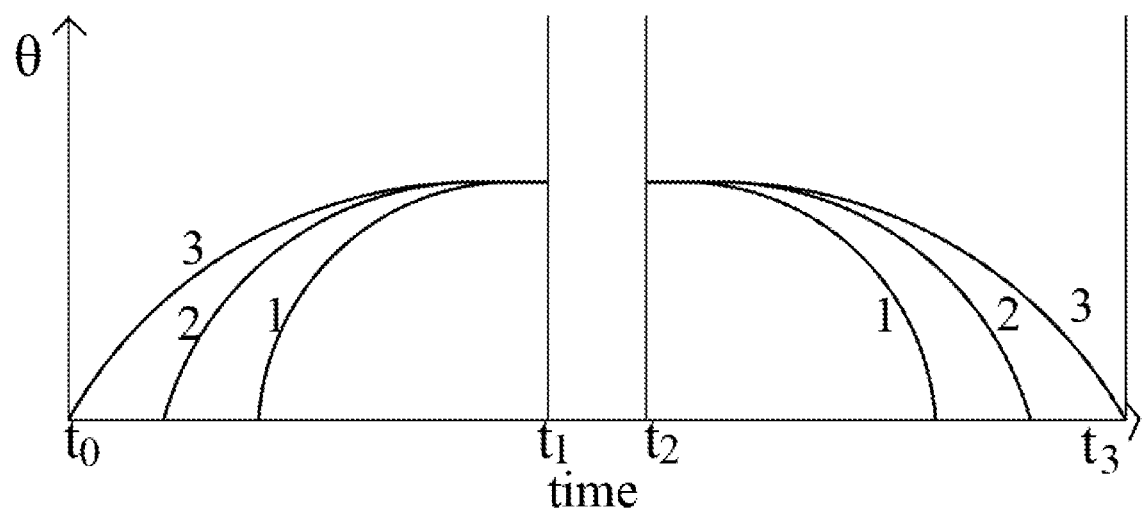

FIGS. 7A and 7B and 8A and 8B are the schematic illustrating torsional, bending, kinetic and elastic energy that synchronize timing 307. FIGS. 7A and 7B show a schematic of the sequence of conceptual rotational velocity time history from the maximum postural kinetic energy 306 (t0) to maximum torsional elastic energy (t1) while in FIGS. 8A and 8B show bending angles between frames' time history to maximize at the same time, storing parts of postural kinetic energy 306 into bending elastic energy 302. The stored elastic energies are then transferred back into postural kinetic energy 306 (t2 to t3). The present invention by applying these concept in energy timing calculation 174 (FIG. 38), reduces the power demands of actuators in initial maximum acceleration stage and reduces actuator holding torque requirements in the maximum deceleration stage.

Figure 30:
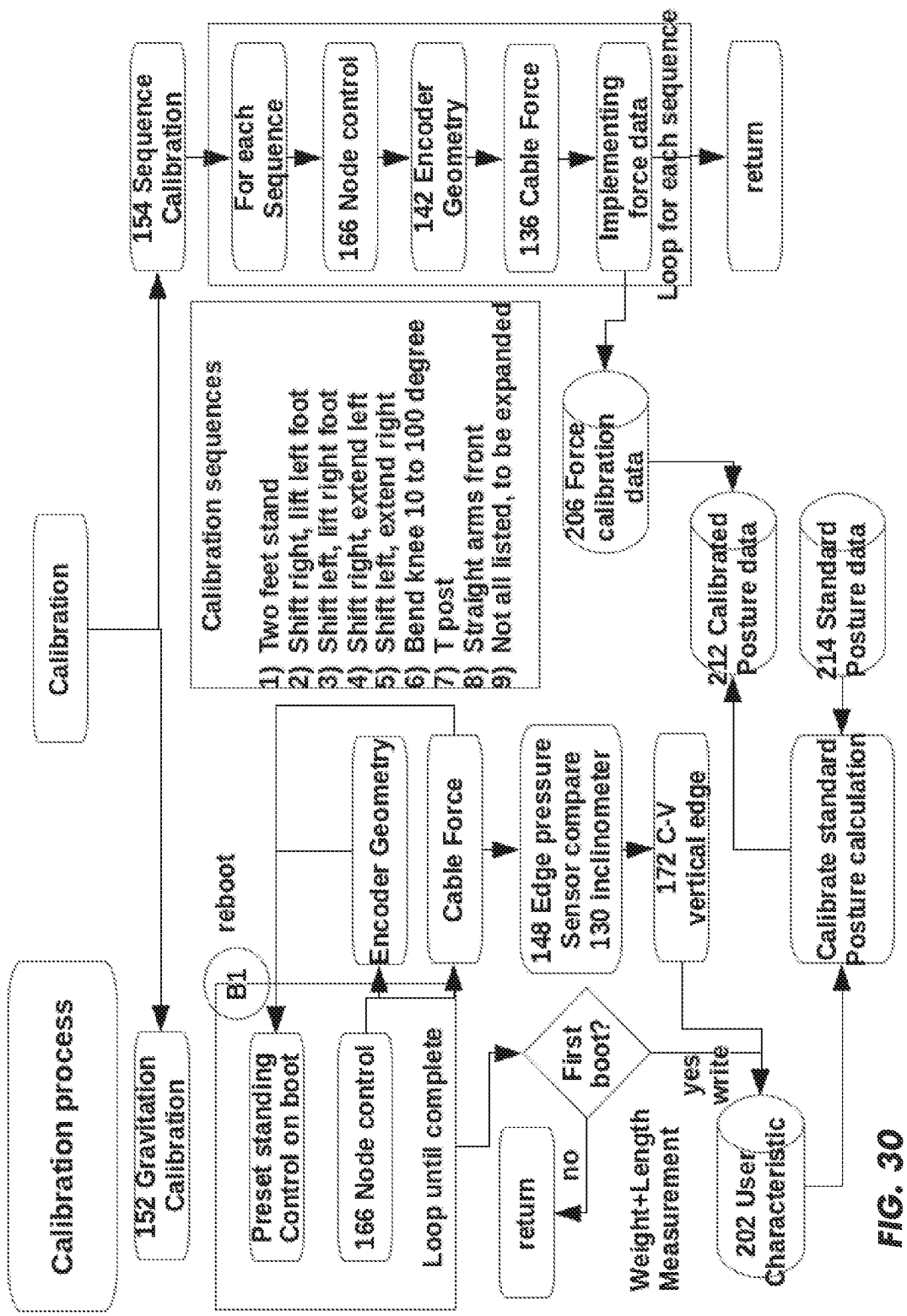
FIG. 30 is a process schematic of calibrating process.

There are multiple sets of physics springs in cable spring box 70 (FIG. 22B) that are used to store bending and torsional elastic energy 302. The cables are set to stabilize the device during postural variations and store the kinetic energy for later conversions. The left ankle-knee-hip inward bend cable path travels from outside of foot 12 through the backside of the shin 14 and up towards the outside of the knee cap 88 and through the inside of the thigh 16 then up from the back of the hip base 18 to top of the hip base and connects into the right side in the back of the abdomen frame 20. The torso turns left towards the left thigh 16, the torso mass' rotational inertia stretches the cable along this route through the hip base's 18 flexion of the thigh 16 around the hip's pitch device 88 and goes through the bending of the knee 88 and ankle 82 to become torque between the shin and foot through to the ankle's yaw 84. The length of the cable is set to users' lengths to prevent over bending, and guard maximum angles between frame elements to maintain structural stability. The calibrated lengths are generated with the sequence calibration process 154 (FIG. 30). The change of bending angles of these joints stretches the cable and stores elastic energy around joints such as the bending of knees, ankles, elbows, shoulders, hips and torso. The torsional elastic energy is stored around frames in yaw angles' variations. Examples include warping of the Hip-Knee-Ankle-Toe plane, twist of forearms, upper arms, and along the torso and shoulders.

With the present invention, the spring cables are designed to elongate with the rotation and torsional deformations during postural adjustments. The process of the energy timing unit 17 (FIG. 38) 4 calculates the energy conservation for the device. The elongation should reach maximum at the end of rotation and bending. The torsional twists or angle bending, relative between two or more frame elements adjacent to joints, stretches cables which are designed surrounding the joint with their limits of extension. Further stretching forces them into non-linear stress-strain behavior; meaning that they require exponential force increase to be used and creates less deformation. The sequence calibration (FIG. 30) will ensure the full strain to happen simultaneously, along multiple predetermined paths along multiple frames' elements. When the kinetic energy drives all joints against grounded horizontal reaction which provides a fixed point all displacements are zeroed, and at this end, the kinetic energy from all the frames' elements are converted and stored into bending and torsional elastic energy through cables. The velocity of all frames' elements decrease to zero. In the following event, the top elements are pushed by the contacted ground reaction upward through the connecting elements. One after the other uses their stored elastic energy. Those stored energy then releases and drives the frames' elements, sending the device into its next postural adjustment cycle.

The present invention uses theory of energy conversion through cables tension, and frames' elements in compression with advanced novel structural designs. It can also be present in other types of energy storage such as hydraulic drives, pneumatic systems, batteries, or air muscles. As long as the frames' kinetic and joints' elastic energy can be synchronized, the energy conversion could be provided by chemical energies, using combustion that powers large springs, for large energy conversions. The large elastic energy is available to generate more dynamic kinetic energy on demand.

Exoskeleton

FIGS. 9A and 9B illustrate a torsional stability control cable 250. A feature of the present invention includes increasing torso leg rotational stability without increasing frame structural thickness for strength. During bipedal ambulation, the rotational momentum around the z-axis of the torso needs to be balanced by friction between foot yaw against the contacting ground. This torsional moment is carried through ankle yaw, knee and result in the connection rotational resistance provided by hip base and waist devices. Two cables are used to balance the leg and torso connection. The left in bend leg cable path 282 travels from outside of foot 12B through inside of shin 14B and up to the front outside of knee cap 88 and through inside of thigh 16B and up from the back of hip base 18 to top of hip base and connect to the right side of the back of abdomen frame 20. The left out bend leg cable path 280 travels from inside of foot 12B through outside of shin 14B and up to front inside of knee cap 88 and through outside of thigh 16B and up from the back of hip base 18 to top of hip base and connect to the other side of the back of abdomen shell 20. A similar set of cables are used for the right leg.

With these two sets of lateral stabilize cables, the torso z-axis yaw rotation will tighten cable and constrain movement in margin of stability. The cable crossing around heel, knee and hip tightens when a leg increases in bending trend, and releases tension in the straighten position. The two cables 280, 282 are crossed in opposite paths and both tighten when ankle 82, knee 88 and hip 90 pitch in the bend position. The horizontal pulling force components of these two cables across knee are balanced, thus aiding in preventing knee from sideways buckling under torsion and compression.

In motion, the right leg out bend cable 252 works with cable 282 in helping resist torso z axis rotational momentum. The cables are for extreme conditions such as maximum length in force calibration 154 (FIG. 30), the force sensors reading is stored in force calibration baseline data 206 (FIG. 30) to measure balance margin.

Figure 10A:
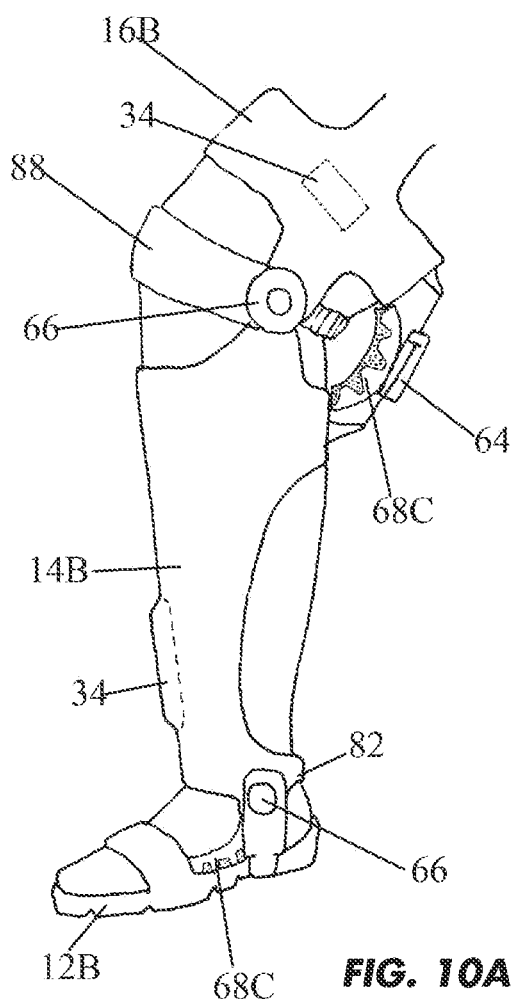
FIG. 10A illustrates a flexible axis and rigidity control device in the knee.
Figure 10B:
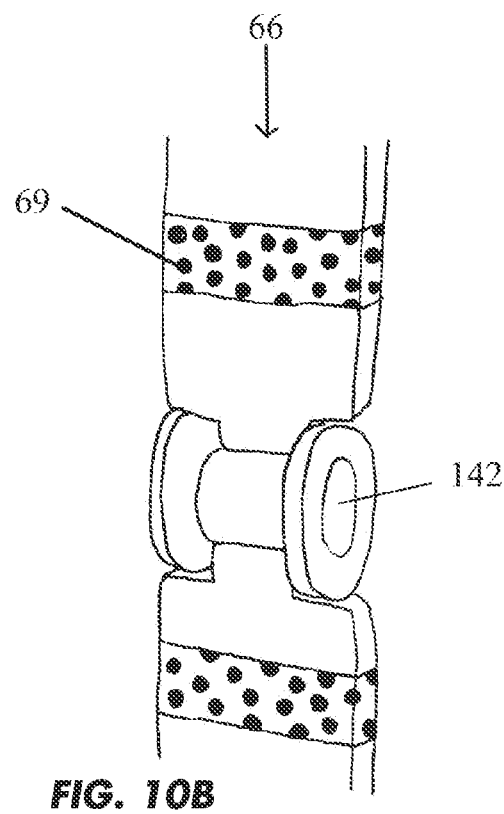
FIG. 10B shows a flexible axis device.
Figure 10C:
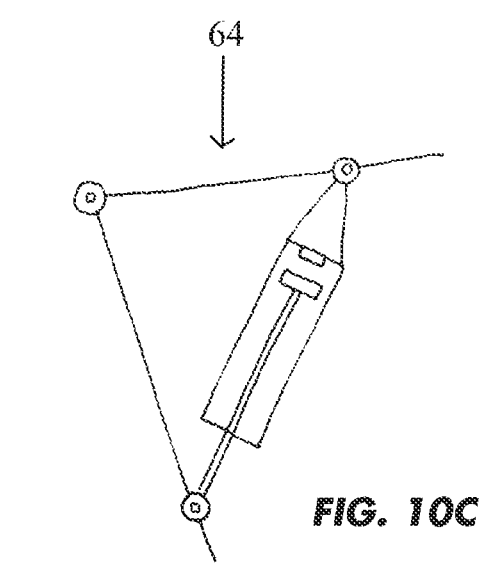
FIG. 10C shows an air pump.
Figure 10D:
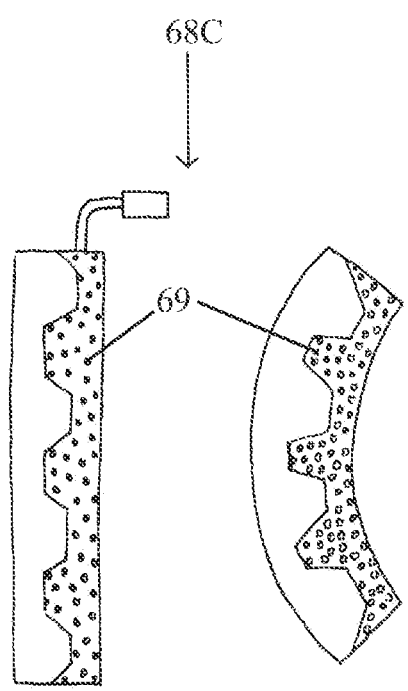
FIG. 10D shows a rigidity control bend block.

FIGS. 10A,B,C and D, 11A, 11B, 11C and 11D depict the flexible axis 66 and rigidity control devices 68 contained beads 69. A vacuum chamber 34 is configured in the frame wall and against the joint device. The negative/positive air pressure is provided through air pump 64 that is linked between frames and operate in joint movement; the membranes or walls of compartment 66,68 are made of an airtight flexible material such as silicon or rubber. The exterior contour or shape of the chamber changes with a person's natural joint range of motion, recorded in calibration process 152, 154 (FIG. 30). An electric valve 62 that is controlled by node spring box control 162 (FIG. 32) to remove air pressure, increasing rigidity, fix rotation center before all joint cable actuators 72 (FIG. 22A) fully loaded. After fully rigid state, when flexibility required, the electric valve 62 opens to pressurized vacuum compartment 66,68, fast release friction between beads 69 and provide maximum fluidity. The vacuum compartment is used in flexible axis device 66 in joint devices 88, 82, (FIGS. 13A,13B,14) 86 (FIG. 15B) and 110 (FIG. 20). For flexible axis device 66, an airtight compartment is positioned in between the thigh frame 16 and the journal of knee pitch device 88 and it provides the journal center line with a translation and angular variation capacity relative to thigh frame 16. The shin frame 14 provides firm connection to the shafts. Flexible axis device 66 provides the ability to cooperate with rocking behavior of bio skeleton in knee rotation.

The vacuum chamber 34 is also applied in rigidity control devices, such as compression pad 68B, rigidity control bend block 68C, rigidity control compression block A 68D and rigidity control compression block B 68E. These devices are differentiated by their shape variations. A compression pad is used to accommodate covering and compression support in large shape variation area such as gluteus maximus, adductor longus or deltopectoral groove. Rigidity control bend block 68c is used to provide bending angle stop at knee pitch 88, elbow pitch 110 inner bend (popliteal fossa) and ankle pitch to provide rigid support when needed. Rigidity control compression block A 68D is wider thereby permitting lateral shear deformation and provides compression support as needed. It is used in waist roll 96 on both sides, chest pitch 100 (FIGS. 18A,B) at front of chest. Rigidity control compression block A 68B provides large axial displacement to provide compression support, especially in providing compression resistance upper arm medially adduction and inward thigh adduction.

The robotic mobility assistant device is able to perform full load carrying, partial load carrying and balance control applications. Joints axis characteristics are stored in user characteristic data 202 and used in node spring box control 162. The present invention uses two rubber airtight membranes 66,68, air pump, vacuum chamber and digital controlled electric valve for differential air pressure in rigidity adjustment. It can also use hydraulic or electronic linear actuator and other mechanical apparatuses. A feature is to provide a variation of rotational axis to coordinate with user natural movement at joints between bio skeletons and to provide a light weight flexible shape compression block between frames across joint.

FIGS. 12A, 12B, 13A, 13B, 13C, 14A and 14B show toe and ankle devices which provide angular fixity and torsional capacity to the ankle joint and allow natural ankle rotation. The toe pitch device 80 consists of a pitch degree of freedom, provides 10 degrees of dorsiflexion and 5 degrees of plantar flexion. The plantar flexion provides pressure at the toes to generate friction to resist torsion as needed. One constant spring provides dorsiflexion to 5 degrees at all times and the connected ankle constant cable pulls it into plantar flexion when ankle pitch rotates to dorsiflexion range; two electrical floor suction devices 46 are at bottom of heel and phalanges; it activates for extra friction while ground condition required.

The ankle device 82 84 86 consist of a single component to allow for rotation in three degree of freedom to control its bending angles and load resisting capacities. The ankle yaw 84 provides yaw capacity. An elastic spring is installed to constrain yaw in (inversion) 5 degree and yaw out (eversion) 5 degree maximum. The side walls of the ankle yaw 84 are cylindrical to allow ankle roll 86 with constrain inversion 18 degree and eversion angle 5 degree maximum; a stretch sensor is installed alongside to report the shaft movement in roll amount. The anchor pitch 82 is at the lower extension of shin frame 14. The connection shaft with encoder 142 is installed to report the pitch angles. The connecting piece from shin frame 14 is through flexible axis device 66 installed between frame 14 and roll shafts. The walls cylindrical shape fit inside of ankle yaw 84 walls with two shafts trough slots providing center of pitch rotation. The journal slots are on ankle yaw 84 walls running up and down direction allow pitch shaft to slide inside, providing space for roll; at the front of ankle yaw walls 84. Two rigidity control bend block 68C is provided to give compression support for pitch limit at dorsiflexion at 20 degree and plantar flexion at 45 degrees. Four cables 402 to 408 (FIGS. 27A,B,C), each with an individual actuator, force sensor and spring box, control roll and pitch angles; an airtight chamber 34 is designed in the wall of shin frame 14. An air pump 64 links between back of shin frame 14 and foot frame 12. The air pump 64 provide negative air pressure in the air chamber using angle change during dorsiflexion and plantar flexion; an electric air control valve 62 operates by battery power 176 controlled by node spring box control unit 162 provide positive and negative air pressure for both flexible axis device 66 and rigidity control bend block 68. The rotation angles of devices are adjusted to specific user range of motion during calibration.

The present invention can apply cable spring box 70 (FIGS. 22A,B) and rigidity control block 68 to 68E (FIG. 10), to converse energy. It can also be present in other types of energy storage such as hydraulic drive, pneumatic system and air muscle.

FIGS. 15A, 15B, 16A and 16B show a knee device 88, which has plurality of components to permit the knee to rotate one degree of freedom, and achieves angular flexibility, strength of fixity to the knee joint 88 and allows natural knee rotation.

The knee pitch 88 provides 110 degrees of flexion; a gravitation balance initial spring 74 (FIG. 21) provides flexion to counter gravity when the knee lifts and ready for stepping. The connecting piece from thigh frame 16 has two walls with two journals providing pitch movement. These two journal associated with flexible axis device 66 allow for a natural rotation center between tibia and femur in knee pitch 88. At the back of knee joint 88 (popliteal fossa), a rigidity control bend block 68c is provided on each side, to give compression support for pitch limit at flexion from 15 to 110 degrees. The shafts are with shin frame 14. An encoder is installed to report the pitch amount. A knee cap rigidly connected with shin frame 14 function as a cable saddle 40 with cable trough to protect tension cable not stretch against user's knee.

Two cables 410, 412 (FIGS. 27A,B,C) provide knee pitch 88 flexion, each cable with individual actuator 72, force sensor 136 and spring box 70 control knee pitch's flexion angle. An airtight chamber 34 is designed in the wall of lower thigh frame 16, an air pump 64 links between back of shin frame 14 and thigh frame 16 across knee device 88, and the air pump 64 provides negative air pressure in the airtight chamber 34 using knee flexion. An electric air control valve 62 operates by cable adjustment unit 162 provide negative air pressure for both flexible axis device 66 and rigidity control bend block 68C; the rotation angles of devices are adjusted to specific user range of motion during calibration.

The present invention can apply cable spring box 70 and rigidity control device 68 to converse between types of energies. It can also be present in other type of energy storage such as hydraulic drive, pneumatic system and air muscle.

FIGS. 17A, 17B, 17C, 17D show a hip device which supports the three rotational degree of freedom of the hip joint 90,92, and 94. This configuration affords a median range of motion for all rotational degree of freedoms and provides the user with the capability of not just walking gaits but larger range attitude in bipedal ambulation. These features provide an efficient approach to solve geometry and lateral force transfer complexity of hip device 90, 92, and 94.

The hip device's center point 90B for all these components is approximately at the contacting point of head of femur to acetubulum on ilium, ischium. The first component control hip roll 94 is fixed on the hip base frame 18 and the component is a 90 degree cylindrical frame connected with shaft and journal connection at the back of gluteus maximus on hip base frame 18. The shaft center line points to the approximate hip center 90B and the other end of the hip roll device 94, a curved sliding track 94B enables hip roll 94 to support on and sliding along the cylindrical track. The cylindrical track block 94B is fixedly connected at hip base frame 18 aligned to femoral head, center about the approximate hip center 90B. With these two guides, the hip roll device 94 is confined to rotate about local y-axis only; plurality sets of rigidity control block 68C, non-linear tensile spring pad 76 (FIG. 23) and springs 74 (FIG. 21) are installed to provide a stable equilibrium position at the initial position, which is adjustable for user's application. An encoder sensor is used to report the roll angle and it provides range of movements is set to 40 degree hip abduction and 20 degree hip adduction. The hip yaw device 92 has a linear bearing that allows it to slide only along track of hip roll device 94. While the hip roll device 94 is in zero roll (Ry=0) position, the hip yaw device 92 provides rotation of z-axis about the approximate hip center point. A set of springs is installed at both end of the hip yaw device 92 to assist it in the initial position as shown in FIG. 21. A stretch sensor is used to track sliding distance and provide data for yaw angle. The hip yaw device 92 supports a shaft for hip pitch device 90. The shaft center points to the approximate hip center point and provides a range of roll movements that is set to 20 degrees medial rotation and 20 degrees lateral rotation.

The hip pitch device 90 is on the top of wall of thigh frame 16, with a journal bear against the shaft of hip yaw device 92, to rotate around local x axis and provide flexion of the thigh frame 16. A set of springs is used to set the initial flexion angle shown in FIG. 21. The hip pitch device 90 provides a range of movements set to 45 degrees backward extension and 90 degrees flexion. The encoder on the shaft reports pitch angle while the roll and yaw angle are set to zero. Cables 422, 424, 428 (FIGS. 27A,B,C) provide mobility of hip roll 94 abduction and adduction, cables 418, 418B (FIG. 27) provide hip yaw 92 lateral and medial rotation and cables 416, 414 (FIG. 27) provide hip pitch 90 flexion and extension. Sets of rigidity control compression block 68E are installed to provide locking capability of rotational degree of freedoms. A vacuum chamber 34 is designed in the hip base frame wall 18. An air pump 64 is linked between the hip yaw 92 and hip pitch 90 devices. The hip pitch movement provides negative air pressure in vacuum chamber 34. An electric air control valve 62 operates by cable control unit controls rotation limit by provide rigid compression support. The rotation angles of devices are adjusted to the specific user's range of motion during calibration. With the present invention, cable spring box 70 (FIG. 22B), non-linear spring pad 76 (FIG. 23) and rigidity control device 68 (FIG. 10) provide mobility and stability. It can also be present in other types of energy storage such as hydraulic drive, pneumatic system and air muscle.

FIGS. 18A, 18B and 18C show a waist and chest device 96, 98 which includes a hip base frame 18, an abdomen frame 20 and a chest frame 22. The hip base frame 18 is the base of hip devices 90,92,94 (FIGS. 17,A,B,C) and is the base to mount cable actuators and sensors used for the hip node control 502,504 (FIG. 31). Connections are placed on the top of hip base frame 18 to position hip roll 96 and hip yaw 98 relative to the abdomen frame 20. The sides between two frames connected with the rigidity control compression block 68D (FIG. 11A). Also included are cable actuators, rotational encoder 142 for roll measurement and stretch sensor for yaw measurement 142B and a set of edge sensors 148 for gravity force measuring. The center of roll and yaw is approximate to the vertebra location at the section. A gear set is used to measure displacements at a connection during yaw, create different linear movement in the horizontal slot to assure no strain apply to the user's vertebra in yaw movement.

The chest pitch 100 connection between abdomen frame and chest frame provides pitch range. The shaft and journal is centered approximate to the vertebra location at the cross section, to assure no strain apply to the user's vertebra in yaw movement. A set of cables, actuator, spring box and stretch sensor are designed at the front and back. Two rigidity control compression block 68D (FIG. 11A) are installed at the front and back and a set of edge sensors 148 is used for gravity force measuring. Vacuum chamber 34 is designed in the abdomen frame 20 and chest frame 22 wall. A pair of air pumps 64 is linked between the side of abdomen frame 20 and chest frame 22 frames provide positive and negative air pressure in the airtight chambers 34. An electric air control valve 62 operated by node spring box control unit 162 is used to reduce and provide air pressure to the rigidity control compression block 68D during operation and activate and release rigid compression support. Plurality of cables 434, 438 and rigidity control compression block 68D control waist roll 96. A plurality of cables 436 control waist yaw 98. A plurality of cables 440, 442 and rigidity control compression block 68D control chest pitch 100. Each cable has an actuator 72, force sensor 136 and spring box 70 (FIG. 22B). The rotation angles of the devices are adjusted to the specific user's range of motion during calibration. With the present invention, cable spring box 70 (FIG. 22B) and rigidity control device 68 (FIG. 10) provide mobility. It can also be present in other types of energy storage such as hydraulic drive, pneumatic system and air muscle.

FIGS. 19A, 19B and 19C shows a shoulder device that includes a shoulder clavicle roll/yaw 102 that supports a chest frame and functions as clavicle and scapula. The shoulder device arrangement provides median range of motion of all rotational degrees of freedom and the capacity for a larger range attitude in bipedal ambulation. Associated with calibration process 152, 154, the shoulder device enables an efficient approached to solve geometry and lateral force transfer complexity around the shoulder for the robotic mobility assistant device 10.

Shoulder roll 104 and shoulder pitch 106 provide three rotational degrees of freedom to the shoulder joint. The center of rotation for all these components is approximately at the contact point on the head of the humerus to the scapula in a ball and socket joint. The shoulder clavicle roll/yaw 102 is placed on top of the clavicle and is connected to the chest frame 22 by a ball joint connection 102B. Shoulder roll 104 is connected by shaft and journal 104B to shoulder clavicle 102. When shoulder roll 104 is facing forward, it supports 106 for arm abduction, adduction, whereas when shoulder roll 104 is facing inward, it supports shoulder pitch 106 for arm flexion, extension through shaft and journal 106B. The encoders 142 report angles at 104*b*, 106B. The stretch sensor to report rotation at 108. Cables controls the rotation angles of the shoulder devices components 102,104,106, and 108. Cables 444, 448 (FIGS. 25A,B) govern shoulder clavicle device 102 abduction and adduction for plus/minus 5 degrees range. Cables 450, 452 govern shoulder pitch device 106 vertical abduction 10 degree and adduction 45 degree. Cables 446 454 452 govern shoulder roll/yaw govern shoulder pitch device 106 horizontal extension 0 degree and flexion 90 degree. Cables 458 controls for medial and lateral rotation of upper arm axial rotation 108 between shoulder pitch/yaw 106 and upper arm frame 24. Rigidity control bend block 68C (FIGS. 11A,B) provides compression support for locking capability of rotational movement of shoulder device 102,104,106. Void airtight chambers 34 are designed in the chest frame 22 wall. Air pump is linked between 104,106 to maintain positive and negative air pressure in the airtight chambers 34. An electric air control valves 62 operates by cable adjustment unit 162 are used to maintain air pressure in the rigidity control compression block 68E to provide rigid compression support at joint. The rotation angles of devices are adjusted to specific user range of motion during calibration. With the present invention, cable spring box 70 (FIG. 22B) and rigidity control device 68 (FIG. 10) provide mobility. It can also be present in other types of energy storage such as hydraulic drive, pneumatic system and air muscle.

FIG. 20 shows an elbow and wrist device 110 configured to support the one rotational degree of freedom of an elbow joint. The center of rotation for the components is approximate at the contacting point between humerus, ulna and radius. The elbow pitch 110 provides 90 degrees of flexion. A gravitation balance initial spring 74 (FIG. 21) provides flexion at 10 degrees to counter gravitation and connects upper arm frame 24 and forearm frame 26. The connecting piece from upper arm frame 24 has two walls with two journals providing pitch movement. At the front of elbow joint 110, two rigidity control bend block 68C (FIG. 10) are provided on each side to give compression support for pitch limit at flexion from 10 to 90 degrees. The shafts are with forearm frame 26 and an encoder reports the pitch amount. Cables 460,462 govern elbow pitch 110 flexion and extension each with an actuator 72, force sensor 136 and spring box 70 (FIG. 22B), for controlling elbow pitch angles. Vacuum chamber 34 is designed in the wall of upper arm frame 24. An air pump 64 links between front of upper arm frame 24 and forearm frame 26 across elbow device 110. The air pump 64 provides positive and negative air pressure in vacuum chamber 34 using elbow flexion. An electric air control valves 62 operates by node spring box control unit 162 provide positive and negative air pressure for rigidity control bend block 68C. The wrist yaw device 112 provides pronation and supination degree of freedom between forearm frame 26 and palm frame 28 for a total 150 degree. Cables 464 control the rotation angles of wrist device 112. The rotation angles of devices are adjusted to specific user range of motion during calibration.

Features of this arrangement include providing angular flexibility, strength of fixity and torsional capacity to the elbow 110 and wrist joint 112 which allows natural elbow and wrist rotation. With the present invention, cable spring box 70 (FIG. 22B) and rigidity control device 68 (FIG. 10) provide mobility. It can also be present in other types of energy storage such as hydraulic drive, pneumatic system and air muscle.

Figure 21A:
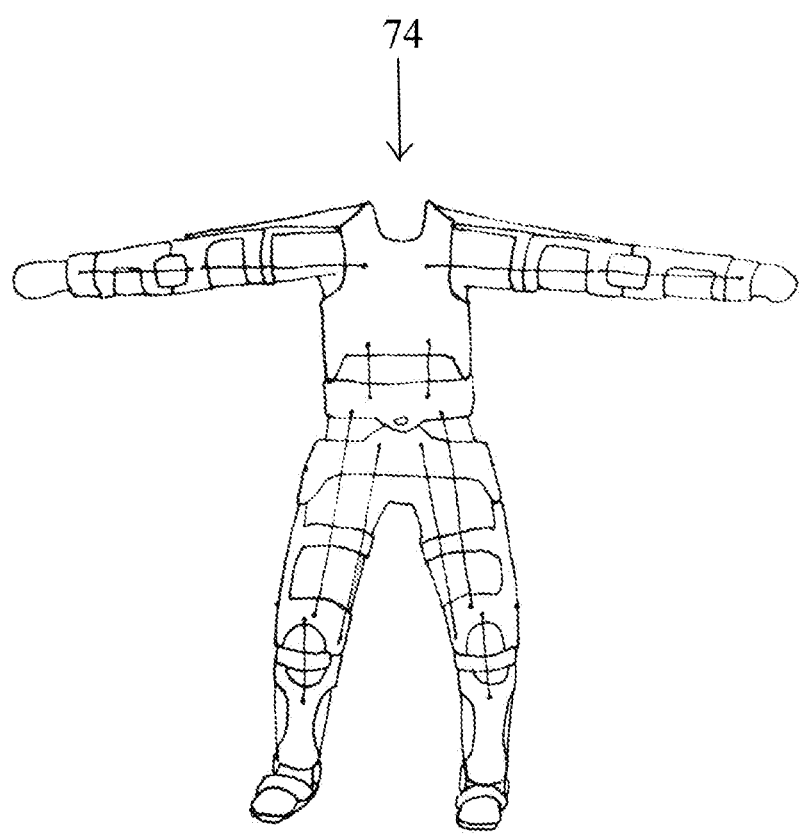
FIGS. 21A and 21B illustrate a gravitation balance spring system.
Figure 21B:
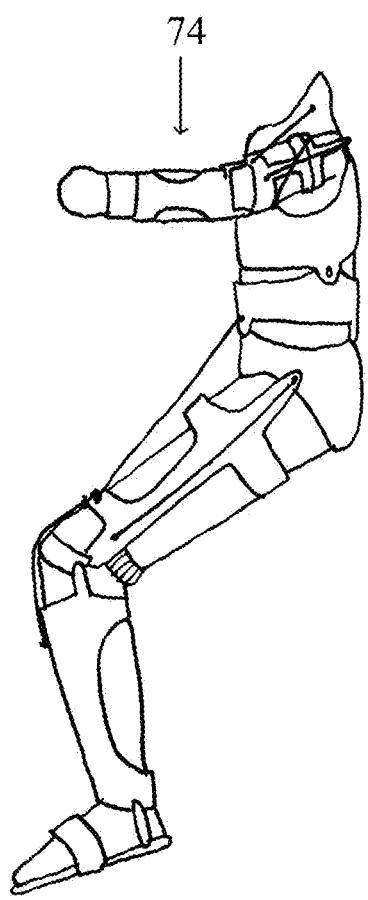

FIGS. 21A and 21B show a perspective view of gravitation balance initial spring 74. In order to reduce motor demand in operated joints, elbow 110, knee device 88, ankle pitch 82, shoulders 102 and hips 90, a set of springs in specific positions counter gravitation. This spring configuration provides passive gravity-balance articulated mechanisms to store potential energy and release when acting against gravitation. The spring can be installed to bring shoulder 102 into a no load state while in the rest idle position to balance the gravitation force. For hip joint 90, the spring is installed to position the legs at zero spring force state at highest knee point in common walking and side stepping ambulation. The springs release energy into kinetic energy to assist lifting arms against gravity and afford power assist in lifting leg before stepping.

For both arms 24 26 28, the gravitation balance initial springs 74 are installed to near horizontal level. For thigh frame 16, the gravitation balance initial springs 74 are installed at the thigh in 15 degree flexion and 10 degree abduction, and knee device 88 and ankle 82 are set to let shin frame 14 and foot frame 12 neutral by gravitation. With the present invention, passive gravity-balance articulated mechanisms use gravitation force to achieve a constant length for calculated spring output per specific user characteristic 202. The cables around the joints in the hand power acceleration from all other directions during bipedal ambulatory dynamics. The balance cable length adjustment can be performed by the node spring box control 162 (FIG. 21) and energy timing 174 (FIG. 38) units.

Figure 22A:
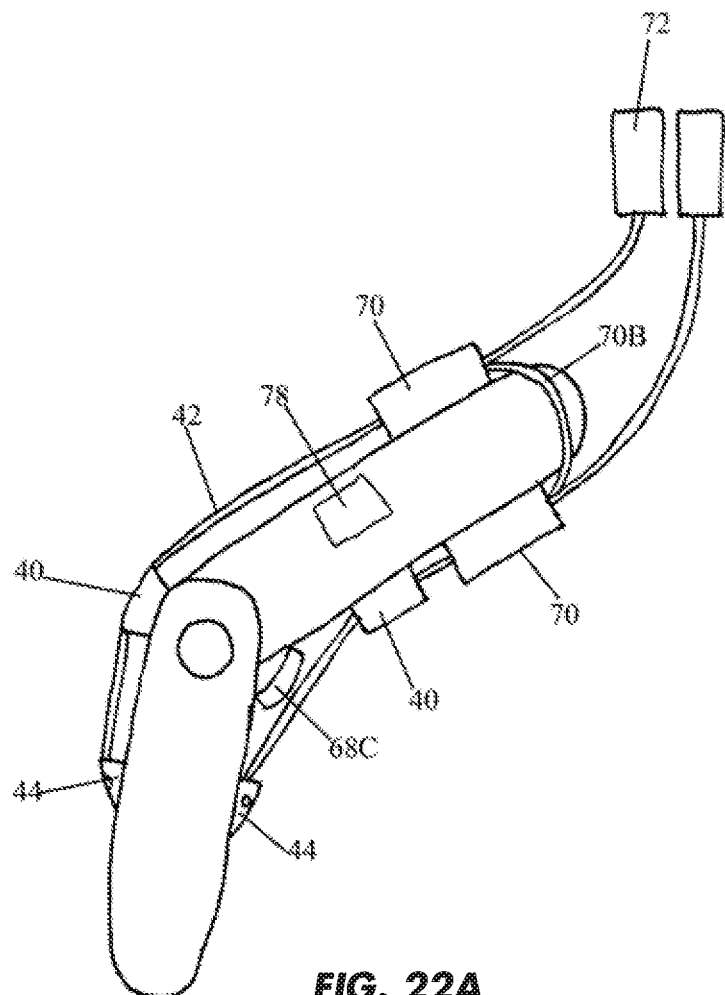
FIGS. 22A and 22B shows a cable spring box.
Figure 22B:
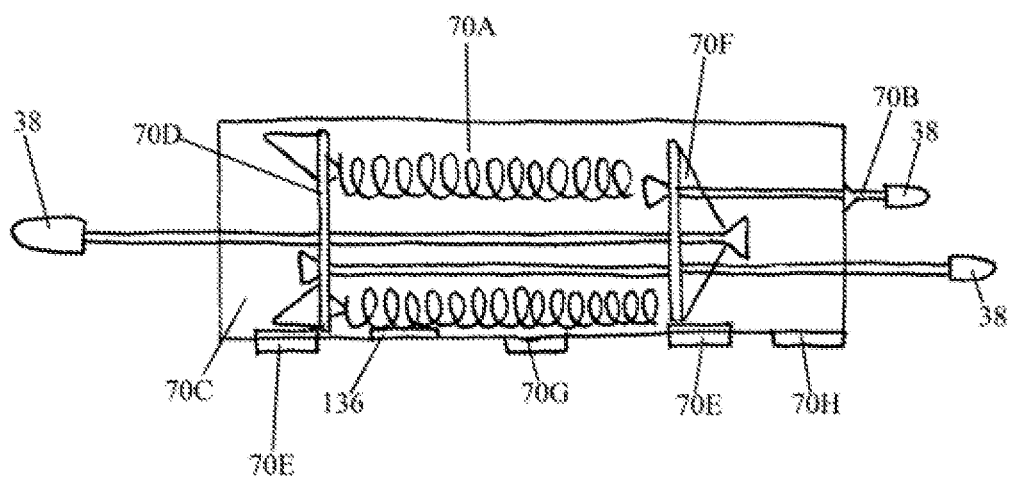
Figure 32:
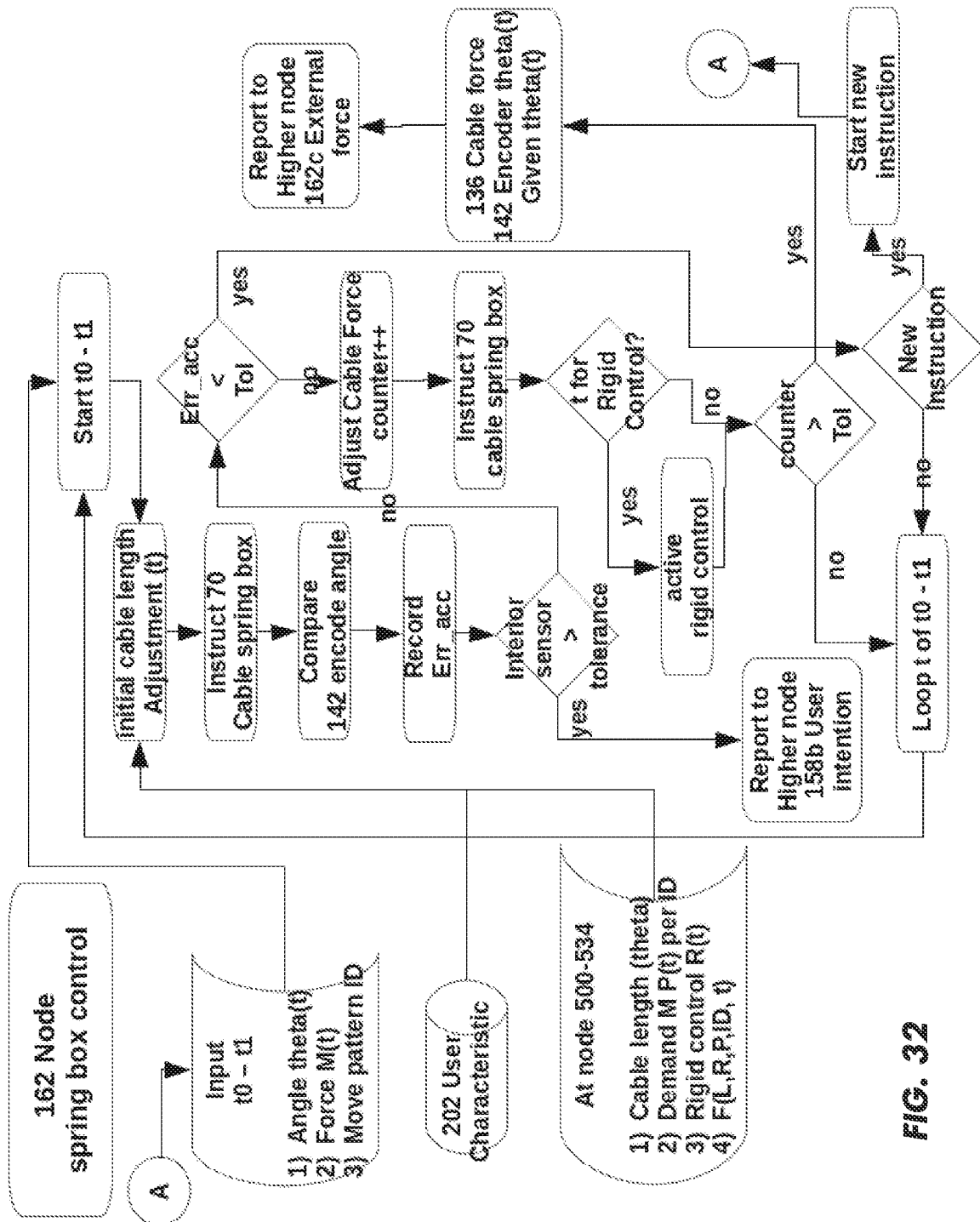
FIG. 32 is a process schematic of node spring box control.

FIGS. 22A and 22B show a cable spring box 70 that measures cable force 136, and stores, holds and releases elastic spring energy as instructed. A communication interface 70 receives and reports information to node spring box control 162 (FIG. 32). The cable spring box 70 is adjustable to facilitate energy conversion and can be modulated for easy installation. The cable spring box 70 device has a rigid box 70C with mount seat attached to the frame members cable spring 70A, auxiliary cable 70B, adjustable base plate 70D, solenoid ratchet clutch 70E, press plate 70F, a force sensor 136, control I/O port 70G, actuator communication port 70H, and cable actuator 72. In operation, two or more cable spring boxes are used, for flexion and extension. The elongation configuration is set to fit the specific joint's range of motion. The cable forces provided are set to the joint balance angle at the time step. The amount of forces is set to provide maximum output during either flexion or extension. In order to provide driving moment, one cable is set to reduce, or increase force amount, provided by cable actuator 72. The actuator 72 adjusts the base plate 70D position to change springs compression, balanced force; the ratchet 70E is used to fix base plate position as a clutch for cyclic movement and control energy conversion timing. The press plate 70F transfers pulling/releasing of bend cable, the joint angular change, into spring displacement. Since the spring boxes installation are paired and work in opposite directions, an auxiliary cable is designed to allow assistant each other. A control I/O power port 70G daisy chain is connected to other spring boxes provides two way control signal and power to devices.

With the present invention, an actuator can be used to active base plate 70E in adjusting spring balance force. The actuator can be powered by electrical, hydraulic or pneumatic power source. The actuators provide linear pulling by adequate capacity such as spindle, twisted string, moving coil, stepping solenoid motor.

Figure 23A:
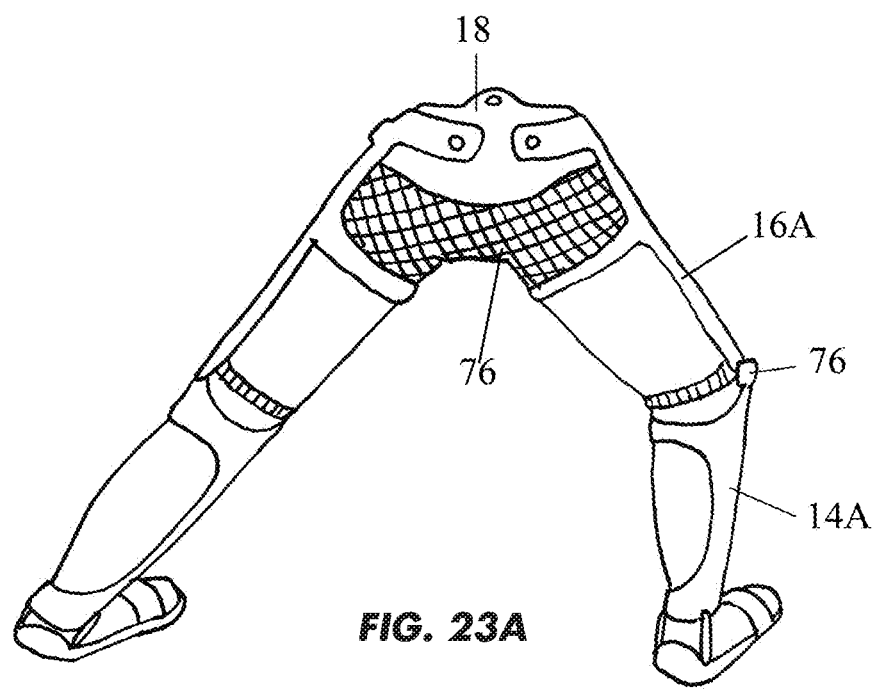
FIGS. 23A and 23B illustrate hip base frame with a non-linear spring pad and FIG. 23C is a force F vs. strain curve.
Figure 23B:
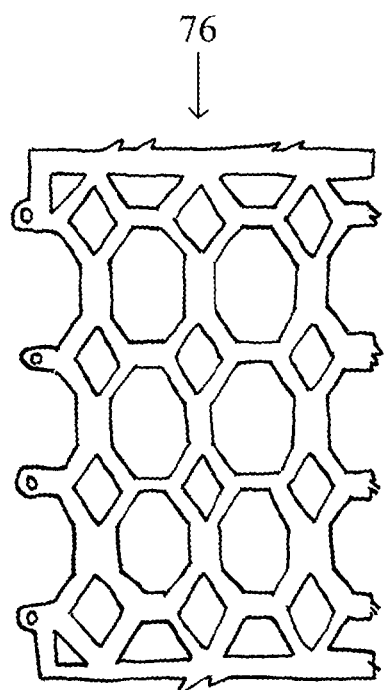
Figure 23C:
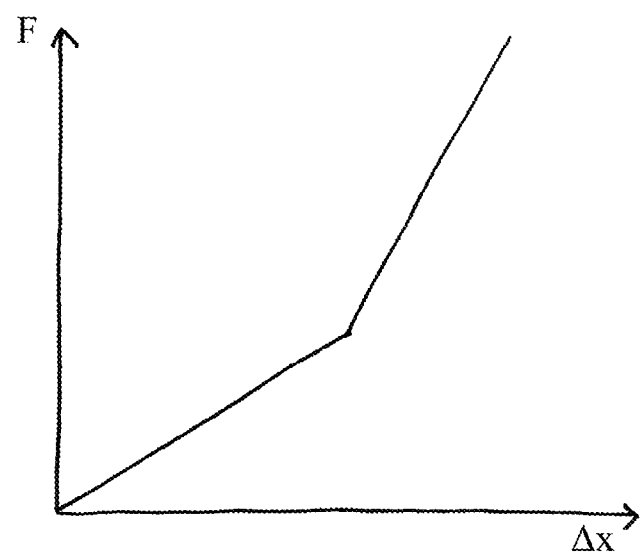
Figure 24:
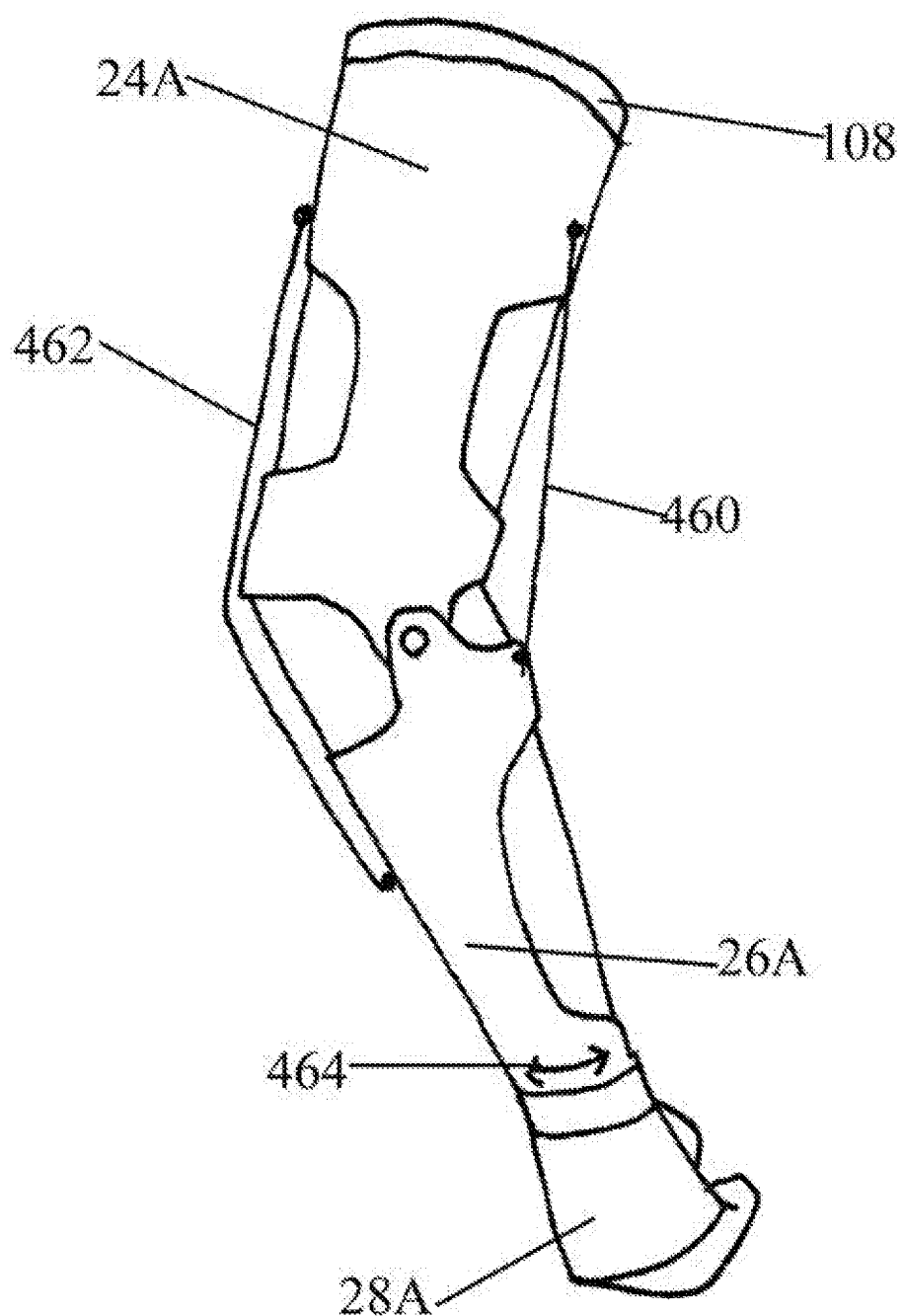
FIG. 24 illustrates a cable motor layout for an elbow.
Figure 25A:
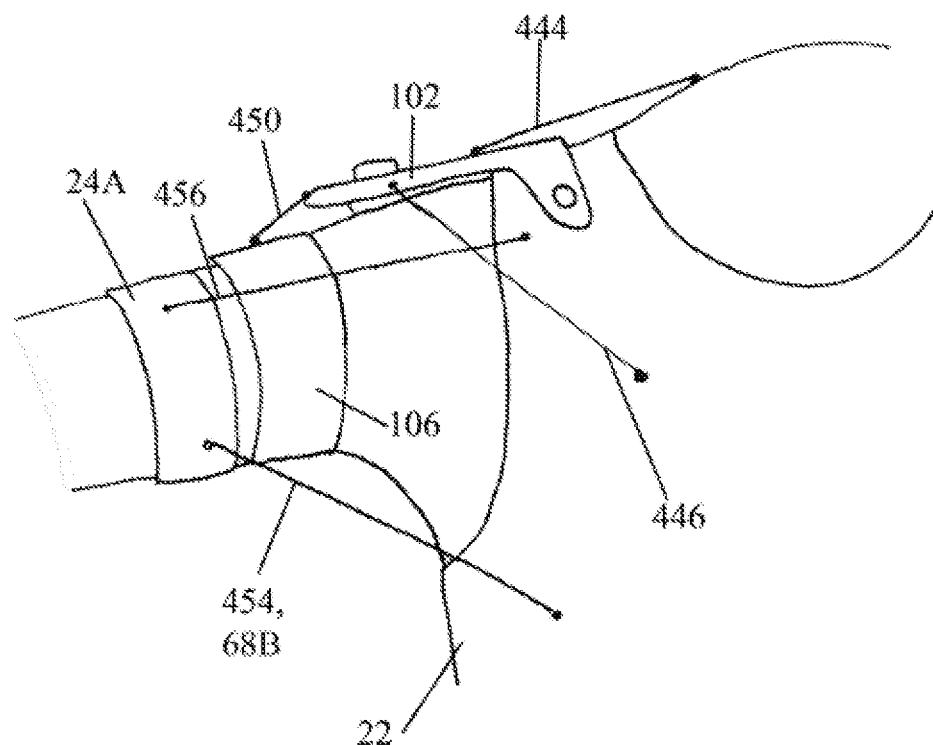
FIGS. 25A and 25B illustrates front and rear views, respectively, of a cable motor layout for shoulder.
Figure 25B:
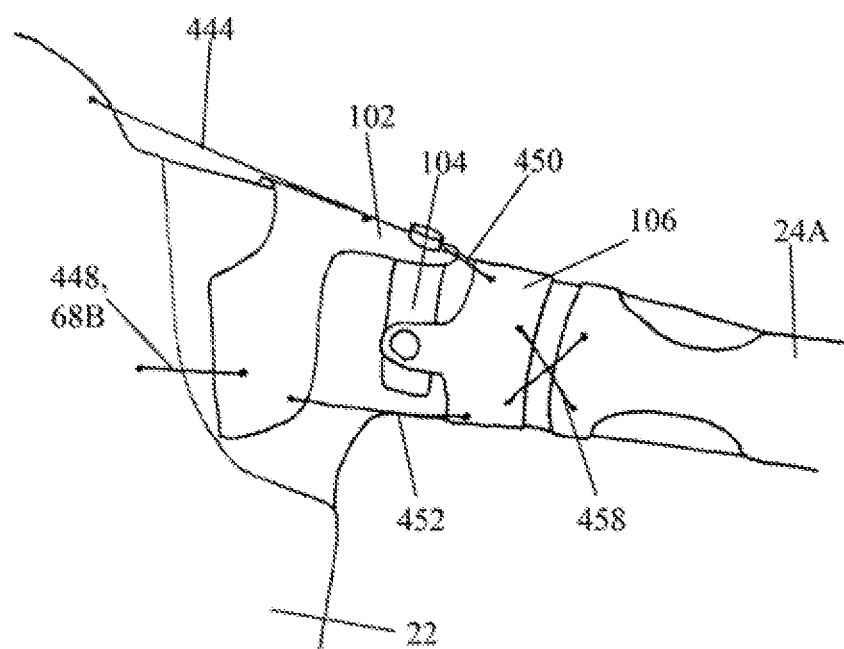
Figure 26A:
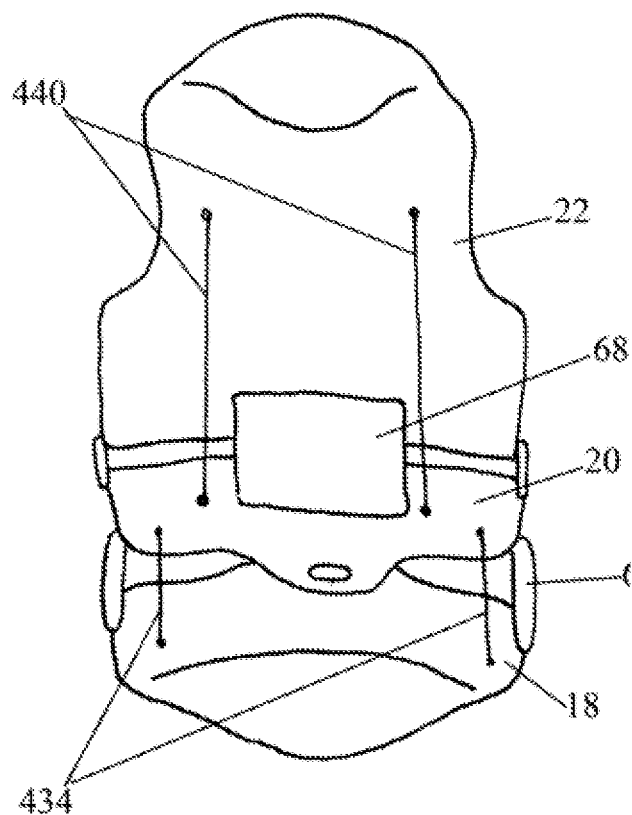
FIGS. 26A and 26B shows front and back views, respectively, of a cable motor layout for torso.
Figure 26B:
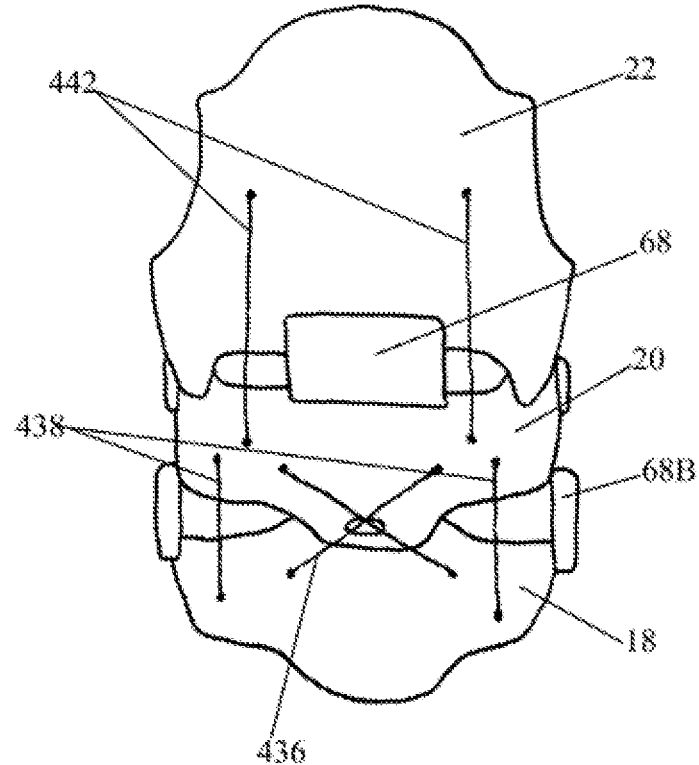

FIGS. 23A and 23B show a nonlinear spring pad 76 which is a geometrically patterned flexible material layout as a curve shell plate. As shown in FIG. 23C, under a stretching force, small rigidity occurs at the beginning, by limiting the shape's geometrical bending capacity. The rigidity greatly increases when elements deforms into close parallel orientation and resist tension by axial strength. The nonlinear spring pad 76 is used typically in knee device 88 area to allow easy knee flexion in small amount, but provide greater resistance to flexion after given angle. The nonlinear spring pad 76 is also used in between hip base frame 18 and thigh frames 16 to accommodate large hip movements and lateral stability; and provide constraints at motion limit.

This nonlinear spring pad 76 configuration provides a simple passive element for joint movement control in addition to active control such as cable actuator 72 and spring box 70 (FIG. 22B). When installed in between rigid frames, the pad protects a user from cables and moving instruments. Rubber materials with selected geometric patterns are used but stronger materials with different geometric pattern designs can be employed to attain the desired force and elongation response behavior.

FIGS. 24, 25A, 25B, 26A and 26B illustrate a cable motor layout that is arranged in between palms frame 28, forearm frame 26, upper arm frame 24, shoulder joint device 102 to 106, chest frame 22, abdomen frame 20 and hip base frame 18. The cable, spring box 70, actuator 72 are installed in areas that exhibit most the following human anatomy functions: hip abdomen front 434, hip abdomen lateral 436, hip abdomen back 438, abdomen chest front 440, abdomen chest back 442, shoulder clavicle up (levator scapulae) 444, shoulder clavicle down (subclavius) 446, shoulder clavicle in (trapezius) 448, shoulder arm up (anterior deltoid) 450, shoulder arm back (teres major) 452, shoulder arm front down (pectoralis major) 454, shoulder arm front lateral (coracobrachialis) 456, upper arm lateral rotation (infraspinatus) 458, elbow flexion (brachioradialis) 460, elbow extensor (triceps brachii) 462, forearm twist (paronator quadratus) 464. By using multiple sets of cable devices, the exoskeleton is able to perform attitude adjustments that are selected from calculation 160 and energy conversion based on energy synchronize timing unit 174 (FIG. 38) instructions. With the present invention by using cable actuator 70, spring box 72 (FIG. 22B), and energy synchronize timing unit 174 (FIG. 38) calculation as the motor source in performing attitude adjustment, the number and location of cable devices can be specifically configured from the layout for more complex or specific functions.

Figure 27A:
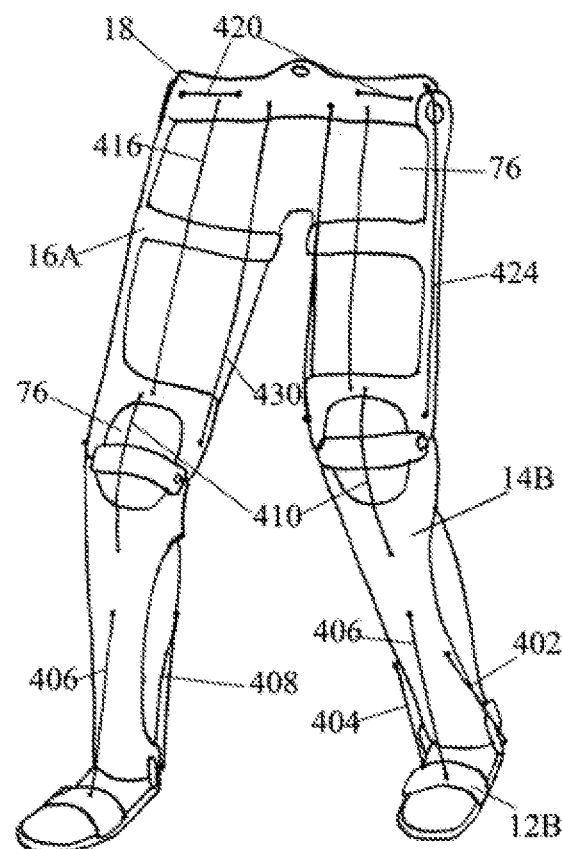
FIGS. 27A, 27B and 27C illustrates front, back and side views, respectively, of a cable motor layout for legs.
Figure 27B:
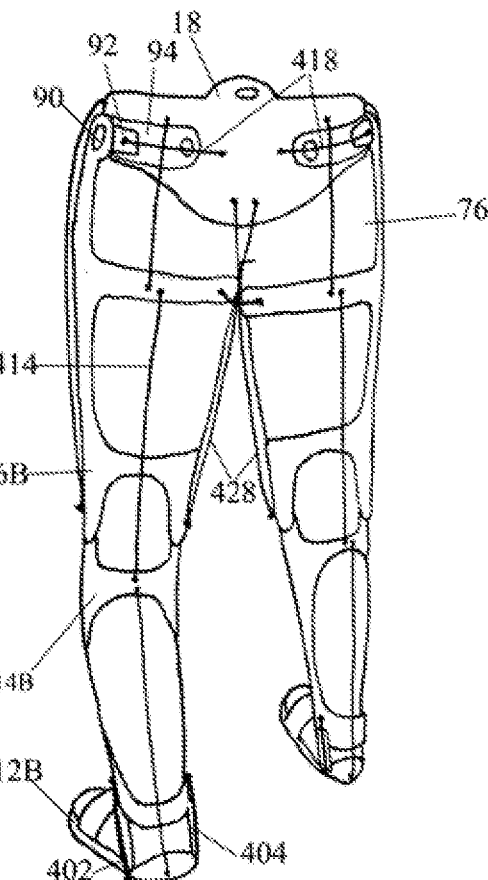
Figure 27C:
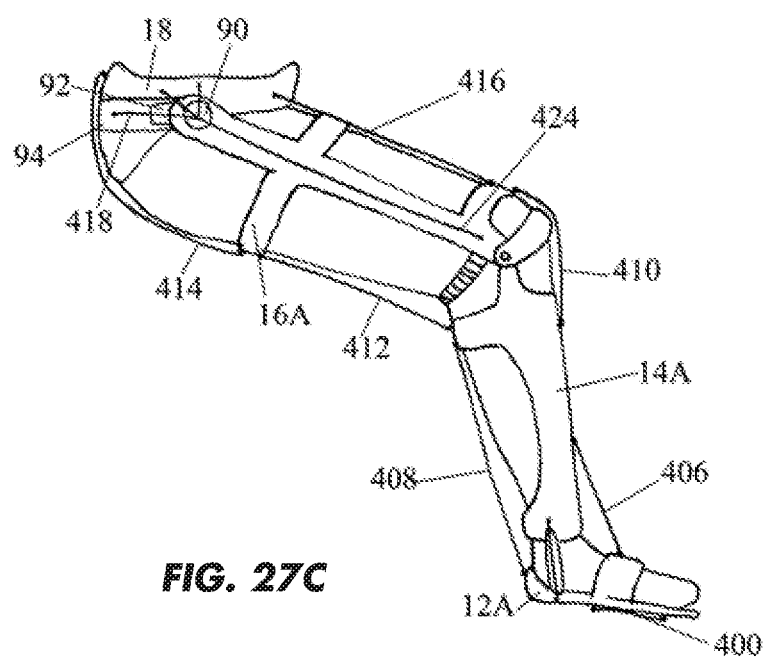

FIGS. 27A, 27B and 27C show a cable motor layout arranged in between hip base frame 18, hip joint devices 90 to 94B, thigh frame 16, knee joint device 88, shin frame 14, ankle joint device 82 to 86, foot frame 12, and toe joint device 80. The cable, spring box 70, actuator 72 are installed in an area exhibiting most following human anatomy functions: toe pitch cable (plantar flexion) 400, ankle eversion (peroneus group) 402, ankle inversion (extrinsic posterior) 404, ankle dorsiflexion (dorsiflexion) 406, ankle plantar flexion (gastrocnemius) 408, knee extension (quadriceps femoris) 410, knee flexion (bicep femrois) 412, hip extension (hamstrings) 414, hip flexion (illiacus+psoas major) 416, hip medial rotation out (obturator gemellus) 418, hip medial rotation in 420, hip lateral flexion (gluteus medius) 422, hip lateral flexion out (tensor facias latae) 424, hip lateral flexion in back (gracilis) 428, hip lateral flexion in front (gracilis) 430, hip and lateral flexion stable 432.

Employing multiple sets of cable devices provide the capability of performing attitude adjustments that are selected from posture selection process 160 and energy conversion based on energy synchronize timing unit 174 (FIG. 38) instructions. By employing cable actuator 72, spring box 70 (FIGS. 22A,B), and energy synchronize timing unit 174 (FIG. 38) calculation as the motor source in performing attitude adjustment, the number and location of cable devices can be varied from the layout to implement more complex or specific functions.

Control and Network Systems

Figure 28:
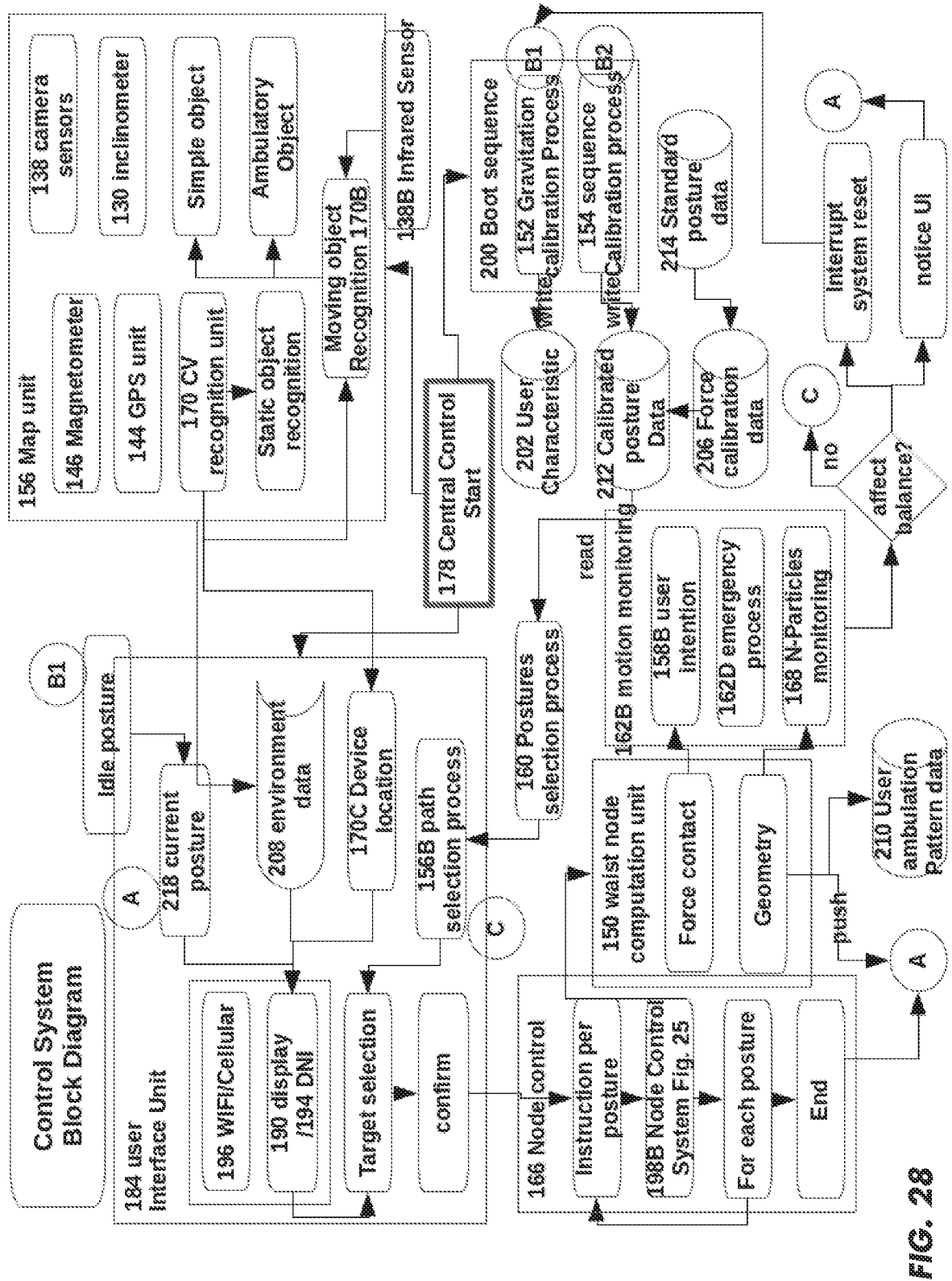
FIG. 28 is a block diagram view of a control system.

FIG. 28 shows a control system schematic that includes multiple computing boards with processors 180 such as, single chip microcomputers/controllers 198, multi-core processors running on open source operating systems. The system has multiple computer-readable storage media configured to store computer-readable programs and program accessible information. The computer-readable programs are executed by the processors to operate various actuators, devices, sensors. The computer board is supplied with power by adequate power supply such as portable battery pack 176. A set of specific software processes are written to execute the process flows. The software programs are written by C, C++, Assembly, scripts or device specific languages to assure efficiency, future easy of maintainability and improvement. The communication between processes on the same multiprocessor, multi-threads capable computing device will be relied on to provide low level system functions.

The programming the control system is based on the network of node control 198B (FIG. 31), gravitation 152 and sequence calibration 154 (FIG. 30), map unit 156 (FIG. 29), path selection unit 160b (FIG. 34), postures selection unit 160 (FIG. 35), node spring box control unit 162 (FIG. 32), user interface unit 184, waist node control unit 150 (FIG. 33), N-particles simulation unit 168 (FIG. 3C), computer vision recognition unit 170, moving object recognition unit 170B, camera position recognition unit 170C, bipedal ambulatory recognition unit 107D, vertical edge recognition unit 172, energy timing unit 174 (FIG. 38), central control unit 178 and emergency process units 162D. Features of the controls system include performing a distribute node control network 198b to share work load, provide coordination for bipedal ambulatory of the robotic mobility assistant device 10.

The controllers are configured to execute computer-readable programs to operate one or more cable spring box 70 (FIGS. 22A,22B), cable actuators 72 devices to apply forces between frames and activate frames to provide controlled levels of compliance between devices in different modes of operation. The computer-readable storage media are configured to store program accessible information, not limited to boot sequence data 200, user characteristics data 202, rules of ambulation and attitude 204, force calibrated baseline data 206, environment data 208, user ambulation pattern data 210, calibrated posture data 212, standard posture data 214, current joint coordinates data 218, next joint coordinates data 218B, other bipedal joint coordinate data 218B, and N-particles predicted joint coordinates data 218B. Computer-readable programs executed by the processors to operate actuators, devices, sensors, not limited to, toe/heel electrical magnetic floor suction device 48 (FIG. 12B), electric air control valve 62, air pump 64 (FIG. 15B), cable spring box 70 (FIG. 22B), cable actuator 72, inclinometer sensor 130, accelerometer 130b, sole pressure sensor 132, sole distance sensor 132b, interior pressure sensor 134, cable force sensor 136 (FIG. 22B), camera sensor 138 (FIGS. 1,2), infrared sensor 138B, air pressure sensor (vacuum chamber) 140, encoder (extension shaft and journal) 142 (FIG. 15A), stretch sensor 142B (FIG. 13A), GPS global positioning system 144, magnetometer 146, edge pressure sensors 148 (FIG. 18A), node control unit 166. The control system is powered by battery pack 176 (FIG. 1B) compatible to the system power requirement to provide operation power source.

With the present invention, a user interface unit 184 displays environment information 208, device next movement path selection 160B and posture selection 160 for user's confirmation. The user can sit inside the robotic mobility assistant device 10, or be in remote control position through wireless/cellular connection 196. The user confirmation is provided through audio 186 188, keypad 192 or through direct neural interface (DNI) 194.

Figure 29:
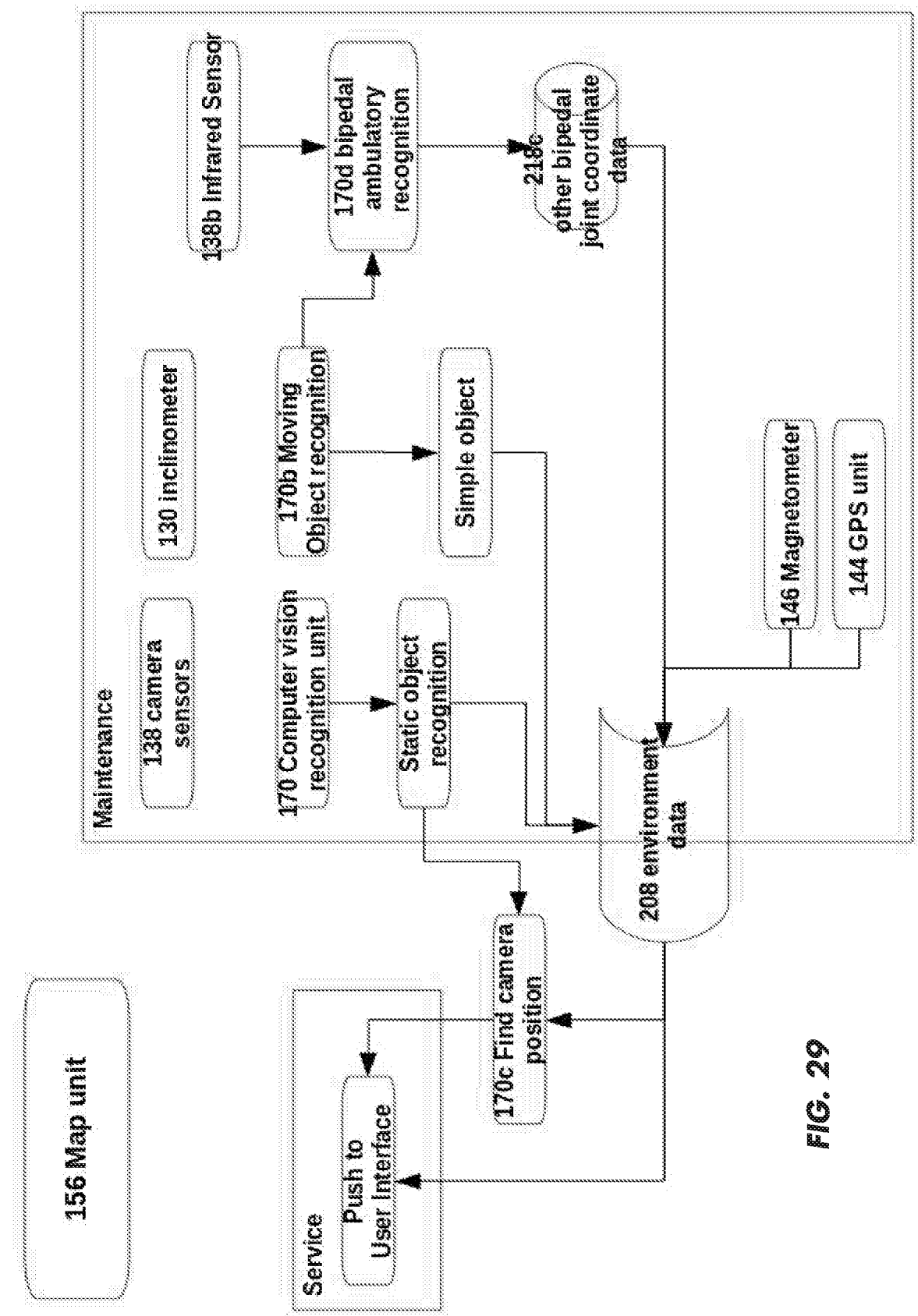
FIG. 29 is a process schematic of map unit.

FIG. 29 shows a process schematic for map unit 156, which is used to prepare environment data 208 for movement planning. This process unit is configured to compute processes running on independent processor units CPU/GPU 180 built on a computer board. Map unit 156 generates updated environment information process, record user routine activity, and minimizes the recognition and calibration effort. With bipedal ambulatory recognition unit 170D and the real time bipedal joint coordinate data 218C, the robotic mobility assistant device 10 has the ability to monitor and collaborate with human activity in the surrounding, and respond with path selection process 160B (FIG. 34) and posture selection process 160 (FIG. 35).

As the processor units CPU/GPU 180 are operating, the camera sensors 138, infrared sensor 138B pass images to computer vision recognition 170, identify external edges of surrounding objects. The calculated external edge is recorded in environment data 208, accessible at all time for user interface unit 184. Each time the robotic mobility assistant device 10 moves into a nearby position, the cameras sensors 138 provide another set of images from different view angles. The camera position recognition unit 170c calculates the location and orientation of device 10. Working with GPS global positioning system 144 if available, a local map of objects is updated constantly. A transformation between local and global reference coordinate system is kept to identify device 10 movements. The moving object recognition unit 170B compares the images to identify and calculate moving object. The simple shape objects are assigned with position, velocity, and acceleration for trajectory prediction purpose. The unit 170B takes images from infrared sensor 138B to recognize bipedal ambulatory 170D postures active in the near surrounding. The information stored in the other bipedal joint coordinate data 218D (FIG. 37) to support collaboration with other human activity.

With the present invention, camera sensor 138, infrared sensor 138B and image recognition are used to build three dimensional objects in the processed environment data storage 208; the inclusion of global positioning system GPS global positioning system 144 as index linked to previously processed environment data 208. The magnetometer can also map magnetic field information with three dimensional objects for position calibration.

FIG. 30 shows a process schematic of the calibrating process 152, 154 which runs through a network of node controllers 198B (FIG. 31). This calibration process runs on processor units CPU/GPU 180 on a computer board. At computer boot up, the gravitation calibration 152 is activated to a standing posture at the boot sequence 200. The ankle nodes 506 514 work autonomously in adjusting cable 402 404 406 408 for soles' ground contact by measuring sole pressure sensors 132 and distance sensor 132B. The adjustments stop at range of movement when uneven ground condition encountered. The toe pitch device 80 (FIG. 12A) is locked to allow moment transfer when ground contact complete. The knee node 508 516 (FIG. 31) adjust knee pitch 88 angle by using cable 410,412 (FIG. 27C), instruct ankle pitch 82 and roll 86 to adjust accordingly. The hip nodes 502,504 adjust cable 418,418B for hip yaw device 92 to align hip base frame 18 to device zero yaw orientation. Use inclinometer 130 (FIGS. 1,2) horizontal plane, gives instruction in knee and ankle node with pitch angles for hip target elevation to achieve hip base frame 18 zero roll (x direction horizontal).

Control cables 414,416 for hip base frame 18 close to zero pitch (y direction horizontal). The waist node controls waist roll 96 and yaw 98 device. Working with abdomen frame 20 inclinometer 130, and the edge sensor 148 between hip base 18 and abdomen frame 20. Control cable spring box 434, 436,438 to maintain abdomen frame 20 in vertical orientation according to abdomen frame 20 inclinometer 130 reading. The pitch and taw values of accelerometer 130b is calibrated. Ankle nodes report readings to the hip nodes 502 510 for further legs posture adjustments until sole pressure sensors 132 reach equivalent readings to assure gravity center is located in between the polygon defined by the heels and toes. The shoulder 1 nodes 520, 528, shoulder 2 nodes 520,530, elbow nodes 524,532 and wrist node 526,534 control their cable spring boxes 70 to release all cables.

The boot gravitation calibration 152 process completes while further adjustments create minimum differentiation from sole pressure sensor 132 reading, and abdomen frame 20, chest frame 22, hip base frame 18 are close to vertical. During calibration, a set of edge pressure sensors 148 around joint degree of freedom is used to measure the zero moment configuration at the joint. While at the waist roll device 96 and chest pitch device 100, the value of reading is recorded with inclinometer 130 ready for error between equipment and gravitation alignment; the collected user specific information is recorded in user characteristics data 202. The sequence calibration 154 readings provided sequence directive instructions from the standard posture data 214, perform node adjustments 150 to satisfy functional result; collect operational information such as cable length, cable force 136, edge pressure sensor 148, encoder sensor 142 in the operation of each given sequence. This process 154 build references between posture skeleton geometry 236 and control instruction in gravitation load only condition; in more than one postures function specification, forces are provided for ready under load condition. At the completion of the process 154, data is recorded for calibrated posture 212.

The gravitation calibration unit provides reliable data for waist node calculation unit 150 even when one group of sensors is under environmental interference. Such interference could be adjacent to strong magnetic field, darkness with unrecognizable visual images or acceleration affected by unknown external or internal force. Sequence calibration process 154 is a series of load conditions calibrate the robotic mobility assistant device's 10 joints orientation. Whether or not the device 10 is worn by a user, the center of rotation of each joint changes value per user; a designed process captures alignment information based on load, and gravitation input in series of predefined posture sequences. The interior pressure sensors 134 are placed at the inner face of frame of these locations: back of hip, bottom of thigh above knee, top of shin below knee, bottom and back of shin above heel and underneath the feet. These pressure sensors provide data at the squatting position for each knee bending angle. The sensors' readings cross reference hip 90, knee 88 and ankle 82 encoder angle reading.

The horizontal force 4 is applied along local x axis, (center from left hip/shoulder and point to right hip/shoulder), the edge pressure sensors 148 located at the shoulders are used with encoder 82 to find the angle with minimum bending. The measured encoder reading is marked as base line for shoulder x axis. The other horizontal force is applied toward the shoulders in the y axis while the user's back is being supported. The edge pressure sensors 148 at the shoulders are used with encoder 82 to the angle with minimum bending direction. The measured encoder reading is marked as base line for shoulder y axis.

The present invention description listed limited type of force inputs for calibration; there are a lot more input directions, and locations the calibration uses, based on static model 224 of balance. While extensive load calibrations are performed, the data correlation between rotational encoder 142, cable force sensor 136 and inclinometer sensor 130, and sole pressure sensor 132 provide better reference for real time movement control.

Sequence calibration 154 enables encoder baseline for the robotic mobility assistant device 10, when axis centers are not accessible. In addition, while measuring basic force input, the device 10 has the calibrated baseline data 206 for decision making.

Figure 37:
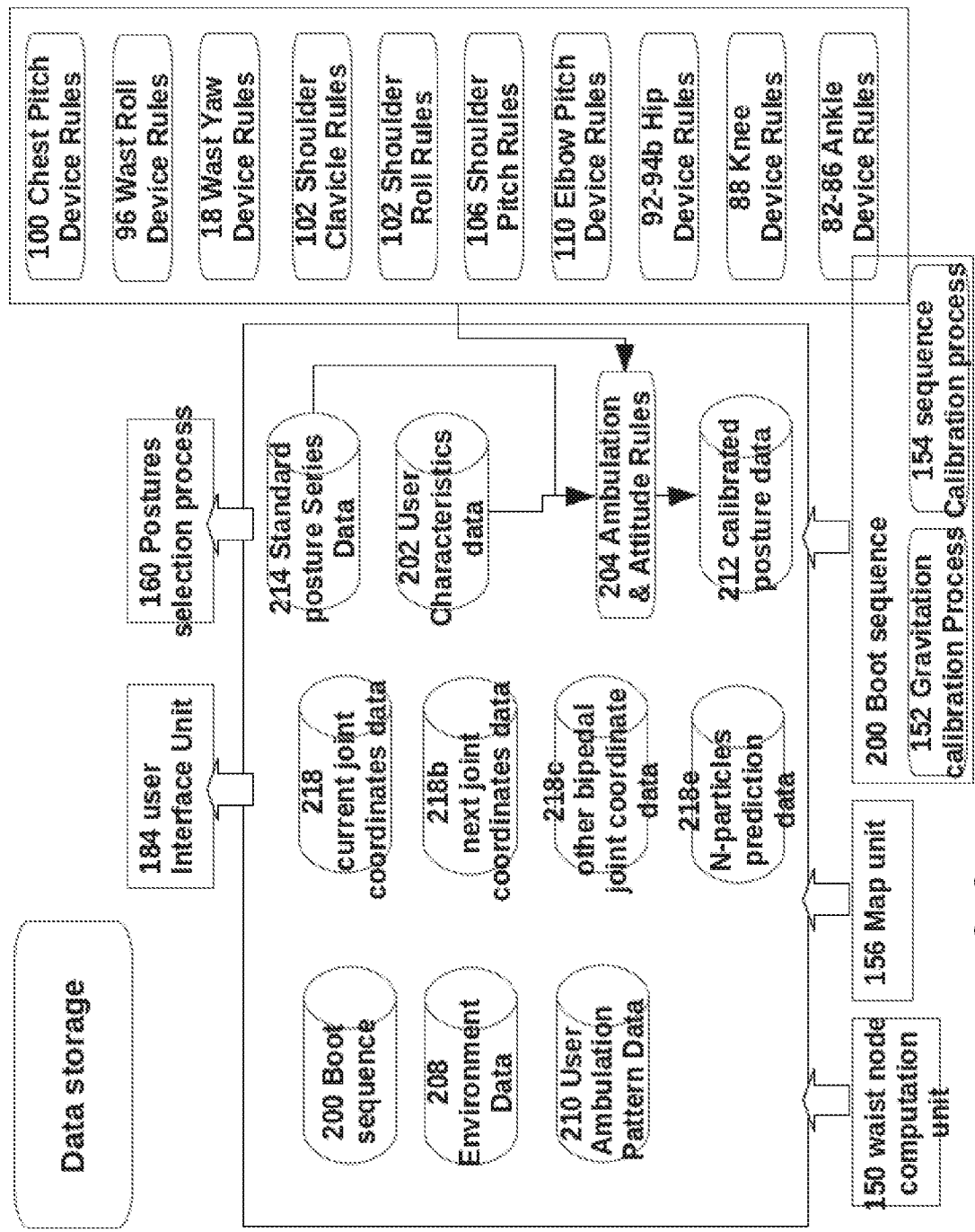
FIG. 37 is a schematic of data storage.

The calibration through movement provides measurements to identify an individuals' mass of limbs (appendages) plus the weight of the device equipment, for each joint device frames. The idle stand confirms total weight by the sole pressure sensors 132 summation. Shifting right moves all weight onto one foot, lifting up left knee and read cable 416 force sensor to calculate weight for left leg and reach out left leg, read cable 410 force for weight of shin frame 14 and foot frame 12. Adjust hip yaw device 92 orientation to synchronize weight shifting using cable 418 418*b*. Measurement of cable force records rotational mass of user inertia and abdomen frame 20, chest frame 22, upper arm frame 24, forearm frame 26 and palm frame 28. Level arms, T pose measure cable 450 forces to calculate arm weight. Lift forearm frame 26 15 degrees, read cable 460 force to calculate weight of forearm frame 26 and palm frame 28. Side step left is divided into several basic steps: idle, balance with two feet equally sharing weight, shift weight onto right foot lift up left foot and free hang from hip, roll the left hip base 18 up 94, extend out left foot, lay down left foot, shift weight to middle of two feet, shift weight entirely to left foot, lift up right foot and free hang from right hip, place down right foot back to idle position. Side step right sequence is symmetrical. Step forward can be derived based on the above side step sequence by adding a 45 degrees hip base 18 orientation changes between step 6, plus a 90 degrees hip base 18 orientation change between two idle positions 9 and 1. In this calibration sequences, joints cable length in relation to the encoder 142 are recorded for user characteristics data 202 (FIG. 37).

Instruction is given during the sequence calibration process, through user interface 184 display 190 and audio 186,188. The training can be performed and practiced to increase collaboration accuracy between user and device 10.

The benefits of the calibration the robotic mobility assistant device 10 are derived from using the physics characteristics of the actual user. In the basic stepping sequences, the cable forces and encoder reading in common operation can be calibrated and optimized for energy conservation. With the present invention, three movement sequences are preferably used. The sequences are not confined within three, but were developed from hundreds of discrete sequences to measure and optimize a range of bipedal ambulation physics.

FIG. 31 shows a process schematic of node control network to control and provide adequate real time efficiency for the robotic mobility assistant device 10. The network of node system is invented for the sensor and device control. Each node control 162 (FIG. 32), an independent computing unit, is provided per joint device, manage all the cable spring boxes 70, encoder 142, inclinometer 130, air pressure sensor 140, edge pressure sensor 148, and interior pressure sensor 134 around the subject joint. The collected sensor information feedback to root node to collaborated with other nodes. In between node control unit 162, communication is provided in serial USART or USB in both directions to perform data exchange. The links between nodes are as shown. The node control network separates the control and sensor collecting processes into independent group of nodes. The real time knowledge of current posture geometry, force information of waist node 500 gives self-awareness to the robotic mobility assistant device 10.

Figure 33:
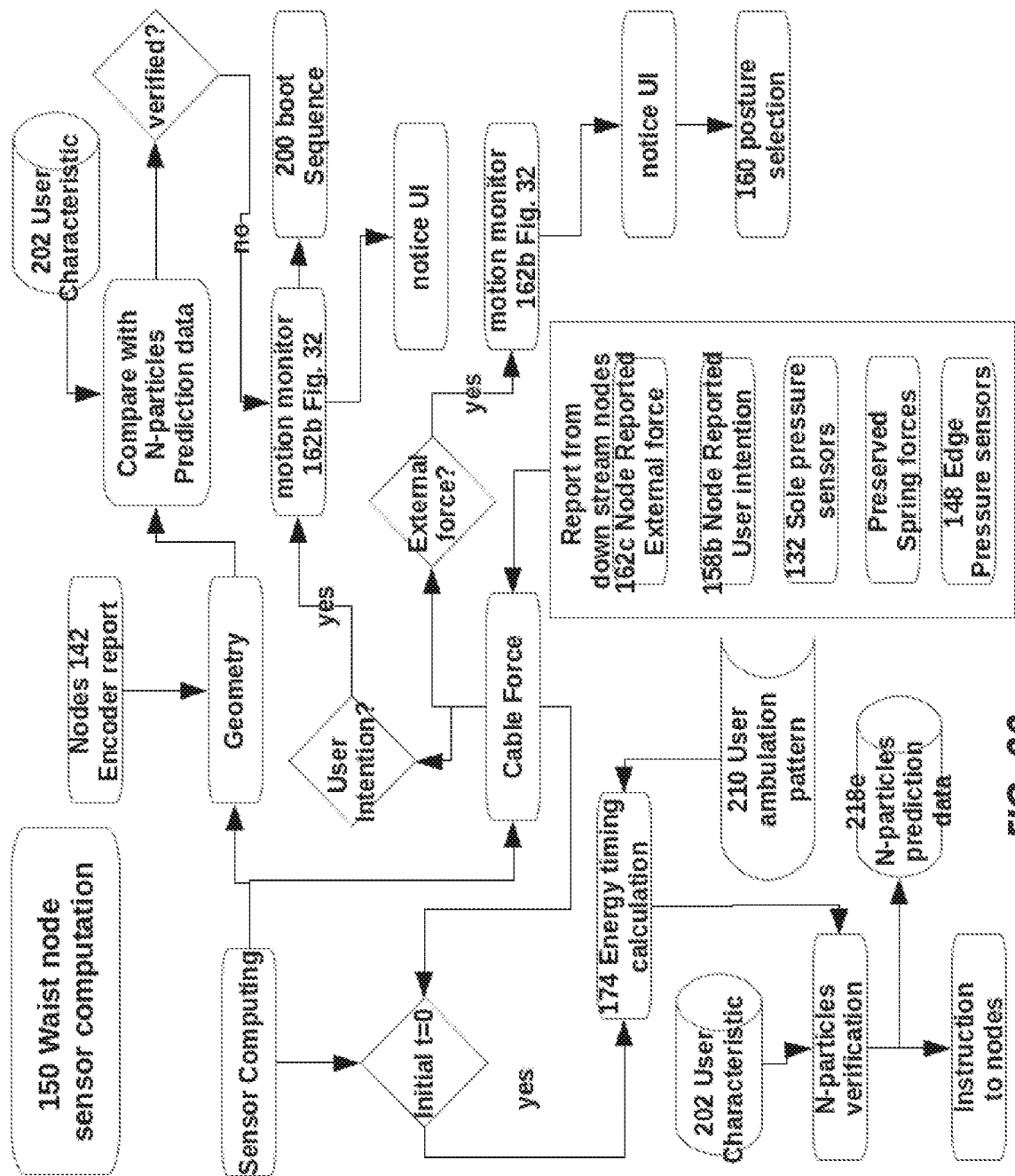
FIG. 33 is a process schematic of waist node sensor computation.

The node network is formed in a hierarchical order. The waist node 500 is the root of the command tree. There are two three tree branches: two legs and one chest node 518, branches out to two shoulders and arms. The leg branch from waist node 500 down is composed of right hip node 502, right knee node 504, right ankle node 506 and right toe node 516. Left hip node 510, left knee node 512, left ankle node 514 and left toe node 516. From chest node 518 branches out to two arms: right shoulder node 1 520, right shoulder node 2 522, right elbow node 524 and right wrist node 526. Left shoulder node 1 528, left shoulder node 2 530, left elbow node 532 and left wrist node 534. The waist node 500 contains a computation unit 150 (FIG. 33). Performing energy timing 174 (FIG. 38), geometry computation, force computation, user intention monitoring 158B and external force monitoring 162C. Monitors reported health of the other nodes, coordinate functions, process user intention report and external force report. Each nodes sensors process control: cable force sensor 136, joint encoder 142, stretch sensor 142*b*, air pressure sensor 140, interior pressure sensor 134, edge pressure sensor 148, inclinometer 130, sole pressure sensor 132 and sole distance sensor 132B. Each nodes device process control: spring box control 162, actuator cable length, spring force preserved, spring force timing. Air pressure control. Vacuum chamber pressure sensor 140, engage electric pump 64B, flexible axis device 66, rigidity control blocks 68. The control centered at waist node 500, accept and execute instructions by passing down to each node and accept response from the key nodes of each branch such as: hip nodes 502, 510, chest node 518, shoulder 1 nodes 520, 528. Key node receives instruction and control feedback to achieve target result. The execution progress and incidences that need to be coordinated with other branches get report to waist node 500 for further process.

This distributed nodes network system is used to control the robotic mobility assistant device 10, and the node system can be expanded to cover different configurations of the invention.

FIG. 32 is a process schematic for node spring box control unit 162. This node spring box control unit runs on processor units CPU/GPU 180 on a computer board. The robotic mobility assistant device's 10 joints are powered by cables shown in FIGS. 24 to 27C and gravitation balance initial springs 74 (FIG. 21). The lengths of cables are selected per device frame element dimensions and are not be predetermined. The calibration processes 252 254 (FIG. 30) calculate and record the cable length variation per encoder rotational degrees of freedom 142 (FIG. 5) while the spring elongation length is related to the user geometry.

By placing the control of all devices around a joint into one process, any abnormal motion result can be dealt on a local level. However, in an unrecoverable event, the control can raise a request to coordinate with upstream nodes in the branch. The node spring box control 162 is performed for each joint and each node controls more than one spring box for power injection performing the robotic mobility assistant device 10 operations. The functions of cable spring box 70 (FIG. 22B) around a specific joint include: controlling rotation angles, preserve elastic energy given target angle, force, and posture pattern. The process 162 references the user characteristics data 202 (FIG. 37), for initial values time history. Waist node 500 (FIG. 31) provides joint geometry driving target to downstream node with initial control data from time zero t0 to time complete t1 with: (1) joint angle theta(t), (2) joint moment demand M(t), and (3) limb movement pattern. The initial cable control information is retrieved from user characteristics data 202 (FIG. 30).

The node process starts into the loop for each time step. The instructions to drive cable actuator 72 through spring box interface are given. Read joint encoder 142 for angular change. Compare the encoder angle with given target angle at time step. The accumulated error is recorded. The tolerance of accumulated error set the ceiling before cable force adjustment is called. For each adjustment, a counter is counting until each given limit. At the limit, the node process report to the key node with force, angular displacement value, for the existent of possible external force. The waist node 500 will take action to respond to the condition and start a new node target instruction.

In each time step in the execution loop, node spring box control 162 monitors interior pressure sensor 134, as force input by the user. Reports are issued to waist node 500 if user intention shows consistent. The waist node computation unit 150 (FIG. 33) takes action to respond to the condition and start a new control target instruction. In the execution loop, node control activates or deactivate rigidity control device 68 at time t as instructed.

FIG. 33 shows a process for waist node sensor computation unit 150. This control unit runs on an independent processor units CPU/GPU 180 on a computer board. A feature of the waist node sensor computation unit 150 is that the sensor computation is at the top node (waist node 500) of the node network system 166 (FIG. 31). It takes all real time geometry, force sensor information collected and places them in one process. It monitors and calculates the critical condition that could affect the robotic mobility assistant device's 10 balance and makes user notification and correction.

Waist node 500 is giving instructions to three key nodes: chest node 518, hips nodes 502,510 (FIG. 31) to execute the posture change. In the process of executing command, the relevant information of progress is reported back from the key nodes. These are two types of information being processed and evaluated for device 10 balance and health: (1) the encoder geometry data and (2) all types of force data. While in the initial mode of every posture execution, the energy timing 174 (FIG. 38) calculation is performed. The cable length for degree of freedom at each joint is calculated by energy timing unit 174 (FIG. 38) to provide adequate spring elongation adjustment. The calculation use encoder geometry, user characteristic data 202, user ambulation pattern 210, and the calculated posture data 212. In time sequence, the data is passed to N-particle simulation unit 168 for verification. When confirmed, the calculated control time history is passed into each node for execution and stored as N-particles prediction data 218E (FIG. 37).

Figure 36:
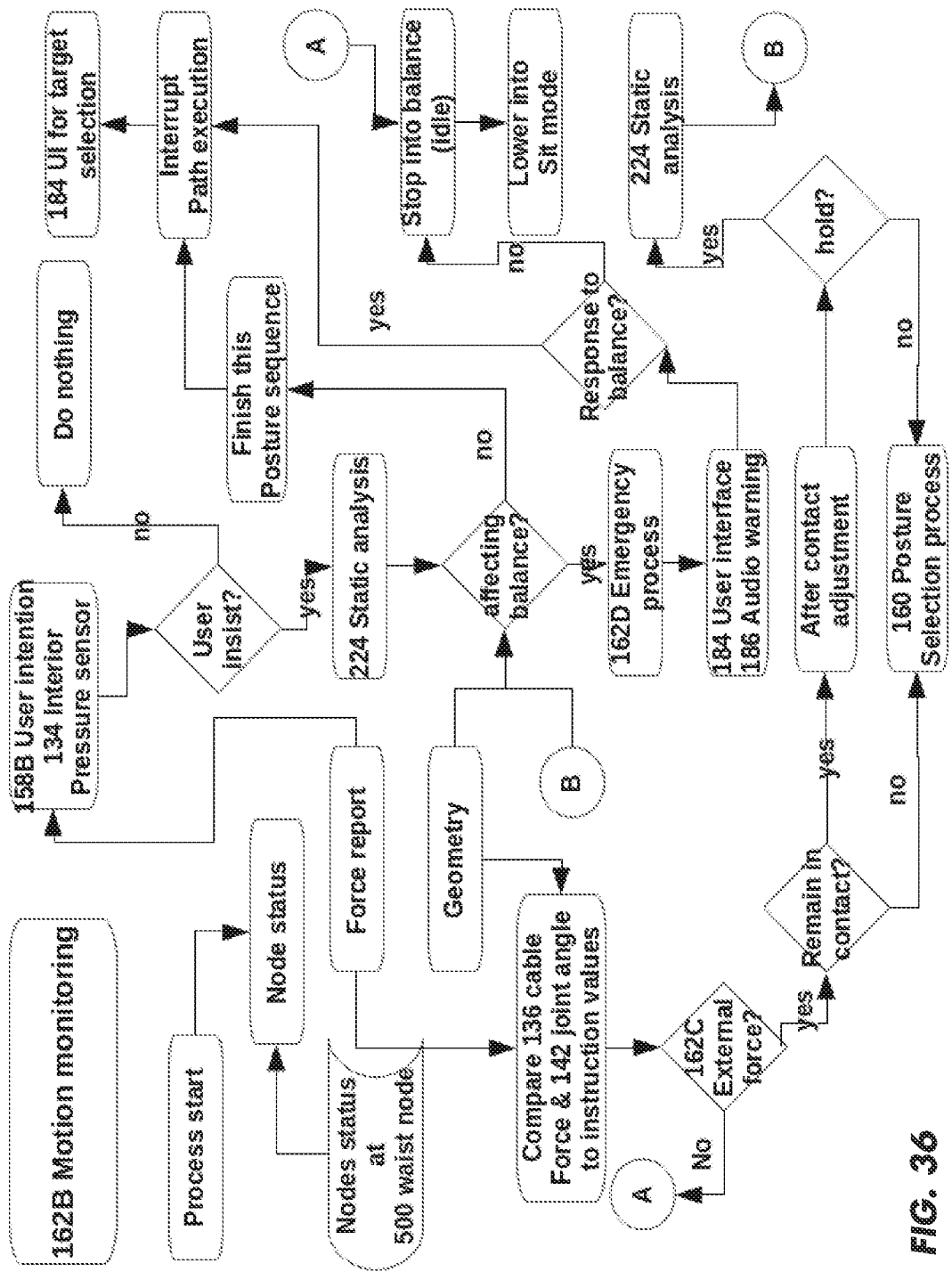
FIG. 36 is a process schematic of motion monitoring.

For other than initial time steps in the given time period, the reported encoder data is calculated by geometry process results in skeletal coordinates, the geometry data is compared with N-particles prediction data 218E for monitoring. The cable force process monitor reported external force 162C, user intention 158B, sole pressure sensors 132, reserved spring elastic energy and edge pressure sensors 148. In the user intention and the external force event, the process will call the motion monitoring process 162B (FIG. 36).

Figure 34:
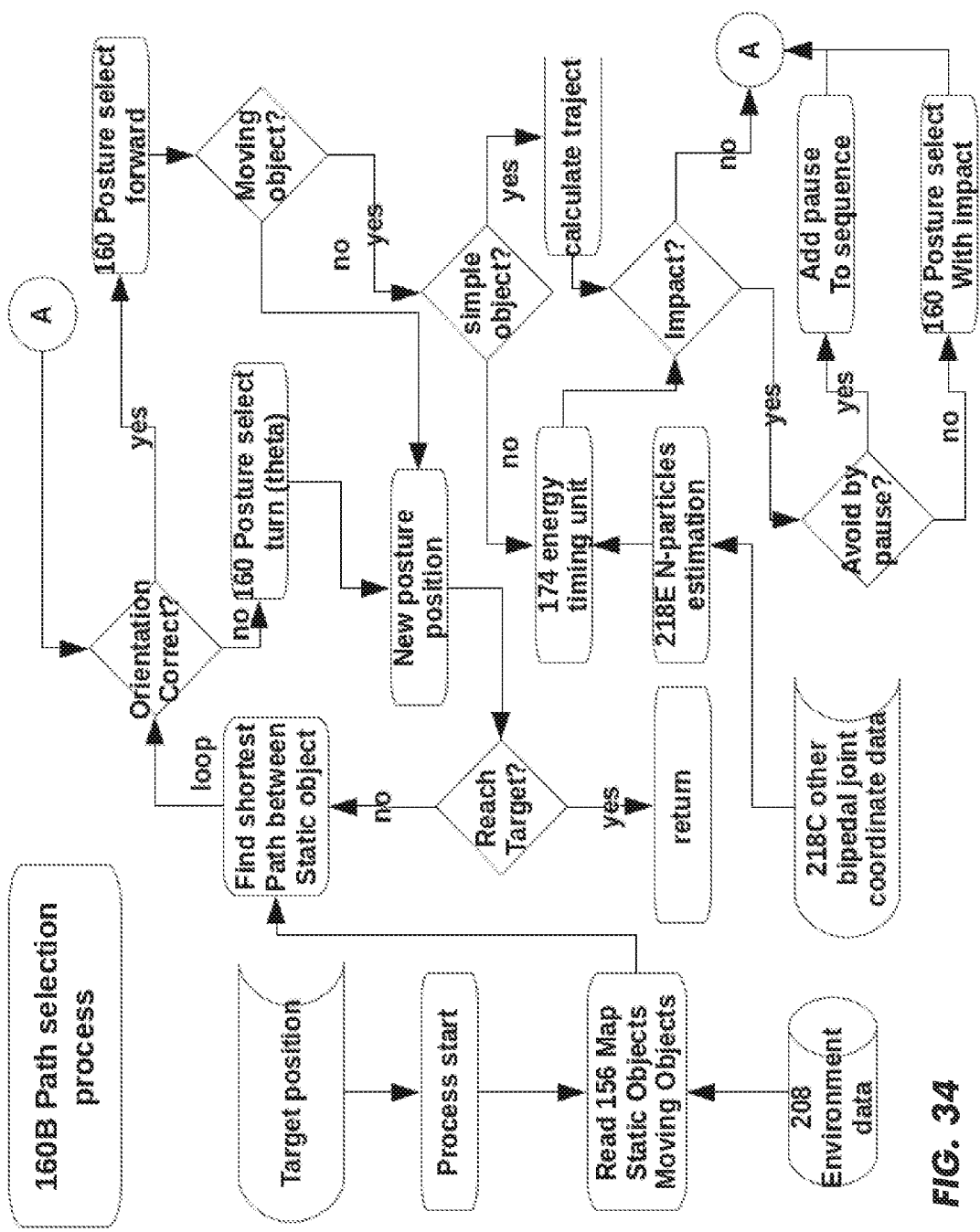
FIG. 34 is a process schematic of path selection process.
Figure 35:
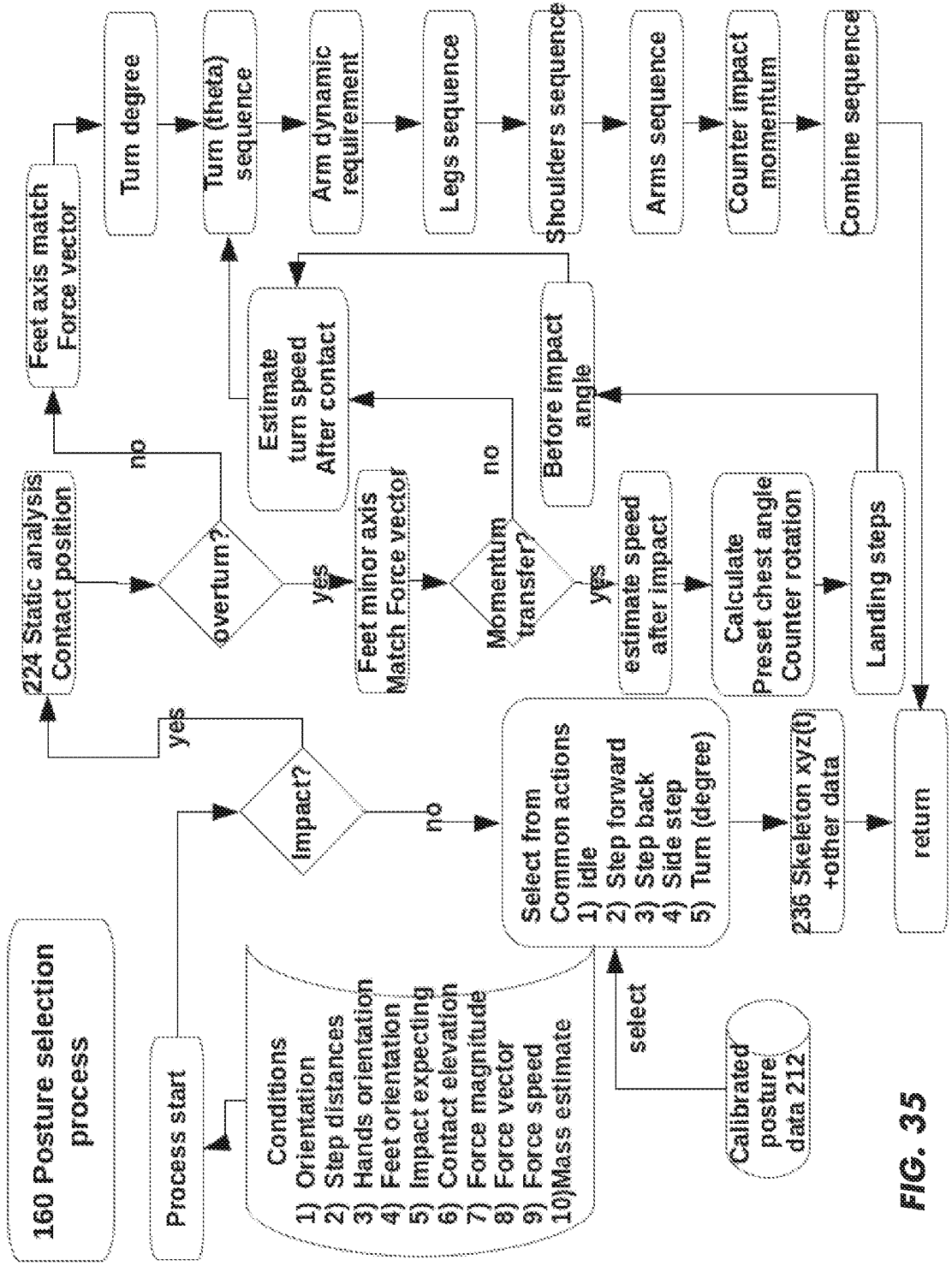
FIG. 35 is a process schematic of posture selection process.

FIG. 34 shows a process schematic for path selection unit 160B. This process is run on independent processor units CPU/GPU 180, which are on a computer board. The path selection unit 160B allows a planned motion series within a given environment, which are collaborating with surrounding objects and human activities. The process also records user routine activity, by using the historical data, the recognition and calibration effort can be minimized to improve efficiency in repeated motions.

The process starts by acquiring map information 208, includes static and moving object. Multiple path finding logic 178c apply, such as the shortest path algorithm to have first draft route selection through the static objects. Following, uses postures selection 160, provide joint coordinate definition as function of time. After each the postures step is selected with estimated time in space, the moving objects in the environment are checked for interferences. For moving objects, a pause of motion is added, if necessary, to avoid impact. The information is sent to posture selection process 160 (FIG. 35) with impact expectation, if impact is not avoidable. To prevent colliding with other human along the selected path in this time frame, the process checks the other bipedal joint coordinate data 218C, to verify if there is another existing bipedal ambulatory object exist. If there is a potential collision, the prediction is made based on the calculation of energy timing unit 174 (FIG. 38) and N-particles model prediction data 218E. Results of unavoidable impact prediction are sent to posture selection process 160

(FIG. 35) to plan for collaboration. The posture selection 160 defines a continuous joint adjustment values for the device 10 change position and configuration in balanced state. After the necessary adjustments, the envelope of postures through time occupies three dimensional space is plot with processed environment data 208 (FIG. 37) and shown in the user interface 184 for confirmation. The path selection unit 156 continuously simulates the next numbers of steps to ensure stability and free from impact for the device 10 through the surrounding space until the device 10 reaches target position.

The present invention uses a shortest distance maze solving algorithm for route selection. Other algorithm such as: Pledge algorithm, Wall follower, Dead-end filling, Recursive algorithm, and Maze-Routing algorithm can be used for multiple selection results for the user's best interest.

To further describe the user interface, the selected path is viewed from user display 190. The display can be for user wearing the device 10 or from remote control through Wi-Fi/cellular communication unit 196. An audio speaker 186 and microphone 188 or keypad 192 allows user to provide input decisions. The display of path selection process 160B starts with the device 10 in idle posture. The display draws static objects edge from environment data 208 (FIG. 37) and moving objects with projected trajectory. The user confirms the target position from the environment shown in display. Then, a path composed of multiple postures is shown with planned completion sequences for confirmation. The posture sequence is based on the user ambulation pattern data 210 (FIG. 37), stored from user's daily activities. In user's destination confirmation, when traveling in the recorded environment 208, the historical selected path are shown for quick retrieval.

FIG. 35 shows a process schematic of postures selection unit 160. The process is run on independent processor units CPU/GPU 180, which are on a computer board. Inputs from path selection process 160B (FIG. 34) includes: orientation of target posture, step distanced expected, target hands orientation, target feet orientation, impact prediction, impact contact elevation, impact force magnitude, impact force vector, impact force speed, and impact mass estimate. Access the calculated posture data 212 for acceleration of each frame elements. Dynamic load demand is calculated. Cables length time-history is calculated per gravitation, dynamic load plus the over-tension calculated by energy timing unit 174 (FIG. 38) results. If the impact likely, the cable length is calculated for additional over-tension to counter the impact event, to add a counter displacement (camber) before predicted impact. The release of cable force from the opposite side of contact counters unpleasant posture deformation generated by the impact. To further assist joint capacity, the special rigidity control device 68 is used, as compression link, to give compression support at the closing side of the joint. The timing of vacuum to the rigidity control device 68 is also activated.

Features of the postures selection unit 160 include considering device structural efficiency, balance, and being ready to cooperate and respond to force input. The process monitors, responds and settles into next command to incorporate user intention. In external force input conditions, the unit calculates risk and best strategy to engage contact. Finally, the unit assures the geometry result is verified by the N-particles analysis, static analysis to assure device configuration in the safe range of balance.

In calibrated posture data 212 (FIG. 30,37), multiple sets of skeletal joint coordinates in each time step is stored in the set. The sets include but not limited to, idle, step forward, step back ward, side step, turn step with given angle. In condition without impact predicted, the selection process is complete in returning data to the path selection process. The balance of the robotic mobility assistant device 10, when subject to external force impact, is provided along with the gravitational pull.

The present invention provides a set of rules of ambulation and posture 204 (FIG. 37) for the placement of feet, legs, torso, arms and the timing of energy conversion 174 (FIG. 38). In following these rules and processes, the robotic mobility assistant device 10 distribute the impact forces through the frame (compression), cable (tension) system while maintain balance supported by bipedal ambulatory movement. A node control network 500 to 534 provide control of rigidity and deformation of each joints to position the robotic mobility assistant device 10 in selected posture to perform function under static, dynamic, internal and external load. The calculated control series data 212 provides data for quick initial ambulatory planning.

While exist and after contact is initiated, the posture selection process 160 determined strategy of best pressure transfer from impact point through the robotic mobility assistant device 10. The contact angle's friction coefficient between contacting objects, the waist node sensor computation 150, and force calculation process decides the relative movement of the contacting vectors. The comparison with calculated posture data 212, static analysis model 224 estimate applied force given from input if impact preparation is needed. The force effect calculated is iterating through calling waist node sensor computation unit 150 (FIG. 33) for further posture adjustment and execution until contact pressure resolved.

The invention provides important factors for coordination between the robotic mobility assistant device 10 and other motion objects. The force reading during interaction in real time can be used as instruction and planning for maintaining contact and provide adequate coordinated output.

The present invention references a set of standard posture data 214, based on rules of ambulation and attitude 204, to prepare postural selection for given force input. The set of standard posture data 214 can be extended to further complex functions. A person wearing the robotic mobility assistant device 10 has an interface to operate the device 10. Alternatively, the device 10 can also be operated from an artificial intelligent system to perform variety of special tasks.

A standard posture data 214 prepared with a series of preset sequence of postures that satisfy the rules of ambulation and posture 204 (FIG. 37) in present invention. Through initiation of calibration, the calibrating process 154 (FIG. 30) uses user characteristic data 202 to convert the standard posture data 214 into calibrated posture data 212, which includes the calibration result from sequence calibration unit 154 (FIG. 30). The calibrated posture data 212 covers the commonly applied movement sequences with capacity to balance in holding device 10 in static and dynamic environment variations.

FIG. 35 also lists the process of selection using the calibrated posture data 212 in posture selection. The most common selections are for geometry adjustments only. On impact, contact to external object can be predicted and avoid through path selection process 160B (FIG. 34). The internal force created by user intention input is expected and provides with a balance margin to allow device 10 to be interrupted, and set back to idle sequence for new instructions from user. The external force applied to the system is expected to be prepared before impact. The magnitude and variation of force vector can be estimated and then confirmed only after contact.

FIG. 35 shows a schematic of preparing posture based on estimated impact momentum to place the device 10 configurations to three conditions: (1) hold, (2) hold and adjust position to the side to minimize impacting component, and (3) ready to take full impact and prepare to regain balance. The hold position condition can be decided with maximum capacity in the calibrated posture data 212. If sensed external force exceeding holding capacity, the posture selection process 160 gives next adjustment sequence to reduce impact component. The control of the rigidity of joints requires instructing rigid control devices 68A to 68E to assure the device 10 to balance against the remaining impact component and still in controlled postural changes. If the remaining impact component still larger than the holding capacity of according posture sequence, the posture selection process 160 gives instruction to remove resistance and into step back movement sequence until total control is regained.

Features of the present invention include (1) accounting for continuous effects after external force impact and (2) using posture adjustment in ambulatory range for continuous operation. The present invention considers the external force impact in a single event. It is prepared for continuous events sensing and sequences of adjustment.

FIG. 36 shows is a schematic of motion monitoring unit 162B. The process of this control unit is run on processor units CPU/GPU 180, which are on a computer board. The motion monitoring unit 162B is able though monitoring, responding, and settling into next command to incorporate user intentions. During external force input conditions, the unit calculates risk and best strategy to collaborate with engaging contact. There are two types of information being processed and examined for the robotic mobility device's 10 balance and health: (1) the encoder geometry data and (2) and force data. The device 10 is designed to follow user intention, provide energy assistance and sensing upcoming possible loss of balance or the possibility of external impact.

When an emergency is identified, such as a trend of losing balance, in trajectory of crashing, the process issues an audio warning first. For the situation that the force is generated by the user, but not affecting balance, there are two options taken: (1) if user does not insist through given time step cycles, the process finishes the planned selected posture, and (2) when user does insist, the process will not affect motor activity, the posture sequence will be completed in the current execution sequence. Then the selected path is interrupted and sent back to user interface 184, for user next decision on target and path selection 160B (FIG. 34,35). If the user intended trend predicted to be affecting balance, process calls to interrupt current posture execution, set posture into the closest balance state, apply gravitation calibration 152 into boot sequence 200 (FIG. 30) mode. Notice of user intention is sent to user interface unit 184 for next target selection, path selection 160b (FIG. 34) and posture selection 160 (FIG. 35).

For the situation that the force is generated by the external force events, the process calls to interrupt current posture execution. Depending on the magnitude and direction of external force, the process decides options through static analysis, and result in either hold position when capable, or to adjust posture to relief the applied load.

Emergency process unit 162D notices trends of losing balance and selects an immediate balance position that applies rigidity control 68 to 68E fixing all joints rotation into a balance posture and monitors user's reaction through interior pressure sensors 134. In the event of sensing user's struggle with large forces trending into loose balance, the device 10 continuously adjusting attitude to lower elevation, reducing falling impact.

The present invention can monitor and respond to user intentions and external forces at the waist node after initial contact. The edge pressure sensors 148 provide data to compare with non-contact independent kinetic states 214 with abrupt inclinometer sensor 130, accelerometer 130b readings. The force input location and amount to be calculated by static analysis model 224. The postures selection unit 160 (FIG. 35) engages and executes change of posture 198B to maintain device 10 balance accordingly. The same sequence can be performed by applying different type of sensors for geometry calculation and force inputs.

FIG. 37 shows a schematic of data storage. Groups of data are stored in a one or plurality of CPU/GPU 180 with RTOS, real-time operating system, 182 to provide adequate performance for data read/write, search, sort, update, add and delete with transaction management capabilities. The data storage is provided with connections to all processing units 150 to 178c to data exchange. The present invention includes, without limitation, data structure for boot sequence 200, user characteristics data 202, rules of ambulation and attitude 204, force calibration base line data 206, environment data 208, user ambulation pattern data 210, calibrated posture data 212, standard posture series data 214, current joint coordinates data 218, next joint coordinates data 218B, other bipedal joint coordinate data 218C and N-particles prediction data 218E.

The user characteristics data 202 record information collected during gravitation calibration process 152 and sequences calibration process 154 (FIG. 30) according to the specific user. Describing, but not limit to, specific cable length, pressure sensor reading. The data is used to derive the calibrated posture data 212.

The standard posture data 214 records a set of specifically designed bipedal ambulatory patterns. These bipedal ambulatory patterns are designed based on the following characteristics: (1) translation of static load demand, (2) dynamic load demand, and (3) external load carrying. The information describing, but not limit to, the joints coordinates as function of time step, velocity, acceleration and cable tension required for each posture sequence.

The calibrated posture data 212 record specific calculation result of combining force calibrated baseline data 206, user characteristics data 202 and standard posture data 214. The information describes, among other things, the specific cable length, pressure sensor reading. It is recorded for posture selection process 160 and node control unit 166. The data is ready for the specific user to perform bipedal ambulation and specific functions presented in this invention.

The environment data 208 record specific information describes, among other things, objects in the surrounding environment. The objects are stored in three dimensional format, binding magnetometer 146 reading and global position system 144 coordinates. All information is constantly updated by the map unit 156 (FIG. 29). The static object in the map is used for image recognition process to calculate device 10 relative position in the map. The moving object is filtered from the other and given trajectory property for the path selection unit 160B (FIG. 34).

The user ambulation pattern data 210 record specific user ambulation pattern. The information describing, but not limit to, the continuous device 10 joints coordinates, energy conservation timing performance, power consumption rate and posture performed. It also records coordination performance between the robotic mobility assistant device 10 and the specific user.

The rules of ambulation and posture 204 store information of specific rules of how postures should be calculated by posture selection unit 160 (FIG. 35) under static 224 and dynamics states 226. The rules are performed through a set of software functions working with posture configuration. Included but not limit to: General rules: (1) structurally awareness, perform physical input to other object within device 10 physical capacity. When accepting force input, either dynamic or reaction from contact, the impact is distributed throughout the entire device's frame, joint device and cable system. The result should satisfy minimum displacement of each cable. (2) The position of feet governs the translation vector between attitudes in bipedal ambulation. (3) In between frame components, the joint device angle variation is confined by the cable stretch capacity 70 72 (FIG. 22A,B) surround the joint. (4) When into the end of step transition, all joints need to be in a relatively rigid manner to counter the mass inertia in deceleration. (5) The specific posture selection unit 160 (FIG. 35) presents the equilibrium when arrive to the predicted target position, in the very end of the transition, the target leg starts convert the kinetic energy into elastic energy through rigidity control device (FIG. 10,11A,B) and cable spring box (FIG. 22B). At the beginning of the next step, the bending and torsional elastic energy is released from the tightened cable 70 (FIGS. 22A,22B) to initiate next attitude adjustment transition. (6) In each time step, if an external force acting on device 10 sensed by the cable force sensor 136, the adjustment is planned for the next best selected posture, to maintain balance and perform energy conservation.

In addition, there are ankle device rules: (1) coordinate between ankle 82, knees 88, hip 90B device for leg compression strut orientation. (2) Toe pitch 80 increase normal force to ground reaction to create larger friction and larger torsional eccentricity while conserve and release torsional elastic energy. (3) Adjust cable 402 404 406 408, rigidity control bend block 68c to assure approximate equal sole pressure sensor 132 reading. (4) Except in the case of no near equal sensor reading achieved in the case of reaching 90% of range of motion in any of the ankle rotational degree of freedom, fix ankle device for load transfer. Operate flexible axis device 66 to assure fixity at maximum load carrying state. There are knee device 90 rules: (1) coordinate between ankle 82, knees 88, hip 90B device for leg compression strut orientation. (2) Alternate extension and flexion to support force input to hip center 90B. (3) Control center of gravitation elevation, conversion of potential energy. 4/defined ankle 82 knee 88 hip 90b plane for required force output to hip center 90B.

There are hip device 90 rules: (1) device 10 orientation changes by adjust the hip device yaw relative to the baseline during directional transition. (2) The plumb line of device 10 Center of Gravity is maintained inside the enclosed area, on floor plane, defined by both heels and toes. 3/Hip 90B, knee 88, ankle 82 plane keep stable and equilibrium at orientation within plus and minus 45 degree from the local y axis, perpendicular to the line connecting two hip joints 90B. (4) The mass center above hip base 18 transfers between one hip center 90B into the other hip center 90B. The weight transfer is performed by hip base 18 roll 94. The roll lower the load supporting side and into the load taking leg. (5) The imaginary line connecting hip center 90B and ankle 82 provides a strut vector supporting vertical weight component, and horizontal component for mass acceleration. (6) Creating strut force by varying knee pitch 88 and ankle 82 86 angles. (7) The step movements initiate by hip roll, reduce supporting pressure at hip center 90B from the lifting leg, drive center of mass into the supporting hip with static plus dynamic load, following by fixing supporting hip joint, the lifting leg take no load and the gravitation balance initial springs 74 (FIG. 21) lift up the knee, ankle, and the preset of moving step is ready. (8) The joints of waist yaw 98 and roll 96 is strengthen and link by cable 434 to 442 (FIG. 26A,B) through hip base 18 connection to supporting leg. The target reaching lifting leg's self-weight is used to provide needed gravitational pull to drag the center of mass into target position.

There are waist device 96 98 rules: (1) in all the movement, the abdomen frame 20 and chest frame 22 is kept vertical, parallel to the gravitation force orientation. 2/The waist yaw 98 to keep minimum, the stable and equilibrium orientation is set at zero degree yaw.

There are waist device 98 and shoulder device 104 rules: The yaw rotation of chest 22, waist frame 20 relative to the global coordinate system drives shoulder joints circling around the yaw axis, the arms mass angular acceleration force will be carried by cables 444 to 456 (FIG. 25A,B) around shoulder.

There are shoulder device 102 to 106 rules: (1) coordinate between wrist 112, elbow 110, shoulder device 104 for arm compression strut orientation. (2) Shoulder, elbows vector has vertical and horizontal flexion range between 0 degree and 90 degree. (3) For orientation control, the reaching, pressure conduction, conversion of elastic energy, effect of dynamic efficiency in arm movement, center of mass of frames 24, 26, 28 should move within the plane defined by wrist joint 112, elbow joint 110 and shoulder joint 104. (4) For maximum force output on hip center 90B, vector defined by wrist 112 and shoulder 104 is most efficient in taking strut force, when it lined up with hip centers 90b and feet frames 12 orientation. (5) The most disadvantage orientation is when perpendicular to the above orientation.

FIG. 38 shows a schematic of energy timing unit 174. The process of this unit is run on processor unit CPU/GPU 180, which is on a computer board with on board memory, digital signal process unit and communication ports such as USB, USART, GPIO and I2C. The computer board is supplied with power by a portable battery pack. Specific software processes are written to execute the following process flow. The software programs are written by C, C++, Assembly, scripts or device specific languages to assure efficiency maintenance and improvement. The communication between processes on the same multiprocessor, multi-threads capable computing device will provide low level system functions.

The advantages of present invention are (1) synchronizing energy conversion timing by activating joint rigidity control device 68B, C, D, E (FIG. 10, 11A, 11B) and cable spring box 70 (FIG. 22B) elastic energy releasing, the device 10 (FIG. 1, 2) reaches higher efficiency with better mobility, and hence providing the foundation for the capability of avoiding impact and keeping balance. (2) By observing the angular change of each joint of the other bipedal ambulatory object through 170D (FIG. 29), the energy timing 174 functions are used to predict the trajectory of the object's next energy release, therefore, the prediction of movement trajectory of the other bipedal ambulatory object.

To further describe the energy timing process 174, when used in the device's 10 own energy timing calculation, the basic input data sources are: (1) the rotational encoder 142 (FIG. 13A) reading from all the joints, (2) the cable force readings from all the cable spring boxes 70 (FIG. 22A, B), (3) the device 10 acceleration from accelerometer 130B and (4) the target posture angular time history from posture selection process 160 (FIG. 35). In the legs movement planning bipedal ambulatory movement, the energy conversion also includes gravitational potential energy. During steps, the supporting ankle, knee and hip angle increase to lower the elevation of device's 10 center of gravity. This lower elevation uses gravitation force to load the ankle, knee and hip cable springs, and geometrically, providing the step out foot with reach distance. While the step out leg mass bringing center of gravity away from the supporting foot and the horizontal component of the supporting leg drives the device 10 toward target direction create kinetic energy.

The energy timing calculation has two modes of energy conversion: (1) from kinetic energy into elastic energy; in this stage, the device is moving toward the end of posture adjustment; from time t0 to t1 (FIG. 7) (2) from elastic energy, static position, to kinetic energy, movement, in the starting of posture adjustment; in this stage, the elastic energy is released to assist joint angle adjustment to start pushing the device toward target posture and into motion; from time t2 to t3 (FIG. 7).

The energy timing process is to calculate the timing of applying the energy conversion, based on the concept described in FIG. 5, 6, 7, 8 to the robotic mobility assistant device 10 (FIG. 1, 2). When in the first energy timing mode, from moving into static: (1) the spring box ratchets 70E (FIG. 22B) engage the springs to the angular change across joint, to allow the angular change to stretch the springs. The ratchets 70E disengage the springs when the target joint position achieved. The energy is stored in the elastic form within the stretched springs until next release. (2) The joint rigidity control blocks 68B, C, D, E (FIG. 10, 11A, 11B) are activated in sequence along the supporting leg: Ankle, Knee, Hip, Waist, Chest, Shoulder, Elbow to Wrist. With the joint rigidity activated from ground up, the frames 12-28 (FIG. 1, 2) become one rigid structure, so the reaction can be transferred from ground up to resist kinetic force produced in body mass deceleration. Further describe the invention, the user ambulation pattern data 210 is used to bypass calculation for repeated daily movement.

The second mode of energy timing calculation is to activate device 10 from the static mode into moving mode. The action is to engage node springs 70 (FIG. 22B) and release joint rigidity control blocks 68B, C, D, E (FIG. 10, 11A, 11B) and start joint angular adjustment. The timing is following the sequence of Wrist, Shoulder, Check, Waist, Hips, Knee and Ankle joint.

To further describe the energy timing unit 174 function in predicting movement trajectory of the other bipedal ambulatory object, the calculation is based on the sensor input of such an object, through the use of camera sensor 138 or infrared sensors 138B (FIG. 1). The image sequence is analyzed and the bipedal object is recognized by the computer vision calculation, if the object exists in the near surrounding. The result of calculation is the time history of object's joints coordinate xyz. This joint coordinate data, in each time step, is transformed into rotation angles at each joint degree of freedom (FIG. 4). With three continuous time steps, the angular velocity and acceleration can be calculated. The time history of joints coordinate also provides the acceleration of center of gravity of the other bipedal ambulatory object. The energy timing process calculates the sequence of joints that is connected to the ground, which from an angular acceleration curve set, is used to predict the likely energy release. The releasing speed is passing to the N-particle analysis model 222 (FIG. 3C) to perform the near future posture trajectory of the other bipedal ambulatory object.

DESCRIPTION OF NOTATIONS

10 robotic mobility assistant device
12AB feet frame(Calcaneus+Metatarsal)
14AB shin frame(Tibia+Fibula)
16AB thigh frame(Femur)
18 hip base frame(Ilium+Ischium)
20 abdomen frame
22 chest frame(Vertebrosternal rib cage)
24AB upper arm frame(humerus)
26AB forearm frame(Ulna+Radius)
28AB palm frame(Metacarpal)
30 length adjustment Connections;
32 bean bag inner thickness adjustable layer;
34 airtight chamber;
36 mechanical joint connections;
38 cable connector;
40 cable saddle;
42 cable tubes;
44 cable anchors
46 toe/heel electrical floor suction device
48 toe/heel electrical magnetic floor suction device
60 Mechanical Joint Devices;
62 electric air control valve
64 air pump
64B electric air pump
66 flexible axis device
68 rigidity control device
68B rigidity control compression pad
68C rigidity control bend block
68D rigidity control compression block A
68E rigidity control compression block B
69 beads
70 cable spring box
70A cable spring
70B Auxiliary Cable
70C spring adjustment space
70D base plate
70E ratchet
70F press plate
70G control I/O
70H actuator control
72 cable actuator
74 gravitation balance initial springs
76 non-linear tensile spring pad
78 node processing unit
80 toe pitch
82 ankle pitch (Tibia, Fibula, Talus)
84 ankle yaw
86 ankle roll
88 knee pitch (Tibia, Femur)
90 hip pitch (Head of Femur, Acetubulum on ilium, Ischium)
90B approximate hip center
92 hip yaw
94 hip roll
94B hip roll track block
96 waist roll (L03, L045 Lumbar Vertebra)
98 waist yaw
100 chest pitch (L01 Lumbar Vertebra, T12 Thoracic Vertebra)
102 shoulder clavicle roll/yaw (Manubrium+Clavicle+Scapula)

102B shoulder clavicle ball joint
104 shoulder roll/yaw (Glenoid Cavity, Humerus Head)
104B shoulder yaw shaft and journal
106 shoulder pitch (Glenoid Cavity, Humerus Head)
106B shoulder pitch shaft and journal
108 upper arm axial rotation yaw
110 elbow pitch (Humerus, Ulna+Radius)
112 wrist yaw (Ulna+Radius)
130 dual axis inclinometer sensor
130B accelerometer
132 sole pressure sensor
132B sole distance sensor
134 interior pressure sensor
136 cable force sensor
138 camera sensor
138B Infrared Sensor
140 air pressure sensor (airtight chamber)
142 encoder (extension shaft and journal)
142B stretch sensor
144 GPS global positioning system
146 Magnetometer
148 edge pressure sensors
150 waist node computation unit
152 gravitation calibration unit
154 Sequence calibration unit
156 map unit
156B path selection process
158B user intent sensing unit
160 postures selection unit
160B path selection unit
162 node spring box control unit
162B motion monitoring unit
162C external force monitoring unit
162D emergency process
166 node control unit
168 N-particles simulation unit
170 computer vision recognition unit
170B moving object recognition unit
170C camera position recognition unit
170D bipedal ambulatory recognition unit
172 vertical edge recognition
174 energy timing unit
178 central control unit
178C path finding logic
176 electric battery pack or alike
180 CPU/GPU
182 RTOS real-time operating system
184 user interface
186 speaker
188 microphone
190 video/audio display
190C Device location
192 keypad
194 direct neural interface (DNI)
196 WiFi/cellular communication unit
198 single chip microcomputer/controller
198B node control network
200 boot sequence data
202 user characteristics data
204 rules of ambulation and posture data
206 force calibration baseline data
208 environment data
210 user ambulation pattern data
212 calibrated posture data
214 standard posture data
218 current joint coordinate data
218B next joint coordinate data
218C other bipedal joint coordinate data
218E N-particles prediction data
220 Analysis
222 N-particles model
224 static analysis model
226 dynamic analysis model
228 particle node
230 shell link
232 cable link
234 skeleton center
236 skeleton data
250 torsional timing control cable
252 right ankle-knee-hip out bend
254 right ankle-knee-hip in bend
256 right torso twist bend
258 right shoulder-elbow-wrist out bend
260 right shoulder-elbow-wrist in bend
280 left ankle-knee-hip out bend
282 left ankle-knee-hip in bend
284 left torso twist bend
286 left shoulder-elbow-wrist out bend
288 left shoulder-elbow-wrist in bend
300 potential, kinetic and elastic energy conversion
302 bending, torsion elastic energy
304 attitude potential energy
306 postural kinetic energy
307 synchronize timing
Cable Motor
400 toe pitch cable (plantar flexion)
402 ankle eversion (peroneus group)
404 ankle inversion (extrinsic posterior)
406 ankle dorsiflexion (dorsiflexion)
408 ankle plantarflexion (gastrocnemius)
410 knee extension (quadriceps femoris)
412 knee flexion (bicep femrois)
414 hip extension (hamstrings)
416 hip flexion (illiacus+psoas major)
418 hip medial rotation out (obturator gemellus)
420 hip medial rotation in
422 hip lateral flexion (gluteus medius)
424 hip lateral flexion out (tensor facias latae)
428 hip lateral flexion in back (gracilis)
430 hip lateral flexion in front (gracilis)
432 hip lateral flexion stable
434 hip abdomen front
436 hip abdomen lateral
438 hip abdomen back
440 abdomen chest front
442 abdomen chest back
444 shoulder clavicle up (levator scapulae)
446 shoulder clavicle down (subclavius)
448 shoulder clavicle in (trapezius)
450 shoulder arm up (anterior deltoid)
452 shoulder arm back (*teres* major)
454 shoulder arm front down (pectoralis major)
456 shoulder arm front lateral (coracobrachialis)
458 upper arm lateral rotation (infraspinatus)
460 elbow flexion (brachioradialis)
462 elbow extensor (triceps brachii)
464 forearm twist (paronator guadratus)
500 waist node
502 right hip node
504 right knee node
506 right ankle node
508 right toe node
510 left hip node
512 left knee node 514 left ankle node
516 left toe node
518 chest node
520 right shoulder node 1
522 right shoulder node 2
524 right elbow node
526 right wrist node
528 left shoulder node 1
530 left shoulder node 2
532 left elbow node
534 left wrist node The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A powered exoskeleton, which is configurable to be worn by a person, that comprises:
   (a) a plurality of first and second lower limb frame members configured to be coupled to the person's first and second legs wherein the first and second lower limb frame members include respective first and second bead-filled, air-tight compartments;
   (b) a plurality of first and second mechanical joint means for coupling the plurality of first and second lower limb frame members;
   (c) a plurality of third and fourth upper limb frame members configured to be coupled to the person's first and second arms wherein the third and fourth upper limb frame members include respective third and fourth bead-filled, air-tight compartments;
   (d) a plurality of third and fourth mechanical joint means for coupling the plurality of first and second lower limb frame members;
   (e) a plurality of fifth frame members configured to be coupled to the person's torso wherein one or more of the fifth limb frame members include respective one or more fifth bead-filled, air-tight compartments;
   (f) a plurality of fifth mechanical joint means for coupling the fifth frame members; and
   (g) means for regulating the pressure inside the bead-filled air-tight compartments to manipulate the rigidity of the frame members to facilitate coordinated movement of the exoskeleton; and wherein at least one of the frame members defines a vacuum chamber that is in regulated gaseous communication with a bead-filled air-tight compartment therein such that removal of gases from a bead-filled air-tight compartment compresses the bead-filled air-tight compartment and increases the rigidity of the bead-filled air-tight compartment.

2. The exoskeleton of claim 1 comprising a gaseous pump that selectively increases the negative pressure within one or more of the bead-filled air-tight compartments to facilitate coordinated movement of the frame members.

3. The exoskeleton of claim 2 wherein removing gas from the bead-filled air-tight compartments disposed in the first, second, third and fourth limb frame members and in the fifth frame member causes the first, second, third and fourth limb frame members and in the fifth frame member to compress around the person to transfer the person's carrying load onto the first, second, third and fourth limb frame members and the fifth frame member in order to slow or reduce the person's motions at the mechanical joints and to slow or reduce the person's angular change of his biological joint to facilitate coordinated movement.

4. The exoskeleton of claim 1 wherein the bead-filled air-tight compartments generate compressive forces in the frame members in which the compartments are disposed wherein the compressive forces are imparted onto the person's legs, arms and torso to slow and reduce the person's motion.

5. The exoskeleton of claim 1 wherein each of the frame members defines a vacuum chamber that is in regulated gaseous communication with a bead-filled air-tight compartment therein such that removal of gases from a bead-filled air-tight compartment compresses the bead-filled air-tight compartment and increases the rigidity of the bead-filled air-tight compartment.

6. The exoskeleton of claim 1 wherein the first and second lower limb frame members define a vacuum chamber that is in regulated gaseous communication with the first and second bead-filled air-tight compartments therein such that removal of gases from the first and second bead-filled air-tight compartments compresses the first and second bead-filled air-tight compartments and increases the rigidity of the first and second bead-filled air-tight compartments.

7. The exoskeleton of claim 1 wherein the plurality of fifth frame members defines a vacuum chamber that is in regulated gaseous communication with the one or more fifth bead-filled air-tight compartments therein such that removal of gases from the one or more fifth bead-filled air-tight compartments compresses the one or more fifth bead-filled air-tight compartments and increases the rigidity of the one or more fifth bead-filled air-tight compartments.

8. A method of operating a powered exoskeleton as defined in claim 1 when worn by a person, wherein the method comprises:
   i) calibrating the powered exoskeleton to the user's individual physical characteristics;
   ii) monitoring the pressures at selected of parts of the powered exoskeleton to generate a plurality of pressure measurements that are indicative of the user's anticipated bodily movements, position and balance;
   iii) monitoring the environment surrounding the powered exoskeleton to generate a plurality of environmental readings that are indicative of potential obstacles; and
   iv) controlling movement of the powered exoskeleton towards a target position by continuously activating selected actuators in response to the plurality of pressure measurements and plurality of environmental readings to facilitate movement along a selected path.

9. The method of claim 8 wherein calibrating the powered exoskeleton aligns the frame members to the person's body proportions and biological joint degrees of freedom.

10. The method of claim 8 wherein calibrating the powered exoskeleton adjusts frame member force calculations for the person's motion and not in motion.

11. The method of claim 8 wherein monitoring the pressure employs synchronized sensors for coordinated manipulation of energy conversion devices to match the person's anticipated bodily movements, positions and balance.

12. The method of claim 11 wherein the person's anticipated bodily movements are predicted for stabilized posture trajectories based on prior and current sensor data.

13. The method of claim 8 wherein the environmental readings map sensor data together with the person's predicted bodily movements, position and balance for best route selections.

14. The method of claim 8 wherein environmental readings are consolidated to predict impact and provide impact avoidance for the person.

15. The method of claim 8 such that in the event that imminent collision with a potential obstacle, a protocol is activated to reduce impact force by stabilizing the person into balanced postures with coordinated manipulation of energy conversion devices.

16. The method of claim 8 wherein monitoring the environment comprises assessing a margin of balance measurement from sensor readings to determine the person's motion stability relative to the environment surrounding the powered exoskeleton and to activate stability adjustments as necessary.

17. The method of claim 16 wherein in the event the margin of balance measurement exceeds a limit and the person is not balanced, coordinated manipulation of energy conversion devices are activated to stabilize the person towards balanced predicted bodily movements.

18. The method of claim 8 wherein controlling movement employs energy conversion, that is controlled in response to the person's bodily movements, to preload cable springs using selected cable actuators for increase torque when acting with rigidity devices to facilitate the person's bodily movements towards stabilized postures.

19. The method of claim 8 wherein the first and second lower limb frame members define a vacuum chamber that is in regulated gaseous communication with the first and second bead-filled air-tight compartments therein such that removal of gases from the first and second bead-filled air-tight compartments compresses the first and second bead-filled air-tight compartments and increases the rigidity of the first and second bead-filled air-tight compartments.

20. The method of claim 8 wherein the plurality of fifth frame members defines a vacuum chamber that is in regulated gaseous communication with the one or more fifth bead-filled air-tight compartments therein such that removal of gases from the one or more fifth bead-filled air-tight compartments compresses the one or more fifth bead-filled air-tight compartments and increases the rigidity of the one or more fifth bead-filled air-tight compartments.

* * * * *